United States Patent
Crawford et al.

(10) Patent No.: US 10,550,117 B2
(45) Date of Patent: Feb. 4, 2020

(54) 2-AZABICYCLO[3.1.0]HEXAN-3-ONE DERIVATIVES AND METHODS OF USE

(71) Applicant: Genentech, Inc., South San Francisco, CA (US)

(72) Inventors: James John Crawford, San Francisco, CA (US); Aleksandr Kolesnikov, San Francisco, CA (US); Jianwen A. Feng, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/221,274

(22) Filed: Dec. 14, 2018

(65) Prior Publication Data
US 2019/0119274 A1    Apr. 25, 2019

Related U.S. Application Data

(63) Continuation of application No. PCT/EP2017/071264, filed on Aug. 23, 2017.

(60) Provisional application No. 62/379,192, filed on Aug. 24, 2016.

(51) Int. Cl.
| | | |
|---|---|---|
| C07D 471/04 | (2006.01) | |
| C07D 417/10 | (2006.01) | |
| A61P 27/14 | (2006.01) | |
| A61P 37/06 | (2006.01) | |
| A61P 17/00 | (2006.01) | |
| A61P 19/02 | (2006.01) | |
| A61P 1/00 | (2006.01) | |
| A61P 11/00 | (2006.01) | |

(52) U.S. Cl.
CPC ......... *C07D 471/04* (2013.01); *C07D 417/10* (2013.01); *A61P 1/00* (2018.01); *A61P 11/00* (2018.01); *A61P 17/00* (2018.01); *A61P 19/02* (2018.01); *A61P 27/14* (2018.01); *A61P 37/06* (2018.01)

(58) Field of Classification Search
None
See application file for complete search history.

(56) References Cited

U.S. PATENT DOCUMENTS

| | | | |
|---|---|---|---|
| 8,637,529 B2 | 1/2014 | Woller et al. | |
| 2012/0214762 A1 | 8/2012 | Staben et al. | |
| 2015/0057260 A1 | 2/2015 | Blaquiere et al. | |
| 2015/0065482 A1 | 3/2015 | Blaquiere et al. | |

FOREIGN PATENT DOCUMENTS

| | | |
|---|---|---|
| WO | 2008/105515 A1 | 4/2008 |
| WO | 2009/158011 A1 | 12/2009 |
| WO | 2012/123522 A1 | 9/2012 |
| WO | 2014/174021 A1 | 10/2014 |
| WO | 2015/025025 A1 | 2/2015 |
| WO | 2015/025026 A1 | 2/2015 |
| WO | 2015/044267 A1 | 4/2015 |

OTHER PUBLICATIONS

Silva, A., Mini-Reviews in Medicinal Chemistry, 2005, vol. 5, pp. 893-014.*
Baudy et al., "A robust in vitro screening assay to identify NF-κB inhibitors for inflammatory muscle diseases" International Immunopharmacology 9(10):1209-1214.
Hayden et al., "NF-κB, the first quarter-century: remarkable progress and outstanding questions" Genes & Dev. 26:203-234 ( 2012).
ISR and Written Opinion for PCT/CN2013/000994 (dated Jun. 10, 2014).
ISR and Written Opinion for PCT/EP2014/067872 (dated Dec. 9, 2014).
ISR and Written Opinion for PCT/EP2016/053805 (dated May 18, 2016).
ISR and Written Opinion for PCT/EP2017/071263 (dated Sep. 21, 2017).
ISR and Written Opinion for PCT/EP2017/071264 (dated Sep. 21, 2017).
Moynagh, "The NF-κB pathway" Journal of Cell Science 118:4589-4592 ( 2005).
PCT ISR and Written Opinion for PCT/CN2013/000993 (dated Jun. 9, 2014).
PCT ISR for PCT/EP2014/067873 dated Dec. 9, 2014.
Sebban et al., "NF-κB and inflammation in genetic disease" Biochemical Pharmacology 72(9):1153-1160 ( 2006).
Siebenlist et al., "Control of lymphocyte development by nuclear factor-kappaB." Nat Rev Immunol. 5(6):435-45 ( 2005).
Tak et al., "NF-κB: a key role in inflammatory diseases" J Clin Invest. 107(1 Suppl 7-11) ( 2001).

* cited by examiner

*Primary Examiner* — Heidi Reese
(74) *Attorney, Agent, or Firm* — Kevin M Clark

(57) ABSTRACT

The invention relates to compounds of formula (I):

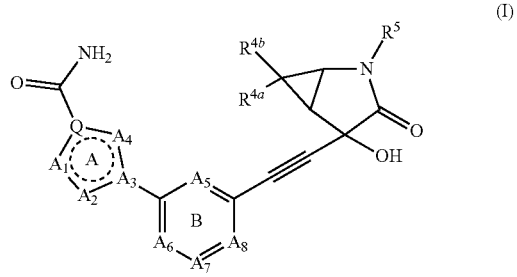

wherein Q, $A_1$, $A_2$, $A_3$, $A_5$, $A_6$, $A_7$, $A_8$, $R^{4a}$, $R^{4b}$ and $R^5$ are as described herein. Compounds of formula (I) and pharmaceutical compositions thereof are useful in the treatment of diseases and disorders in which undesired or overactivation of NF-kB signaling is observed.

34 Claims, 2 Drawing Sheets

2-AZABICYCLO[3.1.0]HEXAN-3-ONE DERIVATIVES AND METHODS OF USE

CROSS-REFERENCE TO RELATED APPLICATIONS

This application is a continuation of International Application No. PCT/EP2017/071264, filed Aug. 23, 2017, which claims priority to U.S. Provisional Patent Application No. 62/379,192, filed Aug. 24, 2016, the disclosures of each of which are incorporated herein by reference in its entirety.

FIELD OF THE INVENTION

The present invention relates to organic compounds useful for therapy or prophylaxis in a mammal, and in particular to 2-azabicyclo[3.1.0]hexan-3-one compounds that are inhibitors of NF-kB-inducing kinase (NIK) useful for treating cancer, fibrotic conditions, inflammatory diseases and other conditions responsive to NIK inhibition.

BACKGROUND OF THE INVENTION

NF-kB inducing kinase (NIK) is also known as MAPK kinase kinase 14 (MAP3K14) and is a serine/threonine kinase and a member of the MAPK family. It was originally identified in a two-hybrid screen as a binding partner of TNF receptor (TNFR) associated factor 2 (TRAF2), see, Malinin, N L, et al., Nature, 1997, 385:540-4. Overexpression of NIK leads to the activation of NF-kB and dominant negative forms of NIK lacking kinase activity were able to inhibit NF-kB activation in response to TNF and IL-1 treatment. Thus, NIK has been identified as an important component of the NF-kB signaling pathway. Scientific research has shown that blocking the NF-kB signaling pathway in cancer cells can cause such cells to stop proliferating, to die, or to become more sensitive to the action of other anti-cancer therapies. Additionally, NIK is required for non-canonical NF-kB signaling downstream of TNFRSF receptors which play a role in many inflammatory conditions, such as lupus (including systemic lupus erythematosus), rheumatoid arthritis, inflammatory bowel disease, arthritis, sepsis, gastritis and asthma, among others. Accordingly, organic compounds capable of inhibiting NIK and thereby inhibiting, weakening or lessening the undesired or over-activation of the NF-kB signaling pathway can have a therapeutic benefit for the treatment diseases and disorders for which such undesired or over-activation of NF-kB signaling is observed.

2-Azabicyclo[3.1.0]Hexan-3-One Derivatives and Methods of Use

BRIEF SUMMARY OF THE INVENTION

Disclosed are 4-alkynyl-4-hydroxy-2-azabicyclo[3.1.0] hexan-3-one compounds that are inhibitors of NIK kinase, compositions containing one or more of these compounds and methods for treating diseases mediated by NIK kinase such as cancer and inflammatory diseases.

In one aspect, provided is a compound of formula (I):

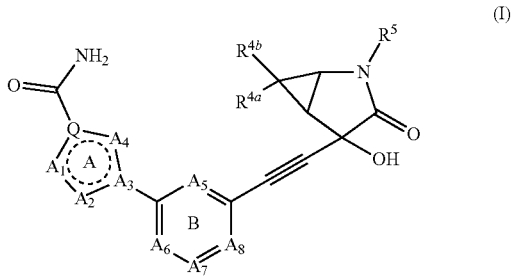

or a stereoisomer, tautomer, solvate, prodrug or salt thereof, wherein:
  ring A is a monocycle or a fused bicycle;
  Q is N or C, wherein when Q is N, then the bond between $A_1$ and Q is not a double bond and the bond between Q and $A_4$ is not a double bond;
  $A_1$ is $NR^1$, N, S, $CR^1$ or $CHR^1$;
  $A_2$ is $NR^2$, N, O, S, $CR^2$ or $CHR^2$;
  $A_3$ is N or C;
  $A_4$ is N;
  provided that no more than two of (i)-(iii) apply: (i) $A_1$ is $NR^1$ or N, (ii) $A_2$ is $NR^2$ or N, and (iii) $A_3$ is N;
  each $R^1$ is independently selected from the group consisting of H, halogen, $-NR^aR^b$, $-NHC(O)NR^aR^b$, $-NHS(O)_2-C_1-C_3$ alkyl, $C_1-C_3$ alkyl, $C_3-C_7$ cycloalkyl, $C_1-C_3$ alkoxy and 3-11 membered heterocyclyl, wherein the $C_1-C_3$ alkyl of $R^1$ is optionally substituted by F, OH, CN, SH, $C_1-C_3$ alkoxy or 3-11 membered heterocyclyl; the $C_3-C_7$ cycloalkyl of $R^1$ is optionally substituted by F, OH, CN, SH, $CH_3$ or $CF_3$; the $C_1-C_3$ alkoxy of $R^1$ is optionally substituted by F, OH, CN or SH; and the 3-11 membered heterocyclyl of $R^1$ is optionally substituted by F, OH, CN, SH, $CF_3$ or $C_1-C_3$ alkyl,
  each $R^2$ is independently selected from the group consisting of H, $NR^aR^b$, $C_1-C_6$ alkyl, $C_3-C_7$ cycloalkyl, $C_1-C_6$ alkoxy, phenyl and 3-11 membered heterocyclyl, wherein the $C_1-C_6$ alkyl, $C_3-C_7$ cycloalkyl, $C_1-C_6$ alkoxy, phenyl and 3-11 membered heterocyclyl of $R^2$ is optionally substituted by $R^c$; or
  $R^1$ and $R^2$ are taken together with the atoms to which they are attached to form a cyclic group selected from the group consisting of $C_3-C_7$ cycloalkyl, phenyl and 3-11 membered heterocyclyl, wherein the cyclic group is optionally substituted by $R^d$;
  each $R^{4a}$ and $R^{4b}$ is independently H or F;
  $R^5$ is $C_1-C_6$ alkyl or $C_3-C_4$ cycloalkyl, wherein the $C_1-C_6$ alkyl and $C_3-C_4$ cycloalkyl of $R^5$ are independently optionally substituted by halogen, OH, or $C_1-C_6$ alkoxy;
  each $A_5$, $A_6$, $A_7$ and $A_8$ is independently N or $CR^6$, provided that at least three of $A_5$, $A_6$, $A_7$ and $A_8$ are independently $CR^6$;
  each $R^6$ is independently selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;
  $R^a$ is selected from the group consisting of H and $C_1-C_6$ alkyl optionally substituted by $C_1-C_3$ alkoxy, F, OH, CN, SH, $CH_3$ or $CF_3$;
  $R^b$ is selected from the group consisting of H, $C_1-C_6$ alkyl, $C_1-C_6$ alkoxy, $C_3-C_6$ cycloalkyl, $C(O)R^g$, phenyl and 3-11 membered heterocyclyl wherein $R^b$ may be optionally substituted by $C_1-C_3$ alkoxy, F, OH, CN, SH, $CH_3$ or $CF_3$;

$R^c$ and $R^d$ are each independently selected from the group consisting of halogen, —$(X^1)_{0-1}$—CN, —$(X^1)_{0-1}$—NO$_2$, —$(X^1)_{0-1}$—SF$_5$, —$(X^1)_{0-1}$—OH, —$(X^1)_{0-1}$—NH$_2$, —$(X^1)_{0-1}$—N(H)(R$^{1a}$), —$(X^1)_{0-1}$—N(R$^{1b}$)(R$^{1a}$), —$(X^1)_{0-1}$—CF$_3$, C$_1$-C$_6$ alkyl, C$_1$-C$_6$ haloalkyl, C$_1$-C$_6$ heteroalkyl, C$_1$-C$_6$ alkoxy, C$_1$-C$_6$ alkylthio, oxo, —$(X^1)_{0-1}$—C$_1$-C$_6$ alkyl, —$(X^1)_{0-1}$—C$_3$-C$_{10}$ cycloalkyl, —O—C$_3$-C$_{10}$ cycloalkyl, —$(X^1)_{0-1}$-3-11 membered heterocyclyl, —$(X^1)_{0-1}$—C$_6$-C$_{10}$ aryl, —C(=O)$(X^1)_{0-1}$—C$_3$-C$_{10}$ cycloalkyl, —C(=O)$(X^1)_{0-1}$-3-11 membered heterocyclyl, —$(X^1)_{0-1}$—C(=Y$^1$)N(H)(R$^{1a}$), —$(X^1)_{0-1}$—C(=Y$^1$)NH$_2$, —$(X^1)_{0-1}$—C(=Y$^1$)N(R$^{1a}$)(R$^{1b}$), —$(X^1)_{0-1}$—C(=Y$^1$)OR$^{1a}$, —$(X^1)_{0-1}$—C(=Y$^1$)OH, —$(X^1)_{0-1}$—N(H)C(=Y$^1$)(R$^{1a}$), —$(X^1)_{0-1}$—N(R$^{1b}$)C(=Y$^1$)(R$^{1a}$), —$(X^1)_{0-1}$—N(R$^{1b}$)C(=Y$^1$)(H), —$(X^1)_{0-1}$—N(H)C(=Y$^1$)OR$^{1a}$, —$(X^1)_{0-1}$—N(R$^{1b}$)C(=Y$^1$)OR$^{1a}$, —$(X^1)_{0-1}$—S(O)$_{1-2}$R$^{1a}$, —$(X^1)_{0-1}$—N(H)S(O)$_{1-2}$R$^{1a}$, —$(X^1)_{0-1}$—N(R$^{1b}$)S(O)$_{1-2}$R$^{1a}$, —$(X^1)_{0-1}$—S(O)$_{0-1}$N(H)(R$^{1a}$), —$(X^1)_{0-1}$—S(O)$_{0-1}$N(R$^{1b}$)(R$^{1a}$), —$(X^1)_{0-1}$—S(O)$_{0-1}$NH$_2$, —$(X^1)_{0-1}$—S(=O)(=NR$^{1b}$)R$^{1a}$, —$(X^1)_{0-1}$—C(=Y$^1$)R$^{1a}$, —$(X^1)_{0-1}$—C(=Y$^1$)H, —$(X^1)_{0-1}$—C(=NOH)R$^{1a}$, —$(X^1)_{0-1}$—C(=NOR$^{1b}$)R$^{1a}$, —$(X^1)_{0-1}$—NHC(=Y$^1$)N(H)(R$^{1a}$), —$(X^1)_{0-1}$—NHC(=Y$^1$)NH$_2$, —$(X^1)_{0-1}$—NHC(=Y$^1$)N(R$^{1b}$)(R$^{1a}$), —$(X^1)_{0-1}$—N(R$^{1a}$)C(=Y$^1$)N(H)(R$^{1a}$), —$(X^1)_{0-1}$—N(R$^{1a}$)C(=Y$^1$)N(R$^{1a}$)(R$^{1b}$), —$(X^1)_{0-1}$—N(R$^{1a}$)C(=Y$^1$)NH$_2$, —$(X^1)_{0-1}$—OC(=Y$^1$)R$^{1a}$, —$(X^1)_{0-1}$—OC(=Y$^1$)H, —$(X^1)_{0-1}$—OC(=Y)OR$^{1a}$, —$(X^1)_{0-1}$—OP(=Y$^1$)(OR$^{1a}$)(OR$^{1b}$), —$(X^1)$—SC(=Y$^1$)OR$^{1a}$ and —$(X^1)$—SC(=Y$^1$)N(R$^{1a}$)(R$^{1b}$); wherein $X^1$ is selected from the group consisting of C$_1$-C$_6$ alkylene, C$_1$-C$_6$ heteroalkylene, C$_2$-C$_6$ alkenylene, C$_2$-C$_6$ alkynylene, C$_1$-C$_6$ alkyleneoxy, C$_3$-C$_7$ cycloalkylene, 3-11 membered heterocyclylene and phenylene; R$^{1a}$ and R$^{1b}$ are each independently selected from the group consisting of C$_1$-C$_6$ alkyl, C$_1$-C$_6$ haloalkyl, C$_1$-C$_6$ heteroalkyl, C$_3$-C$_7$ cycloalkyl, (C$_3$-C$_7$ cycloalkylene)C$_1$-C$_6$ alkyl, 3-11 membered heterocyclyl, (3-11 membered heterocyclylene)C$_1$-C$_6$ alkyl, phenyl, and (C$_6$-C$_{10}$ arylene)C$_1$-C$_6$ alkyl, or R$^{1a}$ and R$^{1b}$, when attached to the same nitrogen atom, are taken together with the nitrogen to which they are attached to form a 3-11 membered heterocyclyl comprising 0-3 additional heteroatoms selected from N, O and S; Y$^1$ is O, NR$^{1c}$ or S wherein R$^{1c}$ is H or C$_1$-C$_6$ alkyl; wherein any portion of an R$^c$ or R$^d$ substituent, including R$^{1a}$, R$^{1b}$ and R$^{1c}$, at each occurrence is independently further substituted by from 0 to 4 R$^f$ substituents selected from the group consisting of halogen, CN, NO$_2$, SF$_5$, OH, NH$_2$, —N(C$_1$-C$_6$ alkyl)$_2$, —NH(C$_1$-C$_6$ alkyl), oxo, C$_1$-C$_6$ alkyl, —(C$_2$-C$_6$ alkynylene)-(3-11 membered heterocyclyl, wherein the heterocyclyl is optionally substituted by R$^e$), C$_1$-C$_6$ hydroxyalkyl, C$_1$-C$_6$ heteroalkyl, C$_1$-C$_6$ alkoxy, C$_1$-C$_6$ alkylthio, C$_3$-C$_7$ cycloalkyl, 3-11 membered heterocyclyl, —C(=O)N(H)(C$_1$-C$_6$ alkyl), —C(=O)N(C$_1$-C$_6$ alkyl)$_2$, —C(=O)NH$_2$, —C(=O)OC$_1$-C$_6$ alkyl, —C(=O)OH, —N(H)C(=O)(C$_1$-C$_6$ alkyl), —N(C$_1$-C$_6$ alkyl)C(=O)(C$_1$-C$_6$ alkyl), —N(H)C(=O)OC$_1$-C$_6$ alkyl, —N(C$_1$-C$_6$ alkyl)C(=O)OC$_1$-C$_6$ (halo)alkyl, —S(O)$_{1-2}$C$_1$-C$_6$ alkyl, —N(H)S(O)$_{1-2}$C$_1$-C$_6$ alkyl, —N(C$_1$-C$_6$ alkyl)S(O)$_{1-2}$C$_1$-C$_6$ alkyl, —S(O)$_{0-1}$N(H)(C$_1$-C$_6$ alkyl), —S(O)$_{0-1}$N(C$_1$-C$_6$ alkyl)$_2$, —S(O)$_{0-1}$NH$_2$, —C(=O)C$_1$-C$_6$ alkyl, —C(=O)C$_3$-C$_7$ cycloalkyl, —C(=NOH)C$_1$-C$_6$ alkyl, —C(=NOC$_1$-C$_6$ alkyl)C$_1$-C$_6$ alkyl, —NHC(=O)N(H)(C$_1$-C$_6$ alkyl), —NHC(=O)N(C$_1$-C$_6$ alkyl)$_2$, —NHC(=O)NH$_2$, —N(C$_1$-C$_6$ alkyl)C(=O)N(H)(C$_1$-C$_6$ alkyl), —N(C$_1$-C$_6$ alkyl)C(=O)NH$_2$, —OC(=O)C$_1$-C$_6$ alkyl, —OC(=O)OC$_1$-C$_6$ alkyl, —OP(=O)(OC$_1$-C$_6$ alkyl)$_2$, —SC(=O)OC$_1$-C$_6$ alkyl and —SC(=O)N(C$_1$-C$_6$ alkyl)$_2$, wherein any alkyl portion of R$^f$ is optionally substituted with halogen;

R$^e$ is selected from the group consisting of halogen, OH, C$_1$-C$_6$ alkyl and oxo; and R$^g$ is selected from the group consisting of C$_1$-C$_6$ alkyl and C$_3$-C$_6$ cycloalkyl wherein the C$_1$-C$_6$ alkyl and C$_3$-C$_6$ cycloalkyl of R$^g$ may be optionally substituted by C$_1$-C$_3$ alkoxy, F, OH, CN, SH, CH$_3$ or CF$_3$.

In some embodiments, Q is C, and the compound is of the formula (II):

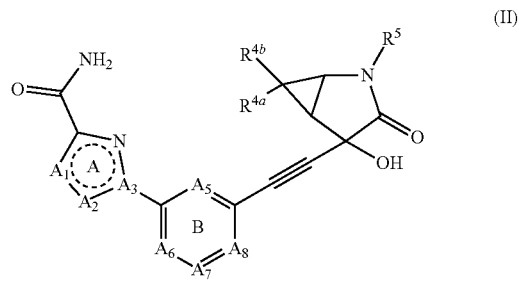

(II)

wherein ring A, A$_1$, A$_2$, A$_3$, A$_5$, A$_6$, A$_7$, A$_8$, R$^{4a}$, R$^{4b}$ and R$^5$ are as defined for formula (I).

In some embodiments, ring B is a substituted phenyl and Q is C; and the compound is of the formula (A):

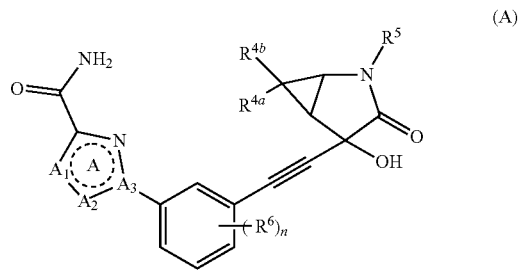

(A)

wherein ring A, A$_1$, A$_2$, A$_3$, R$^{4a}$, R$^{4b}$ and R$^5$ are as defined for formula (I), n is 0, 1 or 2, and each R$^6$ is independently selected from the group consisting of F, Cl, OCH$_3$, CH$_3$ and CF$_3$.

In one aspect, provided is a compound of formula (C):

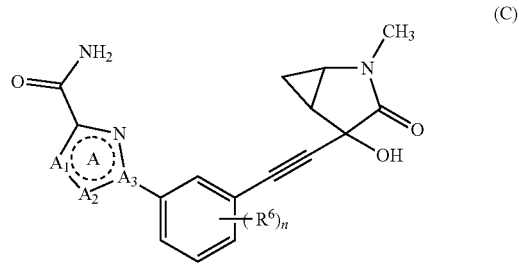

(C)

or a stereoisomer, tautomer, solvate, prodrug or salt thereof, wherein:
ring A is a monocycle or a fused bicycle;
A$_1$ is NR$^1$ or CR$^1$;
A$_2$ is NR$^2$, S or CR$^2$;
A$_3$ is N or C;
provided that no more than one of (i)-(iii) applies: (i) A$_1$ is NR$^1$, (ii) A$_2$ is NR$^2$, and (iii) A$_3$ is N;

each $R^1$ is independently —$NR^aR^b$; $C_1$-$C_3$ alkyl optionally substituted by F, OH, CN, SH or $C_1$-$C_3$ alkoxy; or taken together with $R^2$, where present, and the atoms to which they are attached to form a 6-membered heterocyclyl optionally substituted by $R^d$;

each $R^2$ is independently absent or taken together with $R^1$ and the atoms to which they are attached to form a 6-membered heterocyclyl optionally substituted by $R^d$;

n is 0 or 1;

$R^6$, where present, is halo;

each $R^a$ and $R^b$ is independently selected from the group consisting of H and $C_1$-$C_6$ alkyl; and each $R^d$ is independently selected from the group consisting of $C_1$-$C_6$ alkyl optionally substituted by halogen and $C_1$-$C_6$ alkoxy optionally substituted by halogen.

Provided is a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof described herein, or a stereoisomer, tautomer, solvate, prodrug or salt thereof. In some embodiments, provided is a compound formula (I), or any variation thereof, or a stereoisomer, tautomer, or salt thereof (e.g., a pharmaceutically acceptable salt thereof).

Also provided is a pharmaceutical composition comprising a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof, and a pharmaceutically acceptable carrier, diluent or excipient.

In another aspect, provided is a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof, or pharmaceutical compositions thereof for use in therapy.

Further provided is a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof, or pharmaceutical compositions thereof for use in the treatment of diseases and disorders, including, cancer, fibrotic condition, inflammatory conditions, and autoimmune diseases, among others.

Also provided is use of a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof, in the preparation of a medicament for the treatment of diseases and disorders, including, cancer, fibrotic condition, inflammatory conditions, and autoimmune diseases, among others.

In another aspect, provided is a method for treating a disease or disorder, for example, a cancer, a fibrotic condition, an inflammatory condition, or an autoimmune disease, in a patient, comprising administering to the patient an effective amount of a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof, or a pharmaceutical composition comprising a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof.

Further provided is a kit comprising a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof. In some embodiments, the kit comprises instructions for use according to a method described herein.

In another aspect, provided is a method of making a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof. Also provided are compound intermediates useful in synthesis of a compound of the formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), or any variation thereof.

In one aspect, a variation of a compound is a pharmaceutically acceptable salt thereof.

DETAILED DESCRIPTION OF THE INVENTION

Figure 1:
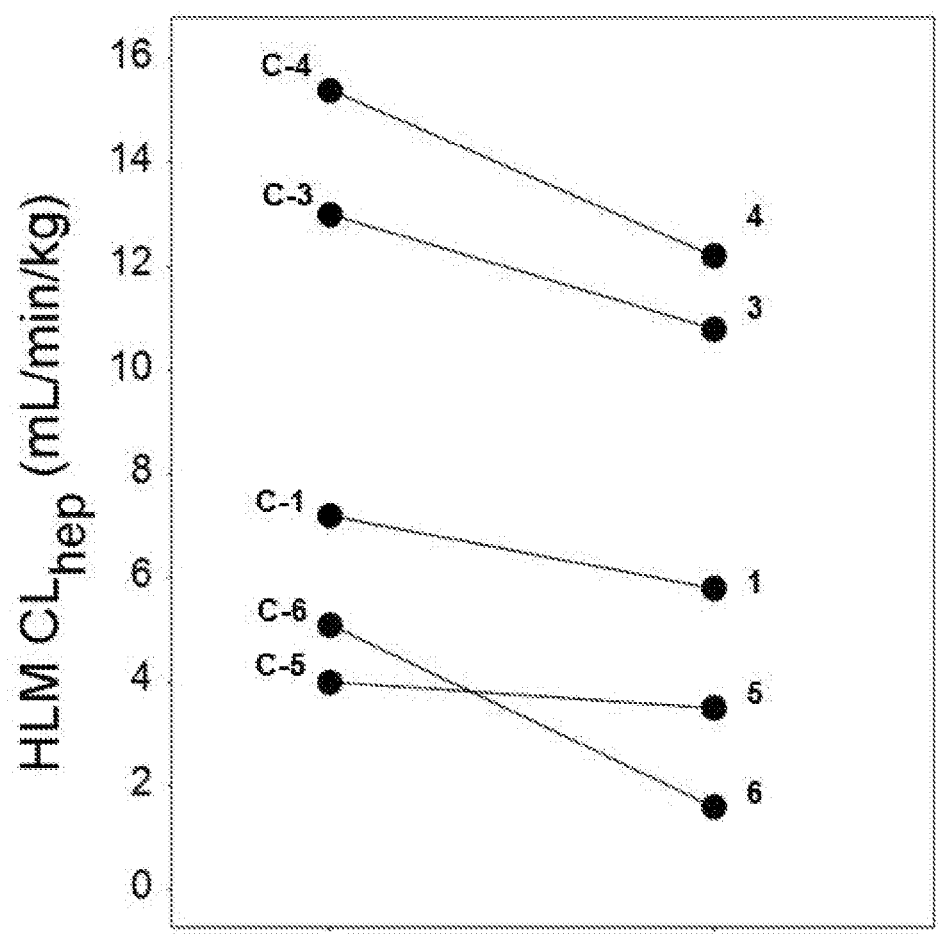
FIG. 1 shows human liver microsome clearance (in mL/min/kg) measured for the exemplary 2-azabicyclo[3.1.0]hexan-3-one compounds in comparison with that for the corresponding pyrrolidinone compounds.
Figure 1:

The invention provides, inter alia, compounds of formulae (I), and variations thereof (such as compounds of formula (II), (A), (Aa), (Aa-1), (Aa-2), (B), (Ba), (Ba-1), (Ba-2), (C), (Ca), (Ca-1), (Ca-2), (D), (Da), (Da-1) or (Da-2), pharmaceutical compositions comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), and methods of using such compounds and compositions in treating diseases and disorders related to undesired or overactivation of the NF-kB signaling pathway, such as, for example, a cancer, a fibrotic condition, an inflammatory condition, or an autoimmune disease.

Definition

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl. In some embodiments, substituents for "optionally substituted alkyls" include one to six instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperazinyl, or pyrimidinyl, wherein the alkyl, aryl and heterocyclic portions thereof may be optionally substituted.

The term "alkylene" by itself or as part of another substituent means a divalent radical derived from an alkane, as exemplified by —$CH_2CH_2CH_2CH_2$—. Typically, an alkyl (or alkylene) group will have from 1 to 12 carbon atoms, such as 1-8, 1-6 or 1-3 carbon atoms. "Alkenylene" and "alkynylene" refer to the unsaturated forms of "alkylene" having double or triple bonds, respectively, and typically have from 2 to 12 carbon atoms, such as 2-8, 2-6 or 2-3 carbon atoms. "Alkylene", "alkenylene" and "alkynylene" groups may be optionally substituted.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—$CH_2$—$CH_3$). Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S($O)_2$—$CH_3$, —Si($CH_3)_3$, —$CH_2$—CH=N—$OCH_3$, and —$OCF_3$. Up to two heteroatoms can be consecutive, such as, for example, —$CH_2$—NH—$OCH_3$ and —$CH_2$—O—Si($CH_3)_3$. Heteroalkyl groups can be optionally substituted. In some embodiments, substituents for "optionally substituted heteroalkyls" include one to four instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperazinyl, and pyrimidinyl, wherein the alkyl, aryl and heterocyclic portions thereof may be optionally substituted.

The term "heteroalkylene" means a divalent radical derived from heteroalkyl, as exemplified by —$CH_2CH_2SCH_2CH_2$—, —$CH_2SCH_2CH_2NHCH_3$ and —$OCH_2CH_3$. For heteroalkylene groups, heteroatoms can also occupy either or both of the chain termini (e.g., alkyleneoxy, alkylenedioxy, alkyleneamino, alkylenediamino, and the like). A heteroalkylene group may be optionally substituted.

"Cycloalkyl" refers to a non-aromatic, saturated or partially unsaturated hydrocarbon ring group wherein the cycloalkyl group may be optionally substituted with one or more substituents described herein. In one example, the cycloalkyl group is 3 to 12 carbon atoms ($C_3$-$C_{12}$). In other examples, cycloalkyl is $C_3$-$C_6$, $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[4.1.0]heptane, bicycle[3.1.1]heptane, bicyclo[2.2.1]heptane, bicyclo[2.2.2]octane, bicyclo[4.1.0]heptane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperazinyl, and pyrimidinyl, wherein the alkyl, aryl and heterocyclic portions thereof may be optionally substituted.

The term "cycloalkylene" means a divalent radical derived from a cycloalkyl group. A cycloalkylene group may be optionally substituted.

"Heterocyclic group", "heterocyclic", "heterocycle", "heterocyclyl", or "heterocyclo" are used interchangeably and refer to any monocyclic, bicyclic, or spiro, saturated or unsaturated, aromatic (heteroaryl) or non-aromatic (e.g., heterocycloalkyl), ring system, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members", that is, a 3-11 membered heterocycle) and includes monocycles, bicycles, and spiro ring systems, wherein the ring atoms are carbon, and at least one atom in the ring or ring system is a heteroatom selected from nitrogen, sulfur or oxygen. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6-membered monocycles. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). In another example, heterocyclyl includes 3- to 9-membered spiro cycles having one or more heteroatoms selected from nitrogen, sulfur or oxygen. Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to six instances of F, $C_1$, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperazinyl, and pyrimidinyl, wherein the alkyl, aryl and heterocyclic portions thereof may be optionally substituted.

The term "heterocyclylene" means a divalent radical derived from a heterocyclyl group. A heterocyclylene group may be optionally substituted.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13th ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 4-6 membered monocyclic aromatic groups where one or more ring atoms is nitrogen, sulfur or oxygen. In another embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazo[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to six instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperazinyl, and pyrimidinyl, wherein the alkyl, aryl and heterocyclic portions thereof may be optionally substituted.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or O-carboline.

The term "alkoxy" refers to those alkyl groups attached to the remainder of the molecule via an oxygen atom. Non-limiting examples include methoxy, ethoxy and propoxy. Alkoxy groups may be optionally substituted, such as by halogen.

The term "alkylthio" refers to those alkyl groups attached to the remainder of the molecule via a sulfur atom. Non-limiting examples include —$SCH_3$, —$SCH_2CH_3$ and —$SCH_2CH_2CH_3$. Alkylthio groups may be optionally substituted, such as by halogen.

The terms "halo" or "halogen," by themselves or as part of another substituent, mean, unless otherwise stated, a fluorine, chlorine, bromine, or iodine atom. The term "haloalkyl" is meant to include both an "alkyl" and a "haloalkyl" substituent. Additionally, the term "haloalkyl," is meant to include monohaloalkyl and polyhaloalkyl.

The term "oxo" refers to =O or $(=O)_2$.

The term "aryl" means, unless otherwise stated, a polyunsaturated, typically aromatic, hydrocarbon ring radical, which can be a single ring or multiple rings (up to three rings) which are fused together and having the stated number of aryl ring atoms. An aryl group can be optionally substituted.

A "phenylene" group refers to a divalent radical derived from a phenyl group. A phenylene group may be optionally substituted.

"Optionally substituted" unless otherwise specified means that a group may be unsubstituted or substituted by one or more (e.g., 0, 1, 2, 3, 4, or 5 or more) of the substituents listed for that group in which said substituents may be the same or different. That is, an optionally substituted substituent is independent at each occurrence. In an embodiment an optionally substituted group has 1 substituent. In another embodiment an optionally substituted group has 2 substituents. In another embodiment an optionally substituted group has 3 substituents. In another embodiment an optionally substituted group has 4 substituents.

Optional substituents for alkyl and cycloalkyl can be a variety of groups including, but not limited to, halogen, oxo, CN, $NO_2$, $N_3$, OR', perfluoro-$C_{1-4}$ alkoxy, unsubstituted cycloalkyl, unsubstituted aryl (e.g., phenyl), unsubstituted heterocyclyl, NR'R", SR', SiR'R"R'", OC(O)R', C(O)R', $CO_2$R', CONR'R", OC(O)NR'R", NR"C(O)R', NR"'C(O)NR'R", NR"C(O)$_2$R', S(O)$_2$R', S(O)$_2$NR'R", NR'S(O)$_2$R", NR'"S(O)$_2$NR'R", amidino, guanidine, $(CH_2)_{1-4}$OR', $(CH_2)_{1-4}$NR'R", $(CH_2)_{1-4}$SR', $(CH_2)_{1-4}$SiR'R"R'", $(CH_2)_{1-4}$OC(O)R', $(CH_2)_{1-4}$C(O)R', $(CH_2)_{1-4}$CO$_2$R', and $(CH_2)_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted $C_{1-6}$ alkyl; unsubstituted heteroalkyl; unsubstituted aryl; aryl substituted with 1-3 halogens, unsubstituted $C_1$-$C_6$ alkyl, $C_1$-$C_6$ alkoxy or $C_1$-$C_6$ thioalkoxy groups, unsubstituted aryl-$C_1$-$C_4$ alkyl groups, and unsubstituted heteroaryl. When R' and R" are attached to the same nitrogen atom, they can be combined with the nitrogen atom to form a 3-, 4-, 5-, 6-, or 7-membered ring wherein a ring atom is optionally substituted with N, O or S. For example, NR'R" is meant to include 1-pyrrolidinyl and 4-morpholinyl.

Similarly, optional substituents for the aryl and heterocyclyl groups are varied. In some embodiments, substituents for aryl and heterocyclyl groups are selected from the group including, but not limited to, halogen, OR', OC(O)R', NR'R", SR', R', CN, $NO_2$, $CO_2$R', CONR'R", C(O)R', OC(O)NR'R", NR"C(O)R', NR"C(O)$_2$R', NR'C(O)NR"R'", S(O)R', S(O)$_2$R', S(O)$_2$NR'R", NR'S(O)$_2$R", $N_3$, perfluoro-$C_1$-$C_4$ alkoxy, perfluoro-$C_1$-$C_4$ alkoxy, $(CH_2)_{1-4}$OR', $(CH_2)_{1-4}$NR'R", $(CH_2)_{1-4}$SR', $(CH_2)_{1-4}$SiR'R"R'", $(CH_2)_{1-4}$OC(O)R', $(CH_2)_{1-4}$C(O)R', $(CH_2)_{1-4}$CO$_2$R', $(CH_2)_{1-4}$CONR'R", or combinations thereof, in a number ranging from zero to the total number of open valences on the aromatic ring system; and where R', R" and R'" are independently selected from hydrogen, $C_1$-$C_6$ alkyl, $C_3$-$C_6$ cycloalkyl, $C_2$-$C_6$ alkenyl, $C_2$-$C_6$ alkynyl, unsubstituted aryl, and unsubstituted heteroaryl. Other suitable substituents include each of the above aryl substituents attached to a ring atom by an alkylene tether of from 1-4 carbon atoms.

As used herein, the term "heteroatom" is meant to include oxygen (O), nitrogen (N), sulfur (S) and silicon (Si). In some embodiments, heteroatom refers to O, N or S. In some embodiments, heteroatom refers to O or N.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended. If a discrepancy exists between a structure and its name, the structure governs.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

A "subject," "individual," or "patient" is a vertebrate. In certain embodiments, the vertebrate is a mammal. A subject, individual or patient may be in need of a compound of the present invention. In one aspect, a subject, individual or patient is a human.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", J. Pharm. Sci., 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_{1-6}$) alkyl)$_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77: 285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}$C or $^3$H) isotope of a compound of the invention, administering it in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. Compounds of the present invention may exist in multiple crystalline or amorphous forms. In general, all physical forms are intended to be within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and Examples herein, by substituting an isotopically labeled reagent for a non-isotopically labeled reagent.

One non-limiting example of an isotopically substituted moiety is the following:

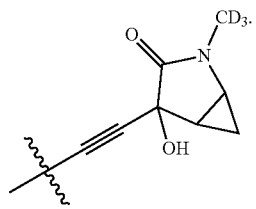 [SMILES: *C#CC1(O)C(=O)N(C([2H])([2H])[2H])C2CC21]

The terms "compound(s) of this invention," and "compound(s) of the present invention" and the like, unless otherwise indicated, include compounds of formulae (I), (II) (A), (Aa), (Aa-1), (Aa-2), (B), (Ba), (Ba-1), (Ba-2), (C), (Ca), (Ca-1), (Ca-2), (D), (Da), (Da-1) and (Da-2), and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented. In some embodiments, prophylaxis is excluded from the definition of "treatment."

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) or determining the response rate (RR). In the case of immunological disease, the therapeutically effective amount is an amount sufficient to decrease or alleviate an allergic disorder, the symptoms of an autoimmune or inflammatory condition (e.g., psoriasis or inflammatory bowel disease), or the symptoms of an acute inflammatory reaction (e.g., asthma). In some embodiments, a therapeutically effective amount is an amount of a chemical entity described herein sufficient to significantly decrease the activity or number of B-cells.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., NIK activity) compared to normal.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory condition" as used herein refers to any disease, disorder, or syndrome in which an excessive or unregulated inflammatory response leads to excessive inflammatory symptoms, host tissue damage, or loss of tissue function.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune response to foreign antigen, and autoimmune responses.

The terms "cancer" and "cancerous" refer to or describe the physiological condition in mammals that is typically characterized by unregulated cell growth or proliferation. A "tumor" comprises one or more cancerous cells. Examples of cancer include, but are not limited to, carcinoma, lymphoma, blastoma, sarcoma, and leukemia or lymphoid malignancies.

"Autoimmune disease" as used herein refers to any group of disorders in which tissue injury is associated with humoral or cell-mediated responses to the body's own constituents.

It is specifically contemplated that any limitation discussed with respect to one embodiment of the invention may apply to any other embodiment of the invention.

Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value. In one aspect, "about" includes the value per se. For example, about X includes and describes X per se.

As used herein, "a" or "an" means one or more, unless clearly indicated otherwise. As used herein, "another" means at least a second or more.

Headings used herein are intended only for organizational purposes.

Inhibitors of NIK

One aspect of the invention provides a compound of formula (I):

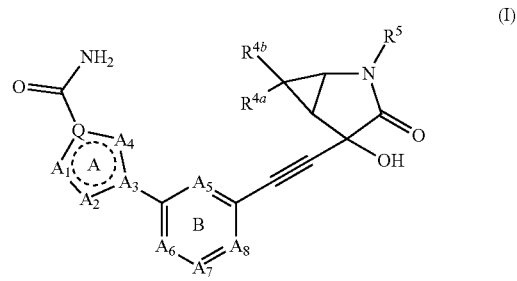

or a stereoisomer, tautomer, solvate, prodrug or salt thereof, wherein:
  ring A is a monocycle or a fused bicycle;
  Q is N or C, wherein when Q is N, then the bond between $A_1$ and Q is not a double bond and the bond between Q and $A_4$ is not a double bond;
  $A_1$ is $NR^1$, N, S, $CR^1$ or $CHR^1$;
  $A_2$ is $NR^2$, N, O, S, $CR^2$ or $CHR^2$;
  $A_3$ is N or C;
  $A_4$ is N; and
  one, two or three of $A_1$-$A_4$ are N, wherein:
    each $R^1$ is independently selected from the group consisting of H, halogen, —$NR^aR^b$, —$NHC(O)NR^aR^b$, —$NHS(O)_2$—$C_1$-$C_3$ alkyl, $C_1$-$C_3$ alkyl, $C_3$-$C_7$ cycloalkyl, $C_1$-$C_3$ alkoxy and 3-11 membered heterocyclyl, wherein the $C_1$-$C_3$ alkyl of $R^1$ is optionally substituted by F, OH, CN, SH, $C_1$-$C_3$ alkoxy or 3-11 membered heterocyclyl; the $C_3$-$C_7$ cycloalkyl of $R^1$ is optionally substituted by F, OH, CN, SH, $CH_3$ or $CF_3$; the $C_1$-$C_3$ alkoxy of $R^1$ is optionally substituted by F, OH, CN or SH; and the 3-11 membered heterocyclyl of $R^1$ is optionally substituted by F, OH, CN, SH, $CF_3$ or $C_1$-$C_3$ alkyl,
    each $R^2$ is independently selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl, wherein the $C_1$-$C_6$ alkyl, $C_3$-$C_7$ cycloalkyl, $C_1$-$C_6$ alkoxy, phenyl and 3-11 membered heterocyclyl of $R^2$ is optionally substituted by $R^c$; or
    $R^1$ and $R^2$ are taken together with the atoms to which they are attached to form a cyclic group selected from the group consisting of $C_3$-$C_7$ cycloalkyl, phenyl and 3-11 membered heterocyclyl, wherein the cyclic group is optionally substituted by $R^d$;
  each $R^{4a}$ and $R^{4b}$ is independently H or F;

$R^5$ is $C_1$-$C_6$ alkyl or $C_3$-$C_4$ cycloalkyl, wherein the $C_1$-$C_6$ alkyl and $C_3$-$C_4$ cycloalkyl of $R^5$ are independently optionally substituted by halogen, OH, or $C_1$-$C_6$ alkoxy;

each $A_5$, $A_6$, $A_7$ and $A_8$ is independently N or $CR^6$, provided that at least three of $A_5$, $A_6$, $A_7$ and $A_8$ are independently $CR^6$;

each $R^6$ is independently selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;

$R^a$ is selected from the group consisting of H and $C_1$-$C_6$ alkyl optionally substituted by $C_1$-$C_3$ alkoxy, F, OH, CN, SH, $CH_3$ or $CF_3$;

$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl wherein $R^b$ may be optionally substituted by $C_1$-$C_3$ alkoxy, F, OH, CN, SH, $CH_3$ or $CF_3$;

$R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$N(H)$(R^{1a})$, —$(X^1)_{0-1}$—N$(R^{1b})(R^{1a})$, —$(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, —$(X^1)_{0-1}$—$C_1$-$C_6$ alkyl, —$(X^1)_{0-1}$—$C_3$-$C_{10}$ cycloalkyl, —O—$C_3$-$C_{10}$ cycloalkyl, —$(X^1)_{0-1}$-3-11 membered heterocyclyl, —$(X^1)_{0-1}$—$C_6$-$C_{10}$ aryl, —C(=O)$(X^1)_{0-1}$—$C_3$-$C_{10}$ cycloalkyl, —C(=O)$(X^1)_{0-1}$-3-11 membered heterocyclyl, —$(X^1)_{0-1}$—C(=$Y^1$)N(H)$(R^{1a})$, —$(X^1)_{0-1}$—C(=$Y^1$)$NH_2$, —$(X^1)_{0-1}$—C(=$Y^1$)N$(R^{1a})(R^{1b})$, —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)$(R^{1a})$, —$(X^1)_{0-1}$—N$(R^{1b})$C(=$Y^1$)$(R^{1a})$, —$(X^1)_{0-1}$—N$(R^{1b})$C(=$Y^1$)(H), —$(X^1)_{0-1}$—N(H)C(=$Y^1$)$(R^{1a})$, N$(R^{1b})$C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N$(R^{1b})$S(O)$_{1-2}R^{1a}$, —$(X^1)_{0-1}$—S(O)$_{0-1}$N(H)$(R^{1a})$, —$(X^1)_{0-1}$—S(O)$_{0-1}$N$(R^{1b})(R^{1a})$, —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)$(R^{1a})$, —$(X^1)_{0-1}$—NHC(=$Y^1$)$NH_2$, —$(X^1)_{0-1}$—NHC(=$Y^1$)N$(R^{1b})(R^{1a})$, —$(X^1)_{0-1}$—N$(R^{1a})$C(=$Y^1$)N(H)$(R^{1a})$, —$(X^1)_{0-1}$—N$(R^{1a})$C(=$Y^1$)N$(R^{1a})(R^{1b})$, —$(X^1)_{0-1}$—N$(R^{1a})$C(=$Y^1$)$NH_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)$OR^{1a}$, —$(X^1)_{0-1}$—OP(=$Y^1$)$(OR^{1a})(OR^{1b})$, —$(X^1)_{0-1}$—SC(=$Y^1$)$OR^{1a}$ and —$(X^1)$—SC(=$Y^1$)N$(R^{1a})(R^{1b})$; wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl, (3-11 membered heterocyclylene)$C_1$-$C_6$ alkyl, phenyl, and ($C_6$-$C_{10}$ arylene)$C_1$-$C_6$ alkyl, or $R^{1a}$ and $R^{1b}$, when attached to the same nitrogen atom, are taken together with the nitrogen to which they are attached to form a 3-11 membered heterocyclyl comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is independently further substituted by from 0 to 4 $R^f$ substituents selected from the group consisting of halogen, CN, $NO_2$, $SF_5$, OH, $NH_2$, —N$(C_1$-$C_6$ alkyl$)_2$, —NH$(C_1$-$C_6$ alkyl), oxo, $C_1$-$C_6$ alkyl, —$(C_2$-$C_6$ alkynylene)-(3-11 membered heterocyclyl, wherein the heterocyclyl is optionally substituted by $R^e$), $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl, —C(=O)N(H)$(C_1$-$C_6$ alkyl), —C(=O)N$(C_1$-$C_6$ alkyl$)_2$, —C(=O)$NH_2$, —C(=O)O$C_1$-$C_6$ alkyl, —C(=O)OH, —N(H)C(=O)$(C_1$-$C_6$ alkyl), —N$(C_1$-$C_6$ alkyl)C(=O)$(C_1$-$C_6$ alkyl), —N(H)C(=O)O$C_1$-$C_6$ alkyl, —N$(C_1$-$C_6$ alkyl)C(=O)O$C_1$-$C_6$ (halo)alkyl, —S(O)$_{1-2}C_1$-$C_6$ alkyl, —N(H)S(O)$_{1-2}C_1$-$C_6$ alkyl, —N$(C_1$-$C_6$ alkyl)S(O)$_{1-2}C_1$-$C_6$ alkyl, —S(O)$_{0-1}$N(H)$(C_1$-$C_6$ alkyl), —S(O)$_{0-1}$N$(C_1$-$C_6$ alkyl$)_2$, —S(O)$_{0-1}NH_2$, —C(=O)$C_1$-$C_6$ alkyl, —C(=O)$C_3$-$C_7$ cycloalkyl, —C(=NOH)$C_1$-$C_6$ alkyl, —C(=NO$C_1$-$C_6$ alkyl)$C_1$-$C_6$ alkyl, —NHC(=O)N(H)$(C_1$-$C_6$ alkyl), —NHC(=O)N$(C_1$-$C_6$ alkyl$)_2$, —NHC(=O)$NH_2$, —N$(C_1$-$C_6$ alkyl)C(=O)N(H)$(C_1$-$C_6$ alkyl), —N$(C_1$-$C_6$ alkyl)C(=O)$NH_2$, —OC(=O)$C_1$-$C_6$ alkyl, —OC(=O)O$C_1$-$C_6$ alkyl, —OP(=O)$(OC_1$-$C_6$ alkyl$)_2$, —SC(=O)O$C_1$-$C_6$ alkyl and —SC(=O)N$(C_1$-$C_6$ alkyl$)_2$, wherein any alkyl portion of $R^f$ is optionally substituted with halogen;

$R^e$ is selected from the group consisting of halogen, OH, $C_1$-$C_6$ alkyl and oxo; and $R^g$ is selected from the group consisting of $C_1$-$C_6$ alkyl and $C_3$-$C_6$ cycloalkyl wherein the $C_1$-$C_6$ alkyl and $C_3$-$C_6$ cycloalkyl of $R^g$ may be optionally substituted by $C_1$-$C_3$ alkoxy, F, OH, CN, SH, $CH_3$ or $CF_3$.

In some embodiments, the compound is of the formula (I), provided that no more than two of (i)-(iii) apply: (i) $A_1$ is $NR^1$ or N, (ii) $A_2$ is $NR^2$ or N, and (iii) $A_3$ is N. In some embodiments, the compound is of the formula (I), provided at least one of (iv)-(vi) applies: (iv) $A_1$ is S, $CR^1$ or $CHR^1$; (v) $A_2$ is O, S, $CR^2$ or $CHR^2$; and (vi) $A_3$ is C.

In some embodiments, ring A is an unsaturated monocycle or an unsaturated fused bicycle.

In some embodiments, a compound of formula (I) is further defined as a compound of formula (II):

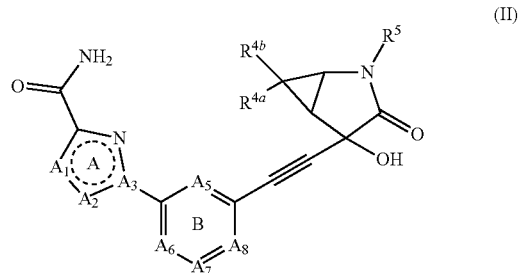

or a stereoisomer, tautomer, solvate, prodrug or salt thereof, wherein:

ring A is a monocycle or a fused bicycle;

$A_1$ is $NR^1$, N, S, $CR^1$ or $CHR^1$;

$A_2$ is $NR^2$, N, O, S, $CR^2$ or $CHR^2$;

$A_3$ is N or C;

each $R^1$ is independently selected from the group consisting of H, halogen, —$NR^aR^b$, —NHC(O)$NR^aR^b$, —NHS(O)$_2$—$C_1$-$C_3$ alkyl, $C_1$-$C_3$ alkyl, $C_3$-$C_7$ cycloalkyl, $C_1$-$C_3$ alkoxy and 3-11 membered heterocyclyl, wherein the $C_1$-$C_3$ alkyl of $R^1$ is optionally substituted by F, OH, CN, SH, $C_1$-$C_3$ alkoxy or 3-11 membered heterocyclyl; the $C_3$-$C_7$ cycloalkyl of $R^1$ is optionally substituted by F, OH, CN, SH, $CH_3$ or $CF_3$; the $C_1$-$C_3$ alkoxy of $R^1$ is optionally substituted by F, OH, CN or SH; and the 3-11 membered heterocyclyl of $R^1$ is optionally substituted by F, OH, CN, SH, $CF_3$ or $C_1$-$C_3$ alkyl, each $R^2$ is independently selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl, wherein the $C_1$-$C_6$ alkyl, $C_3$-$C_7$ cycloalkyl, $C_1$-$C_6$ alkoxy, phenyl and 3-11 membered heterocyclyl of $R^2$ is optionally substituted by $R^c$; or $R^1$ and $R^2$ are taken together with the atoms to which they are attached to form a cyclic group selected from the group consisting of $C_3$-$C_7$ cycloalkyl, phenyl and 3-11 membered heterocyclyl, wherein the cyclic group is optionally substituted by $R^d$;

each $R^{4a}$ and $R^{4b}$ is independently H or F;

$R^5$ is $C_1$-$C_6$ alkyl or $C_3$-$C_4$ cycloalkyl, wherein the $C_1$-$C_6$ alkyl and $C_3$-$C_4$ cycloalkyl of $R^5$ are independently optionally substituted by halogen, OH, or $C_1$-$C_6$ alkoxy;

each $A_5$, $A_6$, $A_7$ and $A_8$ is independently N or $CR^6$, provided that at least three of $A_5$, $A_6$, $A_7$ and $A_8$ are independently $CR^6$;

each $R^6$ is independently selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;

$R^a$ is selected from the group consisting of H and $C_1$-$C_6$ alkyl optionally substituted by $C_1$-$C_3$ alkoxy, F, OH, CN, SH, $CH_3$ or $CF_3$;

$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl wherein $R^b$ may be optionally substituted by $C_1$-$C_3$ alkoxy, F, OH, CN, SH, $CH_3$ or $CF_3$;

$R^c$ and $R^d$ are each independently selected from the group consisting of halogen, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, $-(X^1)_{0-1}-C_1$-$C_6$ alkyl, $-(X^1)_{0-1}-C_3$-$C_{10}$ cycloalkyl, $-O-C_3$-$C_{10}$ cycloalkyl, $-(X^1)_{0-1}$-3-11 membered heterocyclyl, $-(X^1)_{0-1}-C_6$-$C_{10}$ aryl, $-C(=O)(X^1)_{0-1}-C_3$-$C_{10}$ cycloalkyl, $-C(=O)(X^1)_{0-1}$-3-11 membered heterocyclyl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})(=Y^1)(R^{1a})$, $-(X^1)_{0-1}-N(R^{1b})C(=Y)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{1-2}R^{1a}$, $-(X^1)_{0-1}-S(O)_{0-1}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y)N(R^{1b})(R^{1a})$, $-(X^1)_{0-1}-N(R^{1a})C(=Y^1)N(H)(R^{1a})$, $-(X^1)_{0-1}-N(R^{1a})C(=Y^1)N(R^{1a})(R^{1b})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^1a$ and $-(X^1)-SC(=Y^1)N(R^{1a})(R^{1b})$; wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phleylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl, (3-11 membered heterocyclylene)$C_1$-$C_6$ alkyl, phenyl, and ($C_6$-$C_{10}$ arylene)$C_1$-$C_6$ alkyl, or $R^{1a}$ and $R^{1b}$, when attached to the same nitrogen atom, are taken together with the nitrogen to which they are attached to form a 3-11 membered heterocyclyl comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is independently further substituted by from 0 to 4 $R^f$ substituents selected from the group consisting of halogen, CN, $NO_2$, $SF_5$, OH, $NH_2$, $-N(C_1$-$C_6$ alkyl$)_2$, $-NH(C_1$-$C_6$ alkyl), oxo, $C_1$-$C_6$ alkyl, $-(C_2$-$C_6$ alkynylene)-(3-11 membered heterocyclyl, wherein the heterocyclyl is optionally substituted by $R^e$), $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl, $-C(=O)N(H)(C_1$-$C_6$ alkyl), $-C(=O)N(C_1$-$C_6$ alkyl$)_2$, $-C(=O)NH_2$, $-C(=O)OC_1$-$C_6$ alkyl, $-C(=O)OH$, $-N(H)C(=O)(C_1$-$C_6$ alkyl), $-N(C_1$-$C_6$ alkyl)C(=O)(C_1$-$C_6$ alkyl), $-N(H)C(=O)OC_1$-$C_6$ alkyl, $-N(C_1$-$C_6$ alkyl)C(=O)OC_1$-$C_6$ (halo)alkyl, $-S(O)_{1-2}C_1$-$C_6$ alkyl, $-N(H)S(O)_{1-2}C_1$-$C_6$ alkyl, $-N(C_1$-$C_6$ alkyl)S(O)_{1-2}C_1$-$C_6$ alkyl, $-S(O)_{0-1}N(H)(C_1$-$C_6$ alkyl), $-S(O)_{0-1}N(C_1$-$C_6$ alkyl$)_2$, $-S(O)_{0-1}NH_2$, $-C(=O)C_1$-$C_6$ alkyl, $-C(=O)C_3$-$C_7$ cycloalkyl, $-C(=NOH)C_1$-$C_6$ alkyl, $-C(=NOC_1$-$C_6$ alkyl)$C_1$-$C_6$ alkyl, $-NHC(=O)N(H)(C_1$-$C_6$ alkyl), $-NHC(=O)N(C_1$-$C_6$ alkyl$)_2$, $-NHC(=O)NH_2$, $-N(C_1$-$C_6$ alkyl)C(=O)N(H)(C_1$-$C_6$ alkyl), $-N(C_1$-$C_6$ alkyl)C(=O)NH_2$, $-OC(=O)C_1$-$C_6$ alkyl, $-OC(=O)OC_1$-$C_6$ alkyl, $-OP(=O)(OC_1$-$C_6$ alkyl$)_2$, $-SC(=O)OC_1$-$C_6$ alkyl and $-SC(=O)N(C_1$-$C_6$ alkyl$)_2$, wherein any alkyl portion of R' is optionally substituted with halogen;

$R^e$ is selected from the group consisting of halogen, OH, $C_1$-$C_6$ alkyl and oxo; and $R^g$ is selected from the group consisting of $C_1$-$C_6$ alkyl and $C_3$-$C_6$ cycloalkyl wherein the $C_1$-$C_6$ alkyl and $C_3$-$C_6$ cycloalkyl of $R^g$ may be optionally substituted by $C_1$-$C_3$ alkoxy, F, OH, CN, SH, $CH_3$ or $CF_3$.

In some embodiments, the compound is of the formula (II), provided that no more than two of (i)-(iii) apply: (i) $A_1$ is $NR^1$ or N, (ii) $A_2$ is $NR^2$ or N, and (iii) $A_3$ is N. In some embodiments, the compound is of the formula (II), provided at least one of (iv)-(vi) applies: (iv) $A_1$ is S, $CR^1$ or $CHR^1$; (v) $A_2$ is O, S, $CR^2$ or $CHR^2$; and (vi) $A_3$ is C.

In some embodiments, ring A is an unsaturated monocycle or an unsaturated fused bicycle.

In some embodiments of the compounds of formula (I) or (II), ring A is a monocycle.

In some embodiments, ring A is a monocyclic heteroaryl containing one or two ring nitrogen atoms (e.g., a thiazole or imidazole). In some embodiments, $A_1$ is N or $CHR^1$. In some embodiments, $A_1$ is N. In some embodiments, $A_1$ is N, $A_2$ is S and $A_3$ is C (ring A is a thiadiazole). In some embodiments, $A_2$ is N, O or $CHR^2$. In some embodiments, $A_2$ is N. In some embodiments, $A_1$ is S, $A_2$ is N and $A_3$ is C (ring A is a thiadiazole). In some embodiments, $A_1$ is $CR^1$, $A_2$ is O and $A_3$ is C (ring A is an oxazole). In some embodiments, $A_1$ is $CR^1$, $A_2$ is S and $A_3$ is C (ring A is a thiazole). In some embodiments, $A_1$ is $CR^1$, $A_2$ is $NR^2$ and $A_3$ is C (ring A is an imidazole).

In some embodiments of the compounds of formula (I) or (II), $A_1$ is $CHR^1$ and $A_2$ is $CHR^2$, and ring A is a non-aromatic heterocycle. In some embodiments, $A_1$ is $CHR^1$ and $A_2$ is $CHR^2$, and ring A is a non-aromatic monocyclic heterocycle. In some embodiments, $A_1$ is $CHR^1$ and $A_2$ is $CHR^2$, and ring A is a fused bicyclic non-aromatic heterocycle. In some embodiments, $A_1$ is $CHR^1$; $A_2$ is $CHR^2$; and $R^1$ and $R^2$ are taken together with the atoms to which they are attached to form a $C_3$-$C_7$ cycloalkyl optionally substituted by $R^d$ or a 3-11 membered heterocyclyl optionally substituted by $R^d$. In some embodiments, $R^1$ and $R^2$ together form the following cyclic group, wherein the asterisks indicate the points of ring fusion to ring A, and each cyclic group is optionally substituted by $R^d$:

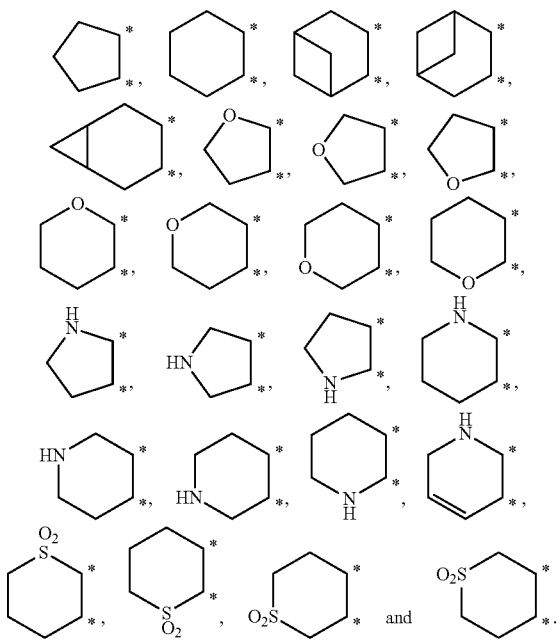

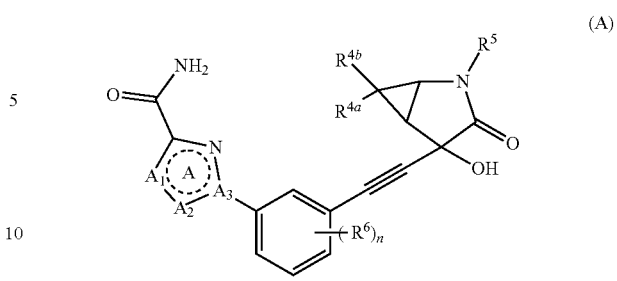

In some embodiments of the compounds of formula (I) or (II), $A_1$ is $NR^1$, S or $CR^1$; and $A_2$ is $NR^2$, S or $CR^2$. In some embodiments, $A_1$ is S. In some embodiments, $A_1$ is S, $A_2$ is $CR^2$ and $A_3$ is C. In some embodiments, $R^2$ is H.

In some embodiments of the compounds of formula (I) or (II), $A_7$ is $CR^6$ where $R^6$ is H. In some embodiments, $A_8$ is $CR^6$ where $R^6$ is H or F. In some embodiments, $A_5$ is $CR^6$ where $R^6$ is H. In some embodiments, $A_6$ is $CR^6$ where $R^6$ is selected from the group consisting of H, F, $OCH_3$ and $CH_3$. In some embodiments, ring B is phenyl (i.e., each $A_5$-$A_8$ is independently $CR^6$). In some embodiments, each $A_5$-$A_8$ is CH.

In some embodiments of the compounds of formula (I) or (II), each $R^{4a}$ and $R^{4b}$ is independently H or F; and $R^5$ is $C_1$-$C_6$ alkyl optionally substituted by halogen, OH, or $C_1$-$C_6$ alkoxy or $C_3$-$C_4$ cycloalkyl optionally substituted by halogen, OH, or $C_1$-$C_6$ alkoxy. In some embodiments, each $R^{4a}$ and $R^{4b}$ is H. In some embodiments, each $R^{4a}$ and $R^{4b}$ is F. In some embodiments, $R^5$ is $C_1$-$C_6$ alkyl optionally substituted by halogen, OH, or $C_1$-$C_6$ alkoxy. In some embodiments, $R^5$ is $C_3$-$C_4$ cycloalkyl optionally substituted by halogen, OH, or $C_1$-$C_6$ alkoxy. In some embodiments, $R^5$ is $C_1$-$C_6$ alkyl. In some embodiments, $R^5$ is $C_1$-$C_3$ alkyl (e.g., methyl).

It is intended and understood that each and every variation of $A_1$-$A_4$, including variations of $R^1$ and $R^2$ where applicable, described for formula (I) or (II) may be combined with each and every variation of $A_5$-$A_8$ described for formula (I) or (II), and with each and every variation of $R^{4a}$, $R^{4b}$ and $R^5$ described for Formula (I) or (II) or any variation described herein as if each and every combination is individually described. For example, in some embodiments of the compounds of formula (I) or (II), or a stereoisomer, tautomer, solvate, prodrug or salt thereof, ring A is a thiazole (e.g., $A_1$ is $CR^1$, $A_2$ is S, $A_3$ is C and $A_4$ is N); ring B is phenyl (e.g., each $A_5$-$A_8$ is CH); each $R^{4a}$ and $R^{4b}$ is H; and $R^5$ is methyl.

In some embodiments, a compound of formula (I) is further defined as a compound of formula (A):

or a stereoisomer, tautomer, solvate, prodrug or salt thereof, wherein:
ring A is a monocycle or a fused bicycle;
$A_1$ is $NR^1$ or $CR^1$;
$A_2$ is $NR^2$, S or $CR^2$;
$A_3$ is N or C;
each $R^1$ is independently selected from the group consisting of H, halogen, $-NR^aR^b$, $-NHC(O)NR^aR^b$, $-NHS(O)_2-C_1$-$C_3$ alkyl, $C_1$-$C_3$ alkyl, $C_3$-$C_7$ cycloalkyl, $C_1$-$C_3$ alkoxy and 3-11 membered heterocyclyl, wherein the $C_1$-$C_3$ alkyl of $R^1$ is optionally substituted by F, OH, CN, SH, $C_1$-$C_3$ alkoxy or 3-11 membered heterocyclyl; the $C_3$-$C_7$ cycloalkyl of $R^1$ is optionally substituted by F, OH, CN, SH, $CH_3$ or $CF_3$; the $C_1$-$C_3$ alkoxy of $R^1$ is optionally substituted by F, OH, CN or SH; and the 3-11 membered heterocyclyl of $R^1$ is optionally substituted by F, OH, CN, SH, $CF_3$ or $C_1$-$C_3$ alkyl,
each $R^2$ is independently selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl, wherein the $C_1$-$C_6$ alkyl, $C_3$-$C_7$ cycloalkyl, $C_1$-$C_6$ alkoxy, phenyl and 3-11 membered heterocyclyl of $R^2$ is optionally substituted by $R^c$; or
$R^1$ and $R^2$ are taken together with the atoms to which they are attached to form a cyclic group selected from the group consisting of $C_3$-$C_7$ cycloalkyl, phenyl and 3-11 membered heterocyclyl, wherein the cyclic group is optionally substituted by $R^d$;
each $R^{4a}$ and $R^{4b}$ is independently H or F;
$R^5$ is $C_1$-$C_6$ alkyl or $C_3$-$C_4$ cycloalkyl, wherein the $C_1$-$C_6$ alkyl and $C_3$-$C_4$ cycloalkyl of $R^5$ are independently optionally substituted by halogen, OH, or $C_1$-$C_6$ alkoxy;
n is 0, 1, 2, 3 or 4;
each $R^6$ is independently selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;
$R^a$ is selected from the group consisting of H and $C_1$-$C_6$ alkyl optionally substituted by $C_1$-$C_3$ alkoxy, F, OH, CN, SH, $CH_3$ or $CF_3$;
$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl wherein $R^b$ may be optionally substituted by $C_1$-$C_3$ alkoxy, F, OH, CN, SH, $CH_3$ or $CF_3$;
$R^c$ and $R^d$ are each independently selected from the group consisting of halogen, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, $-(X^1)_{0-1}-C_1$-$C_6$ alkyl, $-(X^1)_{0-1}-C_3$-$C_{10}$ cycloalkyl, $-O-C_3$-$C_{10}$ cycloalkyl, $-(X^1)_{0-1}$-3-11 membered heterocyclyl, $-(X^1)_{0-1}-C_6$-$C_{10}$ aryl, $-C(=O)(X^1)_{0-1}-C_3$-$C_{10}$ cycloalkyl, $-C(=O)(X^1)_{0-1}$-3-11 membered heterocyclyl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), (X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^b$)C(=Y$^1$)(R$^{1a}$), —(X$^1$)$_{0-1}$—N(R$^{1b}$)$_{0-1}$—C(=Y)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1b}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$); wherein X$^1$ is selected from the group consisting of C$_1$-C$_6$ alkylene, C$_1$-C$_6$ heteroalkylene, C$_2$-C$_6$ alkenylene, C$_2$-C$_6$ alkynylene, C$_1$-C$_6$ alkyleneoxy, C$_3$-C$_7$ cycloalkylene, 3-11 membered heterocyclylene and phenylene; R$^{1a}$ and R$^{1b}$ are each independently selected from the group consisting of C$_1$-C$_6$ alkyl, C$_1$-C$_6$ haloalkyl, C$_1$-C$_6$ heteroalkyl, C$_3$-C$_7$ cycloalkyl, (C$_3$-C$_7$ cycloalkylene)C$_1$-C$_6$ alkyl, 3-11 membered heterocyclyl, (3-11 membered heterocyclylene)C$_1$-C$_6$ alkyl, phenyl, and (C$_6$-C$_{10}$ arylene)C$_1$-C$_6$ alkyl, or R$^{1a}$ and R$^{1b}$, when attached to the same nitrogen atom, are taken together with the nitrogen to which they are attached to form a 3-11 membered heterocyclyl comprising 0-3 additional heteroatoms selected from N, O and S; Y$^1$ is O, NR$^{1c}$ or S wherein R$^{1c}$ is H or C$_1$-C$_6$ alkyl; wherein any portion of an R$^c$ or R$^d$ substituent, including R$^{1a}$, R$^{1b}$ and R$^{1c}$, at each occurrence is independently further substituted by from 0 to 4 R$^f$ substituents selected from the group consisting of halogen, CN, NO$_2$, SF$_5$, OH, NH$_2$, —N(C$_1$-C$_6$ alkyl)$_2$, —NH(C$_1$-C$_6$ alkyl), oxo, C$_1$-C$_6$ alkyl, —(C$_2$-C$_6$ alkynylene)-(3-11 membered heterocyclyl, wherein the heterocyclyl is optionally substituted by R$^e$), C$_1$-C$_6$ hydroxyalkyl, C$_1$-C$_6$ heteroalkyl, C$_1$-C$_6$ alkoxy, C$_1$-C$_6$ alkylthio, C$_3$-C$_7$ cycloalkyl, 3-11 membered heterocyclyl, —C(=O)N(H)(C$_1$-C$_6$ alkyl), —C(=O)N(C$_1$-C$_6$ alkyl)$_2$, —C(=O)NH$_2$, —C(=O)OC$_1$-C$_6$ alkyl, —C(=O)OH, —N(H)C(=O)(C$_1$-C$_6$ alkyl), —N(C$_1$-C$_6$ alkyl)C(=O)(C$_1$-C$_6$ alkyl), —N(H)C(=O)OC$_1$-C$_6$ alkyl, —N(C$_1$-C$_6$ alkyl)C(=O)OC$_1$-C$_6$ (halo)alkyl, —S(O)$_{1-2}$C$_1$-C$_6$ alkyl, —N(H)S(O)$_{1-2}$C$_1$-C$_6$ alkyl, —N(C$_1$-C$_6$ alkyl)S(O)$_{1-2}$C$_1$-C$_6$ alkyl, —S(O)$_{0-1}$N(H)(C$_1$-C$_6$ alkyl), —S(O)$_{0-1}$N(C$_1$-C$_6$ alkyl)$_2$, —S(O)$_{0-1}$NH$_2$, —C(=O)C$_1$-C$_6$ alkyl, —C(=O)C$_3$-C$_7$ cycloalkyl, —C(=NOH)C$_1$-C$_6$ alkyl, —C(=NOC$_1$-C$_6$ alkyl)C$_1$-C$_6$ alkyl, —NHC(=O)N(H)(C$_1$-C$_6$ alkyl), —NHC(=O)N(C$_1$-C$_6$ alkyl)$_2$, —NHC(=O)NH$_2$, —N(C$_1$-C$_6$ alkyl)C(=O)N(H)(C$_1$-C$_6$ alkyl), —N(C$_1$-C$_6$ alkyl)C(=O)NH$_2$, —OC(=O)C$_1$-C$_6$ alkyl, —OC(=O)OC$_1$-C$_6$ alkyl, —OP(=O)(OC$_1$-C$_6$ alkyl)$_2$, —SC(=O)OC$_1$-C$_6$ alkyl and —SC(=O)N(C$_1$-C$_6$ alkyl)$_2$, wherein any alkyl portion of R$^f$ is optionally substituted with halogen;

R$^e$ is selected from the group consisting of halogen, OH, C$_1$-C$_6$ alkyl and oxo; and R$^g$ is selected from the group consisting of C$_1$-C$_6$ alkyl and C$_3$-C$_6$ cycloalkyl wherein the C$_1$-C$_6$ alkyl and C$_3$-C$_6$ cycloalkyl of R$^g$ may be optionally substituted by C$_1$-C$_3$ alkoxy, F, OH, CN, SH, CH$_3$ or CF$_3$.

In some embodiments, the compound is of the formula (A), provided that no more than two of (i)-(iii) apply: (i) A$_1$ is NR$^1$; (ii) A$_2$ is NR$^2$; and (iii) A$_3$ is N. In some embodiments, the compound is of the formula (A), provided at least one of (iv)-(vi) apply: (iv) A$_1$ is CR$^1$; (v) A$_2$ is S or CR$^2$; and (vi) A$_3$ is C.

In some embodiments, ring A is an unsaturated monocycle or an unsaturated fused bicycle.

In some embodiments, a compound of formula (A) is further defined as a compound of formula (Aa):

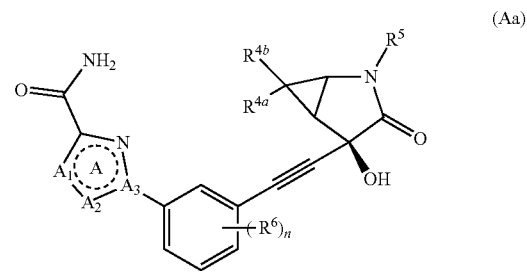

or a stereoisomer, tautomer, solvate, prodrug or salt thereof, wherein A$_1$, A$_2$, A$_3$, R$^{4a}$, R$^{4b}$, R$^5$, R$^6$ and n are as defined for formula (A), or any variation thereof.

In some embodiments, a compound of formula (A) is further defined as a compound of formula (Aa-1):

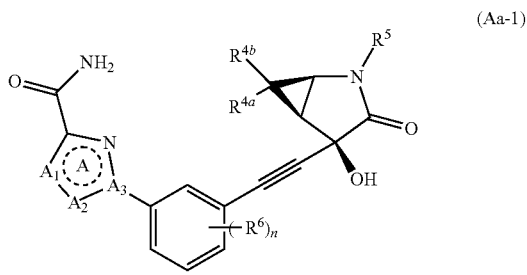

or a stereoisomer, tautomer, solvate, prodrug or salt thereof, wherein A$_1$, A$_2$, A$_3$, R$^{4a}$, R$^{4b}$, R$^5$, R$^6$ and n are as defined for formula (A), or any variation thereof.

In some embodiments, a compound of formula (A) is further defined as a compound of formula (Aa-2):

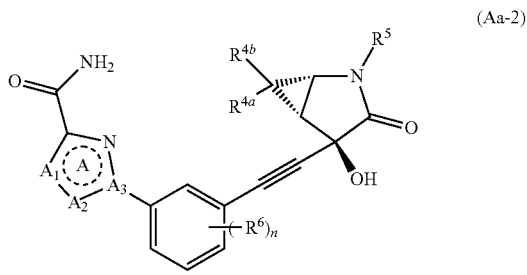

or a stereoisomer, tautomer, solvate, prodrug or salt thereof, wherein A$_1$, A$_2$, A$_3$, R$^{4a}$, R$^{4b}$, R$^5$, R$^6$ and n are as defined for formula (A), or any variation thereof.

In some embodiments, a compound of formula (A), wherein n is 0, is further defined as a compound of formula (B):

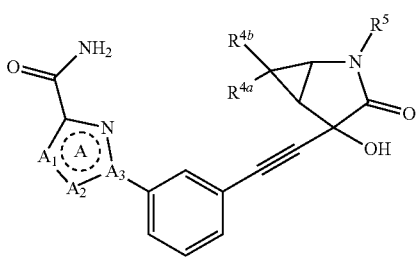

(B)

or a stereoisomer, tautomer, solvate, prodrug or salt thereof, wherein $A_1$, $A_2$, $A_3$, $R^{4a}$, $R^{4b}$ and $R^5$ are as defined for formula (A), or any variation thereof.

In some embodiments, a compound of formula (B) is further defined as a compound of formula (Ba):

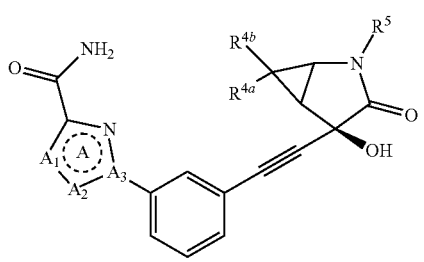

(Ba)

or a stereoisomer, tautomer, solvate, prodrug or salt thereof, wherein $A_1$, $A_2$, $A_3$, $R^{4a}$, $R^{4b}$ and $R^5$ are as defined for formula (B), or any variation thereof.

In some embodiments, a compound of formula (B) is further defined as a compound of formula (Ba-1):

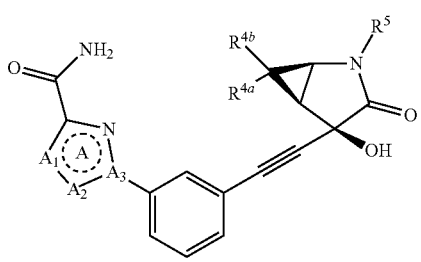

(Ba-1)

or a stereoisomer, tautomer, solvate, prodrug or salt thereof, wherein $A_1$, $A_2$, $A_3$, $R^{4a}$, $R^{4b}$ and $R^5$ are as defined for formula (B), or any variation thereof.

In some embodiments, a compound of formula (B) is further defined as a compound of formula (Ba-2):

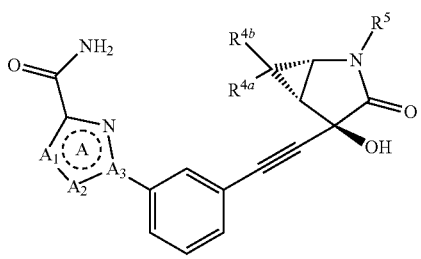

(Ba-2)

or a stereoisomer, tautomer, solvate, prodrug or salt thereof, wherein $A_1$, $A_2$, $A_3$, $R^{4a}$, $R^{4b}$ and $R^5$ are as defined for formula (B), or any variation thereof.

One aspect of the invention provides a compound of formula (C):

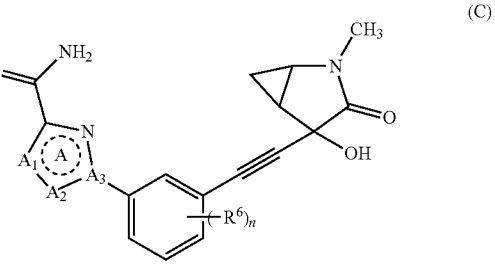

(C)

or a stereoisomer, tautomer, solvate, prodrug or salt thereof, wherein:

ring A is a monocycle or a fused bicycle;
$A_1$ is $NR^1$ or $CR^1$;
$A_2$ is $NR^2$, S or $CR^2$;
$A_3$ is N or C;
provided that no more than one of (i)-(iii) applies: (i) $A_1$ is $NR^1$, (ii) $A_2$ is $NR^2$, and (iii) $A_3$ is N;

each $R^1$ is independently —$NR^aR^b$; $C_1$-$C_3$ alkyl optionally substituted by F, OH, CN, SH or $C_1$-$C_3$ alkoxy; or taken together with $R^2$, where present, and the atoms to which they are attached to form a 6-membered heterocyclyl optionally substituted by $R^d$;

each $R^2$ is independently absent or taken together with $R^1$ and the atoms to which they are attached to form a 6-membered heterocyclyl optionally substituted by $R^d$;

n is 0 or 1;
$R^6$, where present, is halo;
each $R^a$ and $R^b$ is independently selected from the group consisting of H and $C_1$-$C_6$ alkyl; and
each $R^d$ is independently selected from the group consisting of $C_1$-$C_6$ alkyl optionally substituted by halogen and $C_1$-$C_6$ alkoxy optionally substituted by halogen.

It is understood that in the compound of the formula (C), no more than one of (i)-(iii) applies: (i) $A_1$ is $NR^1$; (ii) $A_2$ is $NR^2$; and (iii) $A_3$ is N. It is also understood that in the compound is of the formula (C), at least two of (iv)-(vi) apply: (iv) $A_1$ is $CR^1$; (v) $A_2$ is S or $CR^2$; and (vi) $A_3$ is C.

In some embodiments, ring A is an unsaturated monocycle or an unsaturated fused bicycle.

In some embodiments, a compound of formula (C) is further defined as a compound of formula (Ca):

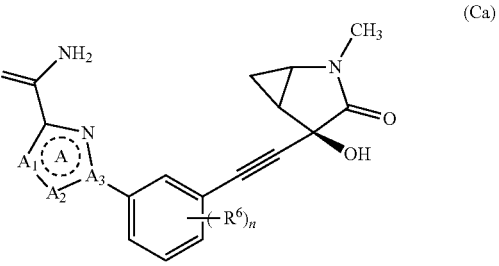

(Ca)

or a stereoisomer, tautomer, solvate, prodrug or salt thereof, wherein $A_1$, $A_2$, $A_3$, $R^6$ and n are as defined for formula (C), or any variation thereof.

In some embodiments, a compound of formula (C) is further defined as a compound of formula (Ca-1):

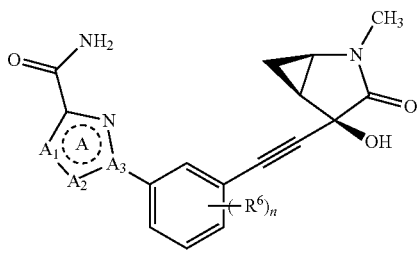

(Ca-1)

or a stereoisomer, tautomer, solvate, prodrug or salt thereof, wherein $A_1$, $A_2$, $A_3$, $R^6$ and n are as defined for formula (C), or any variation thereof.

In some embodiments, a compound of formula (C) is further defined as a compound of formula (Ca-2):

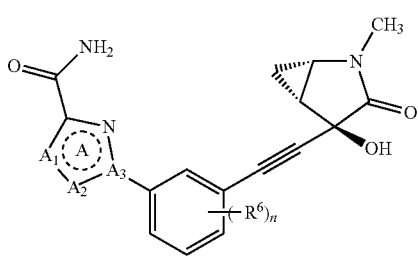

(Ca-2)

or a stereoisomer, tautomer, solvate, prodrug or salt thereof, wherein $A_1$, $A_2$, $A_3$, $R^6$ and n are as defined for formula (C), or any variation thereof.

In some embodiments, a compound of formula (C), wherein n is 0, is further defined as a compound of formula (D):

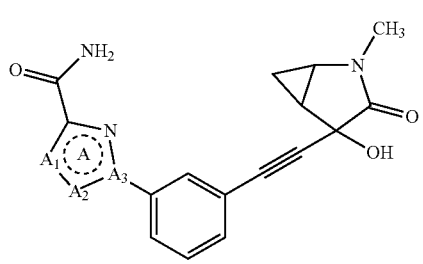

(D)

or a stereoisomer, tautomer, solvate, prodrug or salt thereof, wherein $A_1$, $A_2$ and $A_3$ are as defined for formula (C), or any variation thereof.

In some embodiments, a compound of formula (D) is further defined as a compound of formula (Da):

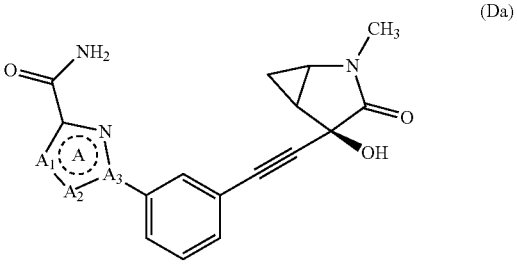

(Da)

or a stereoisomer, tautomer, solvate, prodrug or salt thereof, wherein A, $A_2$ and $A_3$ are as defined for formula (D), or any variation thereof.

In some embodiments, a compound of formula (D) is further defined as a compound of formula (Da-1):

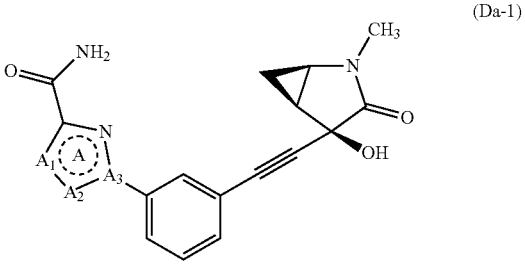

(Da-1)

or a stereoisomer, tautomer, solvate, prodrug or salt thereof, wherein $A_1$, $A_2$ and $A_3$ are as defined for formula (D), or any variation thereof.

In some embodiments, a compound of formula (D) is further defined as a compound of formula (Da-2):

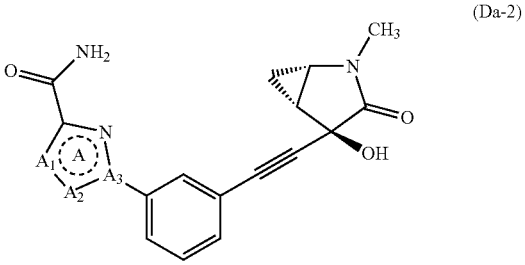

(Da-2)

or a stereoisomer, tautomer, solvate, prodrug or salt thereof, wherein $A_1$, $A_2$ and $A_3$ are as defined for formula (D), or any variation thereof.

In some embodiments of the compound of formula (I), (II) (A), (Aa), (Aa-1), (Aa-2), (B), (Ba), (Ba-1), (Ba-2), (C), (Ca), (Ca-1), (Ca-2), (D), (Da), (Da-1) or (Da-2), or any applicable variations thereof, or a stereoisomer, tautomer, solvate, prodrug or salt thereof, ring A is a monocycle. In some embodiments, $A_1$ is $NR^1$. In some embodiments, $A_1$ is $CR^1$. In some of these embodiments, $R^1$ is $NH_2$. In some embodiments, $A_2$ is $NR^2$. In some embodiments, $A_2$ is S. In some embodiments, $A_3$ is C. In some embodiments, $A_1$ is $CR^1$, $A_2$ is S, and $A_3$ is C. In some embodiments, $A_1$ is $CR^1$ where $R^1$ is $NH_2$, $A_2$ is S, and $A_3$ is C. In some embodiments, A is $CR^1$, $A_2$ is $NR^2$, and $A_3$ is C.

In some embodiments of the compound of formula (I), (II) (A), (Aa), (Aa-1), (Aa-2), (B), (Ba), (Ba-1), (Ba-2), (C), (Ca), (Ca-1), (Ca-2), (D), (Da), (Da-1) or (Da-2), or any applicable variations thereof, or a stereoisomer, tautomer, solvate, prodrug or salt thereof), $A_1$ is $CR^1$ wherein $R^1$ is selected from the group consisting of $NHC(O)NR^aR^b$; NHS$(O)_2CH_3$; $C_1$-$C_3$ alkyl substituted by $C_1$-$C_3$ alkoxy or 3-11 membered heterocyclyl; and 3-11 membered heterocyclyl substituted by $C_1$-$C_3$ alkyl. In some embodiments, $A_1$ is $CR^1$ wherein $R^1$ is $NHC(O)NR^aR^b$. In some of these embodiments, $R^a$ and $R^b$ are independently selected from the group consisting of H and $C_1$-$C_6$ alkyl. In some embodiments, $A_1$ is $CR^1$ wherein $R^1$ is $NHS(O)_2CH_3$. In some embodiments, $A_1$ is $CR^1$ wherein $R^1$ is 3-11 membered heterocyclyl substituted by $C_1$-$C_3$ alkyl. In some embodiments, A, is $CR^1$ wherein $R^1$ is $C_1$-$C_3$ alkyl substituted by $C_1$-$C_3$ alkoxy or 3-11 membered heterocyclyl.

In some embodiments, $R^1$ is selected from the group consisting of H, F and $C_1$.

In some embodiments, $R^1$ is $NR^aR^b$. In some of these embodiments, $R^a$ is H or $C_1$-$C_6$ alkyl. In some of these embodiments, $R^b$ is H; $C_1$-$C_6$ alkyl optionally substituted by $C_1$-$C_3$ alkoxy, F, OH, CN, SH, $CH_3$ or $CF_3$; or 3-11 membered heterocyclyl optionally substituted by $C_1$-$C_3$ alkoxy, F, OH, CN, SH, $CH_3$ or $CF_3$. In some of these embodiments, $R^b$ is $C(O)R^g$. In some embodiments, $R^g$ is $C_3$-$C_6$ cycloalkyl optionally substituted by F. In some embodiments, $R^1$ is $NH_2$.

In some embodiments, $A_1$ is $NR^1$. In some embodiments, A, is $NR^1$, $A_2$ is $CR^2$ and $A_3$ is C. In some of these embodiments, $R^1$ is H or $C_1$-$C_3$ alkyl. In some of these embodiments, $R^1$ is $C_1$-$C_3$ alkyl. In some embodiments, $A_1$ is $CR^1$. In some embodiments, $A_1$ is $CR^1$, $A_2$ is $CR^2$ and $A_3$ is N. In some embodiments, $A_1$ is $CR^1$ and $A_6$ is $CR^6$. In some of these embodiments, $A_2$ is $CR^2$ where $R^2$ is H or —$OCH_3$.

In some embodiments, $R^1$ is $C_1$-$C_3$ alkyl optionally substituted by F, OH, CN, SH, $C_1$-$C_3$ alkoxy or 3-11 membered heterocyclyl; $C_3$-$C_7$ cycloalkyl optionally substituted by F, OH, CN, SH, $CH_3$ or $CF_3$; or $C_1$-$C_3$ alkoxy. In some embodiments, $R^1$ is $C_1$-$C_3$ alkyl optionally substituted by F, OH, CN, SH or $C_1$-$C_3$ alkoxy.

In some embodiments, $R^1$ is 3-11 membered heterocyclyl optionally substituted by F, OH, CN, SH, $CF_3$ or $C_1$-$C_3$ alkyl.

In some embodiments, $R^1$ is a 5-6 membered heteroaryl optionally substituted by F, OH, CN, SH, $CF_3$ or $C_1$-$C_3$ alkyl.

In some embodiments, $R^1$ is selected from the group consisting of:

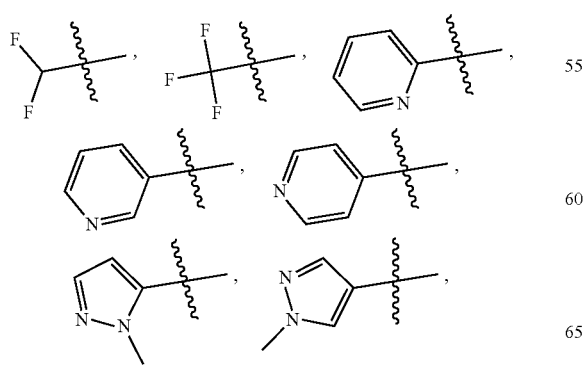

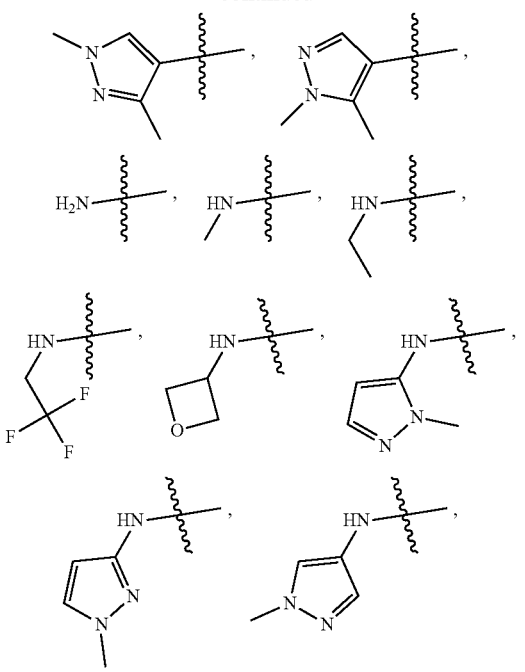

-continued

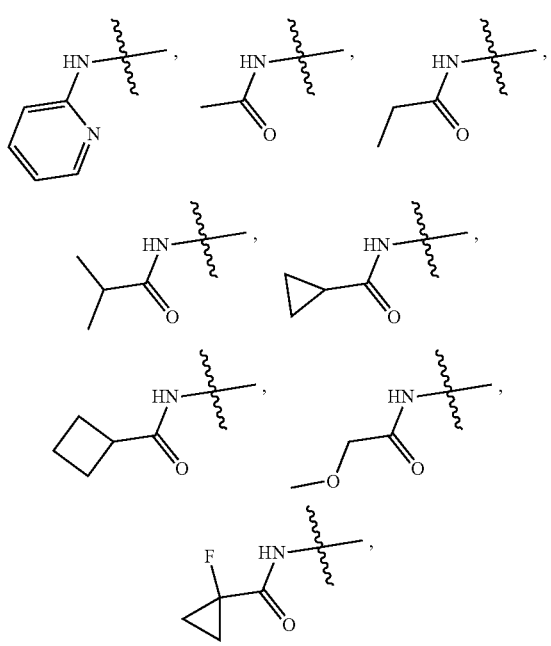

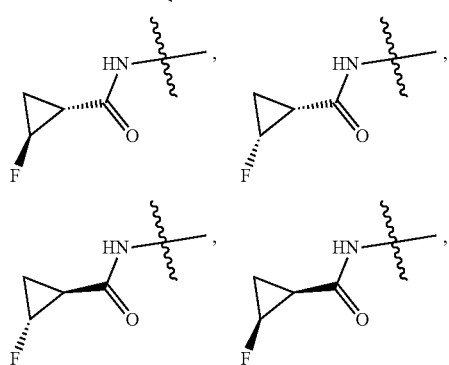

-continued

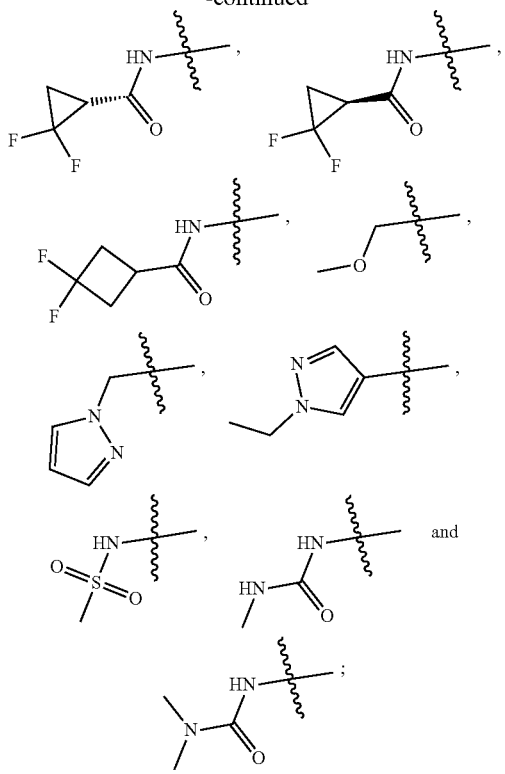

wherein the wavy line represents the point of attachment of $R^1$ in the parent structure.

In some embodiments, $R^2$ is selected from the group consisting of H, $NH_2$, $CH_3$ and cyclopropyl. In other embodiments, $R^2$ is a $C_3$-$C_{11}$ heterocycloalkyl.

In some embodiments, $A_1$ is $NR^1$ or $CR^1$; and $A_2$ is $NR^2$ or $CR^2$.

In some embodiments of the compound of formula (I), (II) (A), (Aa), (Aa-1), (Aa-2), (B), (Ba), (Ba-1), (Ba-2), (C), (Ca), (Ca-1), (Ca-2), (D), (Da), (Da-1) or (Da-2), or any applicable variations thereof, or a stereoisomer, tautomer, solvate, prodrug or salt thereof, ring A is a fused bicycle. In some embodiments, $A_1$ is $NR^1$ or $CR^1$, $A_2$ is $NR^2$ or $CR^2$, and $R^1$ and $R^2$ are taken together with the atoms to which they are attached to form a 3-11 membered heterocyclyl optionally substituted by $R^d$. In some of these embodiments, $A_1$ is $CR^1$, $A_2$ is $CR^2$ and $A_3$ is N. In some of these embodiments, $A_1$ is $NR^1$, $A_2$ is $CR^2$ and $A_3$ is C. In some of these embodiments, $A_1$ is $CR^1$, $A_2$ is $NR^2$ and $A_3$ is C.

In some embodiments, $R^1$ and $R^2$ together form the following cyclic group, wherein the asterisks indicate the points of ring fusion to ring A, and each cyclic group is optionally substituted by $R^d$:

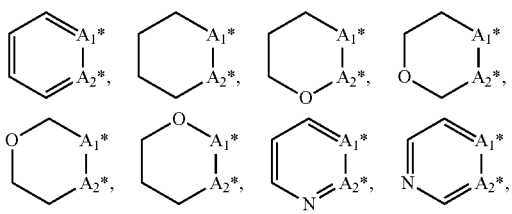

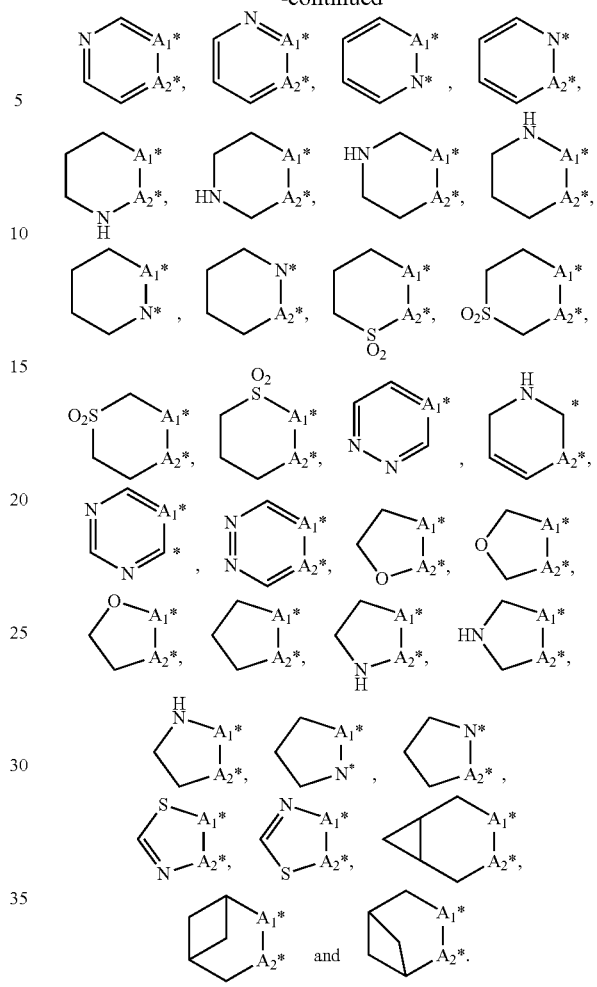

In some embodiments, $R^1$ and $R^2$ together form the following cyclic group, wherein the asterisks indicate the points of ring fusion to ring A, and each cyclic group is optionally substituted by $R^d$:

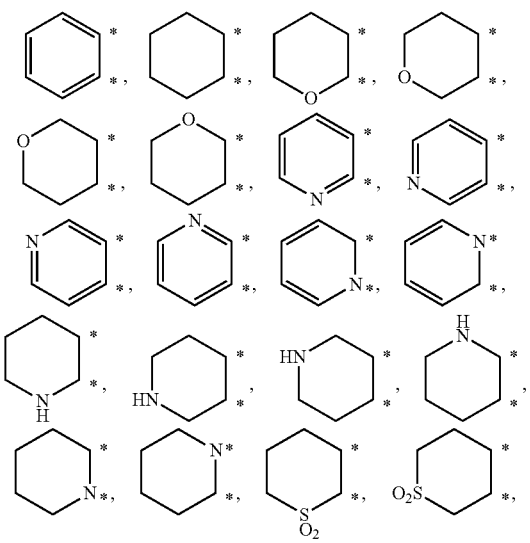

-continued

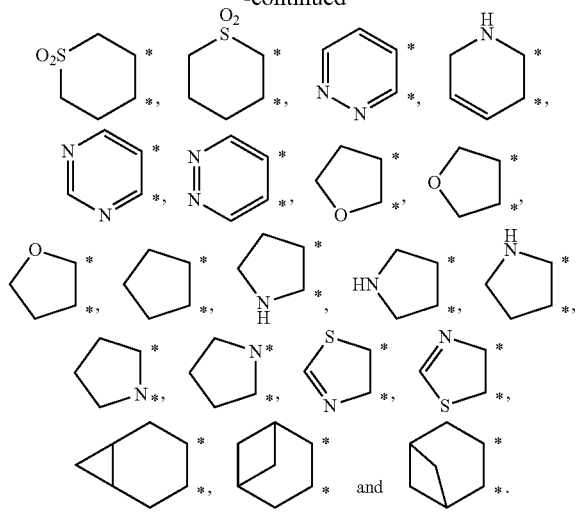

In some embodiments, $R^1$ and $R^2$ together with the atoms to which they are attached to form the following cyclic group, wherein the asterisks indicate the points of ring fusion to ring A, and each cyclic group is optionally substituted by $R^d$:

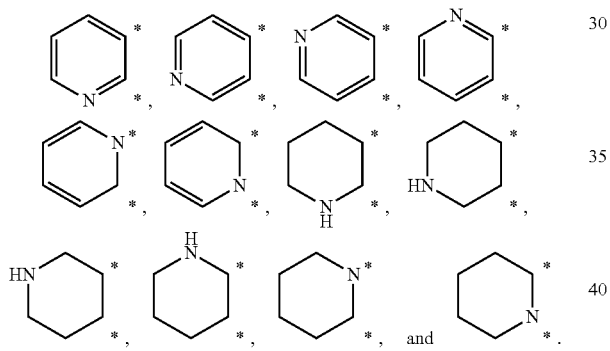

In some embodiments, $R^1$ and $R^2$ together form an unsubstituted cyclic group. In some embodiments, $R^1$ and $R^2$ together with the atoms to which they are attached to form an unsubstituted 6-membered heterocyclyl group.

In some embodiments, ring A is selected from the group consisting of:

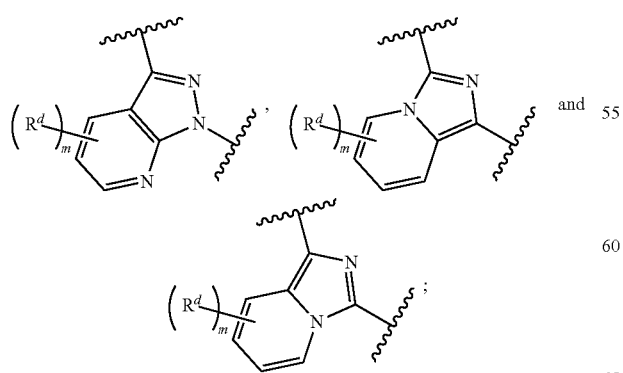

wherein each m is independently 0, 1, 2 or 3.

In some embodiments, ring A is

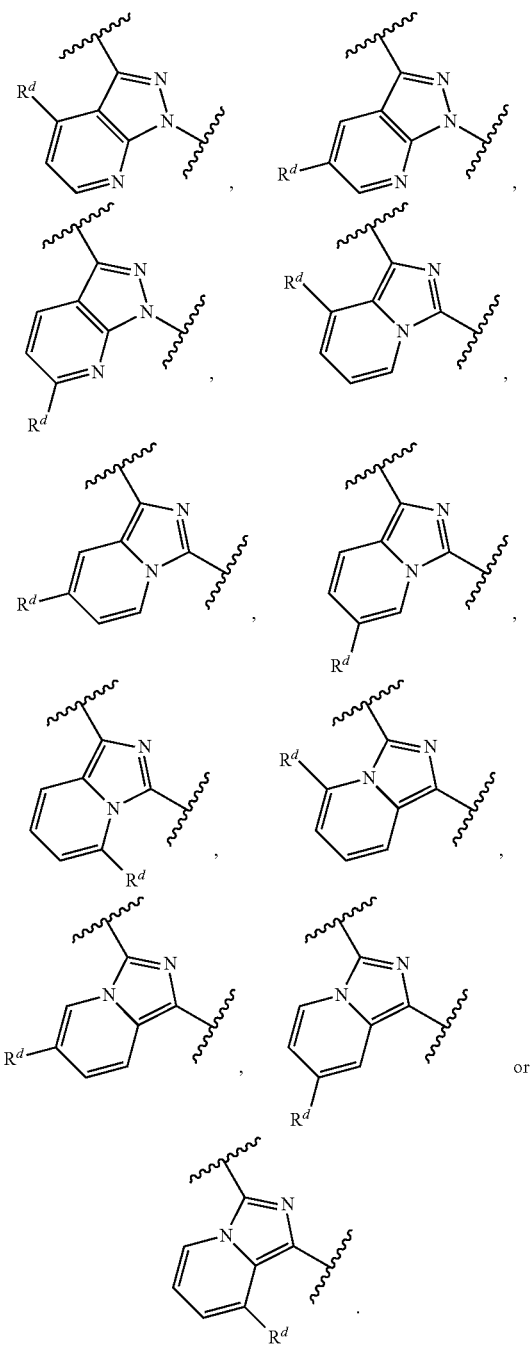

In some embodiments, ring A is selected from the group consisting of:

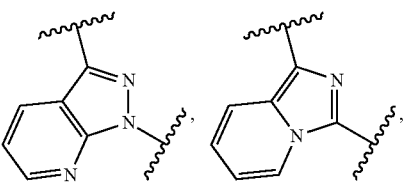

-continued

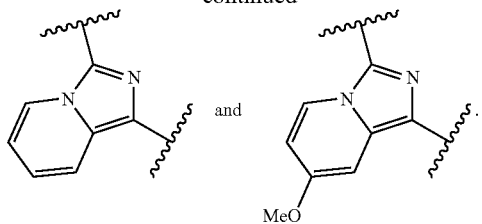

In some embodiments, $R^d$ is selected from the group consisting of OH, CN, F, $C_1$-$C_3$ alkoxy, —O—$C_1$-$C_3$ alkylphenyl, $NR^aR^b$, 4-6 membered heterocyclyl, $C(O)R^g$, $C(O)_2R^g$ and $C_1$-$C_6$ alkyl optionally substituted by OH, CN, or 4-6 membered heterocyclyl. In some embodiments, $R^d$ is $C_1$-$C_6$ alkyl optionally substituted by halogen. In some embodiments, $R^d$ is $C_1$-$C_3$ alkoxy (e.g., $OCH_3$).

In some embodiments, $R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, —$(X^1)_{0-1}$—$C_1$-$C_6$ alkyl, —$(X^1)_{0-1}$—$C_3$-$C_7$ cycloalkyl, —$(X^1)_{0-1}$-3-11 membered heterocyclyl (e.g., a 4-7 membered heterocycloalkyl or a 5-6 membered heteroaryl), —$(X^1)_{0-1}$—$C_6$-$C_{10}$ aryl, —C(=O)($X^1)_{0-1}$-$C_3$-$C_7$ cycloalkyl, —C(=O)($X^1)_{0-1}$-3-11 membered heterocyclyl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^b$)C(=$Y^1$)(H), —$(X^1)_{0-1}$—N(H)C(=$Y^1$)$OR^{1a}$, —$(X^1)_{0-1}$—N($R^b$)C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^1$)$R^{1a}$, and —$(X^1)_{0-1}$—C(=$Y^1$)H, wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^b$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, 3-11 membered heterocyclyl, and phenyl, or $R^{1a}$ and $R^b$ when attached to the same nitrogen atom are optionally combined to form a 3-11 membered heterocyclyl (e.g., a 4-7 membered heterocycloalkyl or a 5-6 membered heteroaryl) comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is each independently further substituted by from 0 to 4 $R^f$ substituents selected from the group consisting of halogen, CN, $NO_2$, OH, $NH_2$, —N($C_1$-$C_6$ alkyl)$_2$, —NH($C_1$-$C_6$ alkyl), oxo, $C_1$-$C_6$ alkyl, $C_1$-$C_6$ haloalkyl, $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, or 3-11 membered heterocyclyl (e.g., a 4-7 membered heterocycloalkyl or a 5-6 membered heteroaryl).

In some embodiments of the compounds of formula (A), (Aa), (Aa-1), (Aa-2), (C), (Ca), (Ca-1) or (Ca-2), or a stereoisomer, tautomer, solvate, prodrug or salt thereof, n is 0, 1 or 2, and each $R^6$ is independently selected from the group consisting of F, Cl, $OCH_3$, $CH_3$ and $CF_3$. In some embodiments, n is 0. In some embodiments, n is 1. In some embodiments, n is 1, and $R^6$ is F.

In some embodiments, n is 1 and the ring bearing the $R^6$ group (ring B) is:

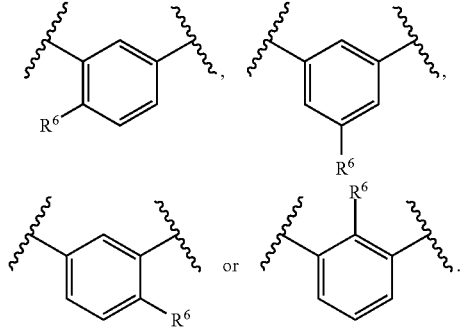

In some embodiments, n is 2 and ring bearing the two independently selected $R^6$ group (ring B) is:

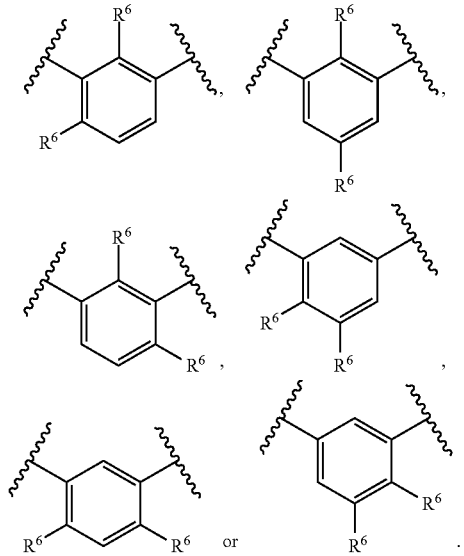

In some embodiments of the compounds of formula (I), (II), (A), (Aa), (Aa-1), (Aa-2), (B), (Ba), (Ba-1) or (Ba-2), or a stereoisomer, tautomer, solvate, prodrug or salt thereof, each $R^{4a}$ and $R^{4b}$ is independently H or F; and $R^5$ is $C_1$-$C_6$ alkyl optionally substituted by halogen, OH, or $C_1$-$C_6$ alkoxy or $C_3$-$C_4$ cycloalkyl optionally substituted by halogen, OH, or $C_1$-$C_6$ alkoxy. In some embodiments, each $R^{4a}$ and $R^{4b}$ is H. In some embodiments, each $R^{4a}$ and $R^{4b}$ is F. In some embodiments, $R^5$ is $C_1$-$C_6$ alkyl optionally substituted by halogen, OH, or $C_1$-$C_6$ alkoxy. In some embodiments, $R^5$ is $C_3$-$C_4$ cycloalkyl optionally substituted by halogen, OH, or $C_1$-$C_6$ alkoxy. In some embodiments, $R^5$ is $C_1$-$C_6$ alkyl. In some embodiments, $R^5$ is $C_1$-$C_3$ alkyl (e.g., methyl).

It is intended and understood that each and every variation of $A_1$-$A_4$, including variations of $R^1$ and $R^2$ where applicable, described for formula (I), (II), (A), (Aa), (Aa-1), (Aa-2), (B), (Ba), (Ba-1) or (Ba-2) may be combined with each and every variation of $R^{4a}$, $R^{4b}$ and $R^5$ described for formula (I), (II), (A), (Aa), (Aa-1), (Aa-2), (B), (Ba), (Ba-1) or (Ba-2) as if each and every combination is individually described. For example, in some embodiments of the compounds of formula (I), (II), (A), (Aa), (Aa-1), (Aa-2), (B), (Ba), (Ba-1) or (Ba-2), or a stereoisomer, tautomer, solvate, prodrug or salt thereof, each $R^{4a}$ and $R^{4b}$ is H; $R^5$ is methyl; and ring A is selected from the group consisting of:

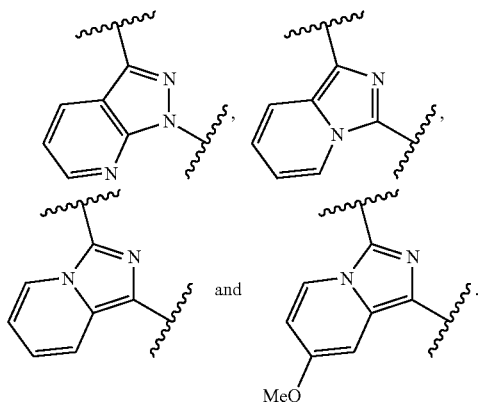

In some embodiments, a heterocyclyl group contains one to three nitrogen atoms, one oxygen atom, or one sulfur atom, or any combination thereof.

In some embodiments, a compound of the present invention is defined as any one or more of the following:

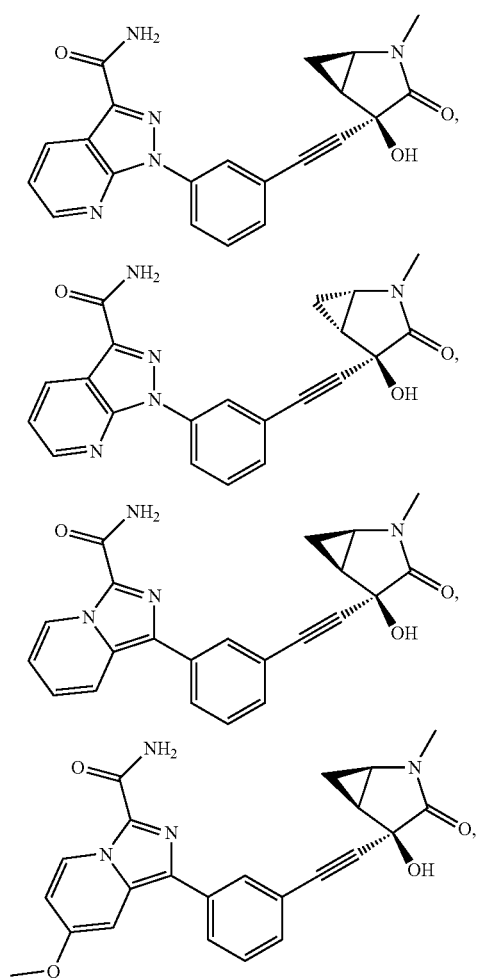

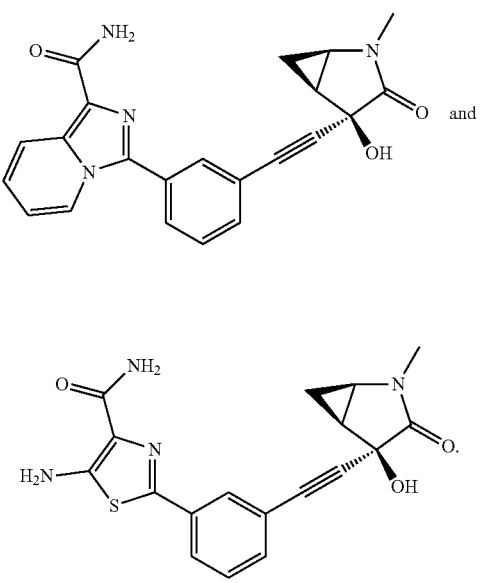

In some embodiments, a compound of the present invention is defined as any one or more of the following:

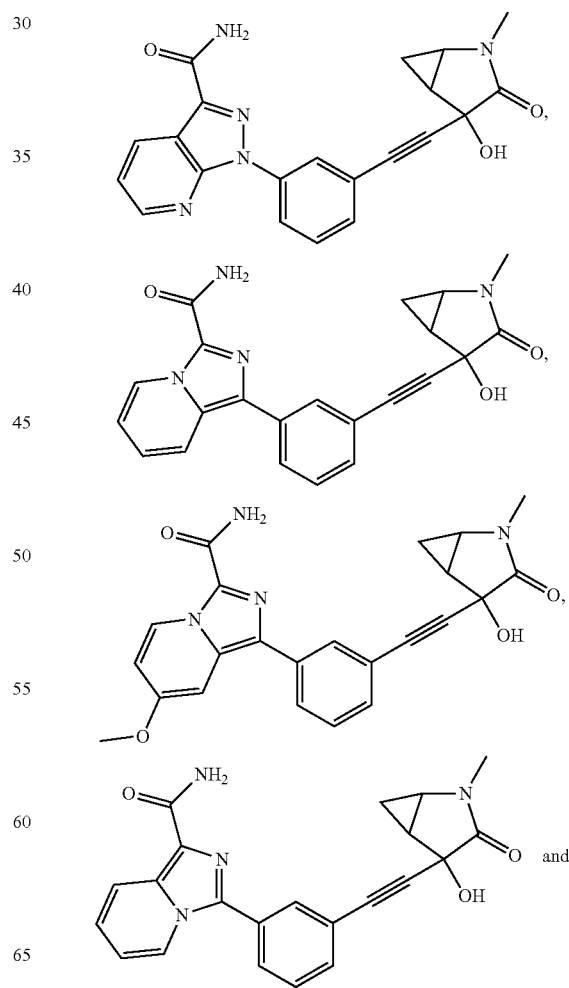

-continued

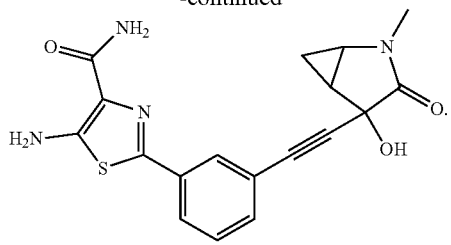

Some embodiments provide a pharmaceutical composition comprising a compound of the present invention and a pharmaceutically acceptable carrier, diluent or excipient. A compound or pharmaceutical composition described herein can be used in therapy, such as the treatment of a cancer, a fibrotic condition, or an inflammatory condition (e.g., lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection). Also provided is the use of a compound or a pharmaceutical composition described herein for the preparation of a medicament for the treatment of an inflammatory condition (e.g., lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection).

Also provided is a method for the treatment of an inflammatory condition in a patient, comprising administering an effective amount of a compound or pharmaceutical composition as described herein to the patient. The inflammatory condition can be selected from the group consisting of lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection.

Also provided is a kit comprising a compound of formula (I), (II) (A), (Aa), (Aa-1), (Aa-2), (B), (Ba), (Ba-1), (Ba-2), (C), (Ca), (Ca-1), (Ca-2), (D), (Da), (Da-1) or (Da-2), or a stereoisomer, tautomer, solvate, prodrug or salt thereof. Also provided is a kit comprising a pharmaceutical composition comprising a compound of formula (I), (II) (A), (Aa), (Aa-1), (Aa-2), (B), (Ba), (Ba-1), (Ba-2), (C), (Ca), (Ca-1), (Ca-2), (D), (Da), (Da-1) or (Da-2), or a stereoisomer, tautomer, solvate, prodrug or salt thereof. The kit may further comprise instructions for use, for example, according to a method described herein. In some embodiments, the kit comprises packaging.

Further provided is a method of preparing a compound of formula (I):

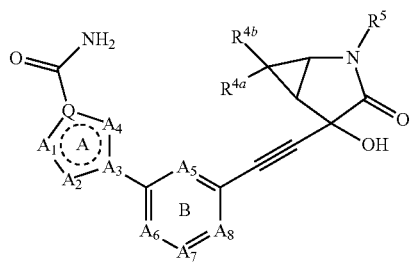

wherein Q, $A_1$, $A_2$, $A_3$, $A_5$, $A_6$, $A_7$, $A_8$, $R^{4a}$, $R^{4b}$ and $R^5$ are as defined above, comprising:

(i) reacting a compound of formula (I-1):

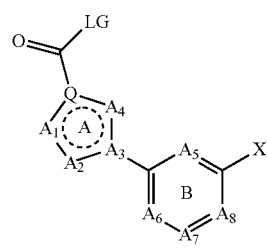

wherein X is —Cl, —Br, —I, —OS(O)$_2$CF$_3$ (i.e. —OTf), —OC(O)CH$_3$ (i.e. —OAc), —OS(O)$_2$CH$_3$ (i.e. —OMs), —OS(O)$_2$(CH$_3$C$_6$H$_4$) (i.e. —OTs), or —N$_2^+$ (i.e. diazonium); and LG is a leaving group;

with a compound of formula (I-2):

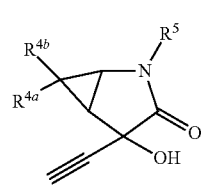

to form a compound of formula (I-3):

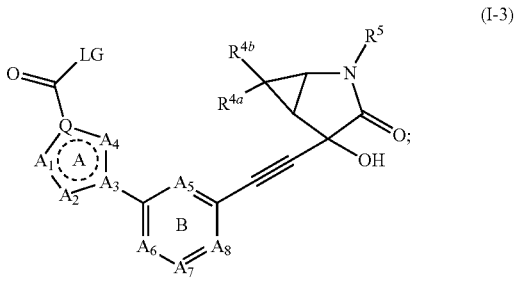

and (ii) converting the compound of formula (I-3) to the compound of formula (I).

In some embodiments of the method of preparation, Q is C.

In some embodiments, the method of preparing a compound of formula (I) further comprises the steps of:

(i) reacting a compound of formula (I-4):

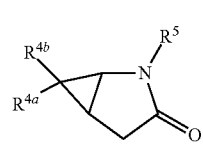

wherein $R^{4a}$, $R^{4b}$ and $R^5$ are as defined above, with bis(trimethylsilyl)peroxide to form a compound of formula (I-5):

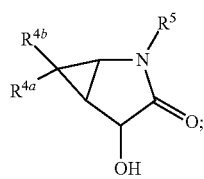

and (ii) converting the compound of formula (I-5) to the compound of formula (I-2).

Also provided is a method of preparing a compound of formula (A):

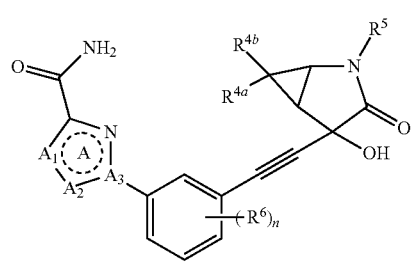

wherein $A_1$, $A_2$, $A_3$, $R^{4a}$, $R^{4b}$, $R^5$, $R^6$ and n are as defined above, comprising:

(i) reacting a compound of formula (A-1):

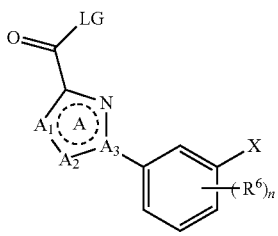

wherein X is —Cl, —Br, —I, —OS(O)$_2$CF$_3$ (i.e. —OTf), —OC(O)CH$_3$ (i.e. —OAc), —OS(O)$_2$CH$_3$ (i.e. —OMs), —OS(O)$_2$(CH$_3$C$_6$H$_4$) (i.e. —OTs), or —N$_2^+$ (i.e. diazonium); and LG is a leaving group;

with a compound of formula (A-2):

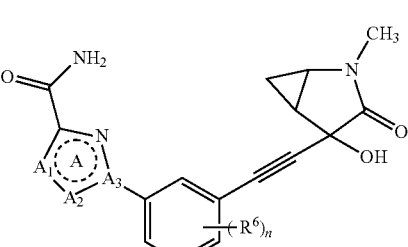

to form a compound of formula (A-3):

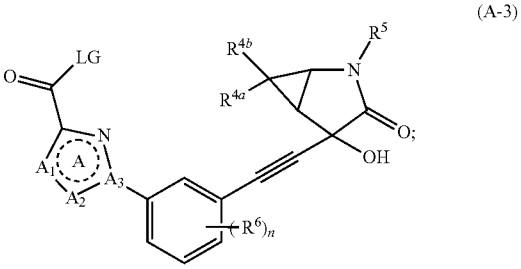

and (ii) converting the compound of formula (A-3) to the compound of formula (A).

In some of these embodiments, n is 0 (i.e., $R^6$ is absent).

In some embodiments, the method of preparing a compound of formula (A) further comprises the steps of:

(i) reacting a compound of formula (A-4):

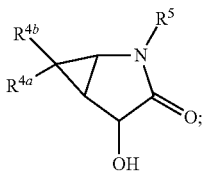

wherein $R^{4a}$, $R^{4b}$ and $R^5$ are as defined above, with bis(trimethylsilyl)peroxide to form a compound of formula (A-5):

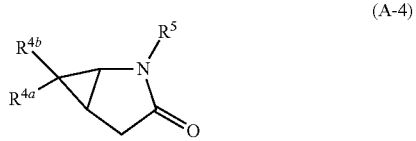

and (ii) converting the compound of formula (I-5) to the compound of formula (A-2).

In some embodiments of the method of making a compound of formula (I) or (A), each $R^{4a}$ and $R^{4b}$ is H; and $R^5$ is methyl.

Further provided is a method of preparing a compound of formula (C):

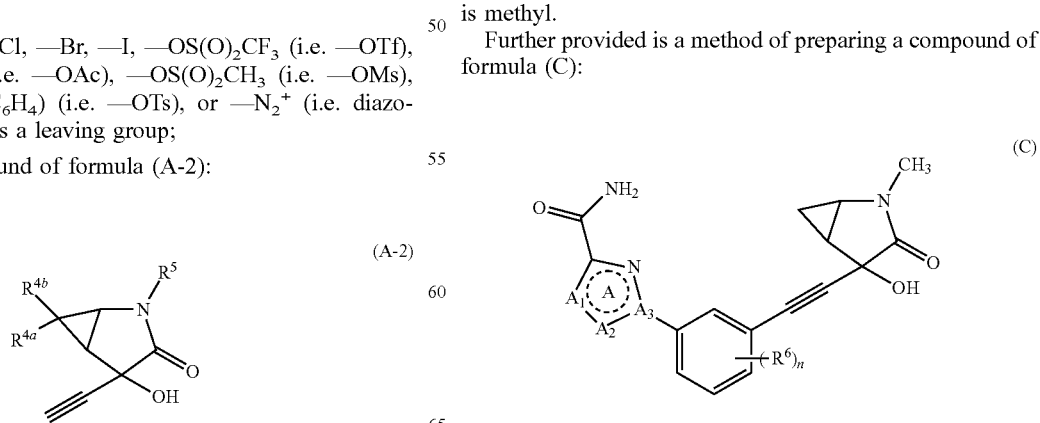

wherein $A_1$, $A_2$, $A_3$, $R^6$ and n are as defined above, comprising:

(i) reacting a compound of formula (C-1):

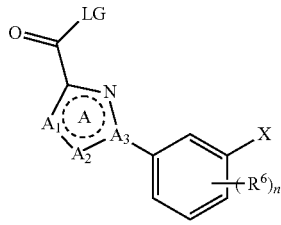
(C-1)

wherein X is —Cl, —Br, —I, —OS(O)$_2$CF$_3$ (i.e. —OTf), —OC(O)CH$_3$ (i.e. —OAc), —OS(O)$_2$CH$_3$ (i.e. —OMs), —OS(O)$_2$(CH$_3$C$_6$H$_4$) (i.e. —OTs), or —N$_2^+$ (i.e. diazonium); and LG is a leaving group; with a compound of formula (C-2):

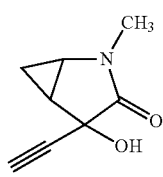
(C-2)

to form a compound of formula (C-3):

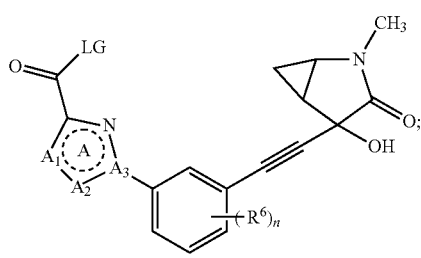
(C-3)

and (ii) converting the compound of formula (C-3) to the compound of formula (C).

In some of these embodiments, n is 0 (i.e., R$^6$ is absent).

In some embodiments, the method of preparing a compound of formula (C) further comprises the steps of:

(i) reacting a compound of formula (1):

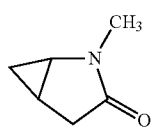
(1)

with bis(trimethylsilyl)peroxide to form a compound of formula (2):

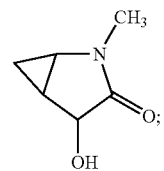
(2)

and (ii) converting the compound of formula (2) to the compound of formula (C-2).

The alpha-hydroxylation of the compound of formula (1) into the compound of formula (2) was performed with bis(trimethylsilyl)peroxide. More commonly used reagents for the alpha-hydroxylation of amide and lactam compounds are Davis reagent (3-phenyl-2-(phenylsulfonyl)-1,2-oxaziridine) and related N-sulfonyloxaziridine compounds. However, attempts to produce the compound of formula (2) by reacting the compound of formula (1) with Davis reagent were unsuccessful. Inorganic peroxides (e.g., Vedejs reagent) are also useful for alpha-hydroxylation of amides and lactams. See, e.g., Davis, F. A. et al. *Tetrahedron Lett.* 1978, 19, 5171, Davis, F. A. et al. *J. Org. Chem.* 1984, 49, 3241, Davis, F. A. et al. *J. Am. Chem. Soc.* 1990, 112, 6679, and Davis, F. A. et al. *Chem. Rev.* 1992, 92, 919; Pohmakotr, M. et al. *Synth. Commun.*, 1988, 18(16-17), 2141-6; Wagnieres, O. et al. *J. Am. Chem. Soc.*, 2014, 136(42), 15102-15108; and Sears, J. E. et al. *Org. Lett.*, 2015, 17(21), 5460-5463.

The coupling reaction between a compound of formula (I-1) or a variation thereof (e.g., formula (A-1) or (C-1)) and a compound of formula (I-2) or a variation thereof (e.g., a compound of (A-2) or (C-2)) may be carried out using coupling methods know in the art, for example, a Suzuki reaction or a Sonogashira reaction, and employing know reagents and catalysts. In some embodiments, the method of preparation comprises reacting a compound of formula (I-1) or a variation thereof (e.g., formula (A-1) or (C-1)) with a compound of formula (I-2) or a variation thereof (e.g., a compound of (A-2) or (C-2)) in the presence of a metal catalyst comprising a metal selected from Fe, Pd, Ni, Co, Cu and combinations thereof. In some embodiments, the metal catalyst comprises Pd, Ni, Fe or Cu. In some embodiments, the catalyst comprises a Fe/Cu mixture, a Pd/Cu mixture, a Ni/Cu mixture, or a Co/Cu mixture. In some embodiments, the catalyst comprises Pd (alone); Ni (alone); Fe (alone), or Cu (alone). These catalysts may be used with suitable ligands and reagents known in the art.

Persons of skill in the art are familiar with Suzuki reactions and the reagents employed in such reactions. See, e.g., Suzuki, J. Organometallic Chem., 576:147-168 (1999). Non-limiting examples of palladium catalysts include Pd(PPh$_3$)$_4$, Pd(OAc)$_2$ and Pd(PPh$_3$)$_2$Cl$_2$. A non-limiting example of a copper catalyst is copper(II) acetate. Non-limiting examples of bases include sodium carbonate, potassium carbonate and cesium carbonate, or mixtures thereof. In some embodiments, copper(II) acetate and pyridine as the base are employed under Chan-Lam coupling conditions, as is known in the art. For example, the carbon-nitrogen bond in an indazole or an aza-indazole can be formed using Chan-Lam coupling conditions. A variety of organic solvents may be employed, including toluene, THF, dioxane, 1,2-dichloroethane, DMF, DMSO and acetonitrile. Reaction temperatures vary depending on conditions but typically range from room temperature to 150° C.

Reagents, catalysts and ligands employed in Sonogashira reactions are known in the art, see, e.g., Rafael Chinchilla, Carmen Nájera, *Chem. Soc. Rev.*, 2011, 40:5084-5121, and Marc Schilz, Herbert Plenio, *J. Org. Chem.*, 2012, 77 (6):2798-2807.

Leaving groups (LG) useful in the synthetic methods described herein include but are not limited to alkoxy (e.g., —OCH$_3$), halogen (e.g., —F, -Cl, —Br, —I), —CN, —O-heteroaryl, (e.g., —O-(benzotriazol-1-yl) and —O—(N-succinimidyl)), —O-aryl (e.g., —OC$_6$F$_5$), N-imidazolyl, —O-acyl, and thiol. Other suitable leaving groups (LG) know in the art may also be used in the method, for example, leaving groups described in Greene's Protective Groups in Organic Synthesis 4$^{th}$ edition, Wiley-Interscience, New York, 2006.

In some embodiments, the method of preparation further comprises steps of making a compound of formula (I-1) or a variation thereof (e.g., formula (A-1) or (C-1)). In some embodiments, the method further comprises steps of making a compound of formula (I-2) or a variation thereof (e.g., a compound of (A-2) or (C-2)).

Synthetic intermediate of formula (I-2) or (A-2) or (C-2) may be synthesized using methods known in the art (see, e.g., *Angew. Chem. Int'l Ed.*, 2015, 40:11826-11829.) and synthetic procedures described herein. For example, the compound of formula (C-2) may be synthesized according to Scheme 1 or 2.

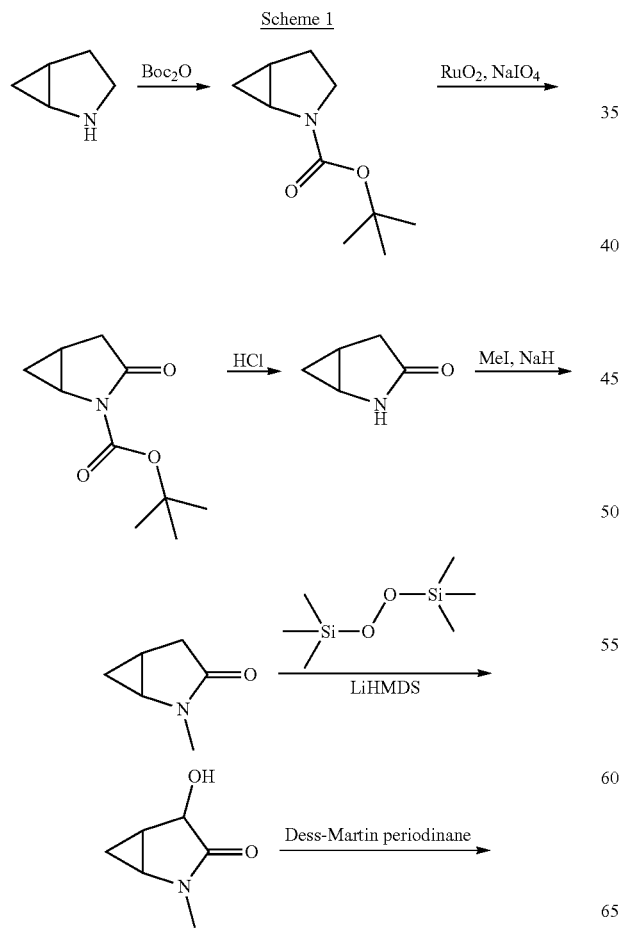

Scheme 1

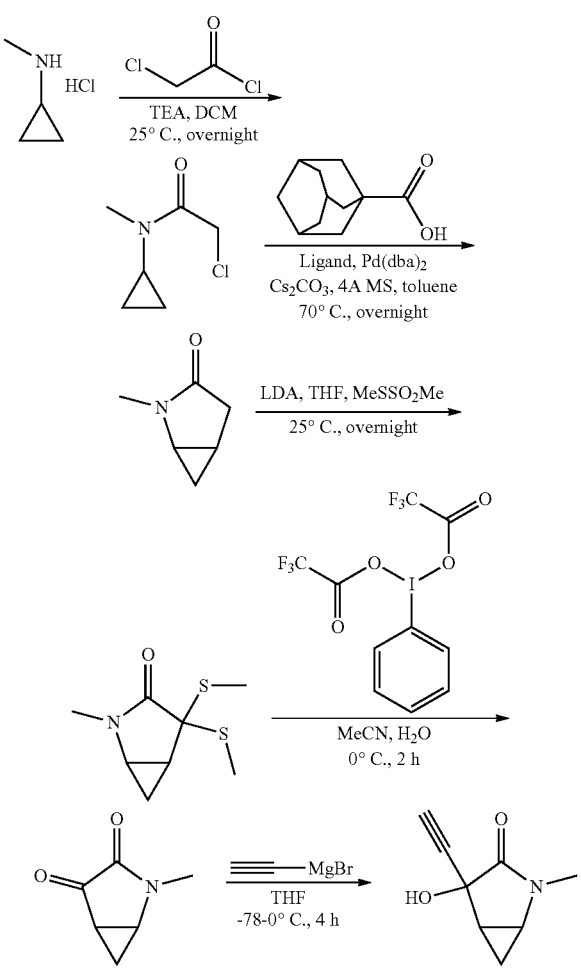

Scheme 2

Compound of formula (I-2) where R$^{4a}$ and R$^{4b}$ are F may be synthesized according to processes similar to those in Scheme 1 using tert-butyl 6,6-difluoro-2-azabicyclo[3.1.0]hexane-2-carboxylate as a starting material, or Scheme 2 using 2,2-difluorocyclopropan-1-amine as a starting material. The difluoro compound of formula (I-2) may be reacted with a compound of formula (I-1) to product compounds of formula (I) where R$^{4a}$ and R$^{4b}$ are F, or a salt there of, for example, Compound Nos. 8-12, or a salt thereof.

In some embodiments, the invention provides a compound selected from compounds in Table 1, or a stereoisomer, tautomer, solvate, prodrug or salt thereof. In some embodiments, provided is a compound selected from compounds in Table 1, or a stereoisomer, tautomer, or salt thereof. The invention also intends non-stereo-specific forms of the compounds depicted in Table 1, or a mixture of stereoisomers thereof, or salts thereof.

TABLE 1

| Compound No. | Structure | Name |
|---|---|---|
| 1 | 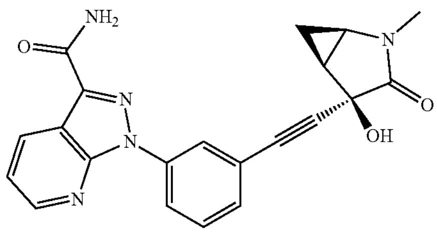 [SMILES: CN1C(=O)[C@](O)(C#Cc2cccc(-n3nc(C(N)=O)c4cccnc43)c2)[C@H]2C[C@H]21] | 1-(3-(((1R,4R,5S)-4-hydroxy-2-methyl-3-oxo-2-azabicyclo[3.1.0]hexan-4-yl)ethynyl)phenyl)-1H-pyrazolo[3,4-b]pyridine-3-carboxamide |
| 2 | 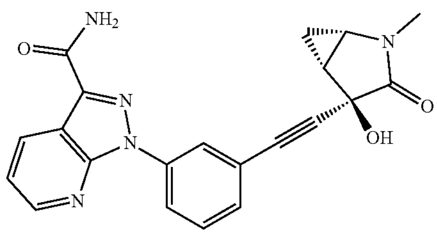 [SMILES: CN1C(=O)[C@](O)(C#Cc2cccc(-n3nc(C(N)=O)c4cccnc43)c2)[C@@H]2C[C@@H]21] | 1-(3-(((1S,4R,5R)-4-hydroxy-2-methyl-3-oxo-2-azabicyclo[3.1.0]hexan-4-yl)ethynyl)phenyl)-1H-pyrazolo[3,4-b]pyridine-3-carboxamide |
| 3 | 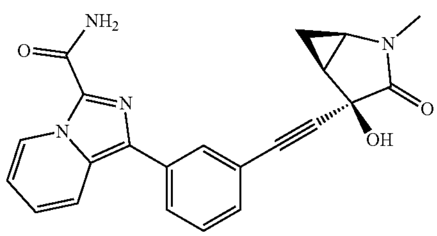 [SMILES: CN1C(=O)[C@](O)(C#Cc2cccc(-c3nc(C(N)=O)n4ccccc34)c2)[C@H]2C[C@H]21] | 3-(3-(((1R,4R,5S)-4-hydroxy-2-methyl-3-oxo-2-azabicyclo[3.1.0]hexan-4-yl)ethynyl)phenyl)imidazo[1,5-a]pyridine-1-carboxamide |
| 4 | 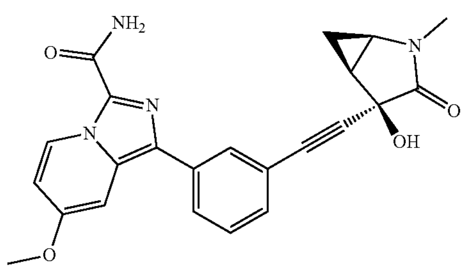 [SMILES: COc1ccn2c(C(N)=O)nc(-c3cccc(C#C[C@@]4(O)C(=O)N(C)[C@@H]5C[C@@H]54)c3)c2c1] | 1-(3-(((1R,4R,5S)-4-hydroxy-2-methyl-3-oxo-2-azabicyclo[3.1.0]hexan-4-yl)ethynyl)phenyl)-7-methoxyimidazo[1,5-a]pyridine-3-carboxamide |
| 5 | 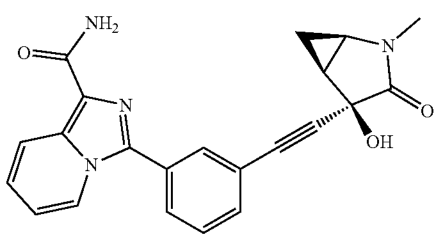 [SMILES: CN1C(=O)[C@](O)(C#Cc2cccc(-c3nc(C(N)=O)c4ccccn34)c2)[C@H]2C[C@H]21] | 3-(3-(((1R,4R,5S)-4-hydroxy-2-methyl-3-oxo-2-azabicyclo[3.1.0]hexan-4-yl)ethynyl)phenyl)imidazo[1,5-a]pyridine-1-carboxamide |
| 6 | 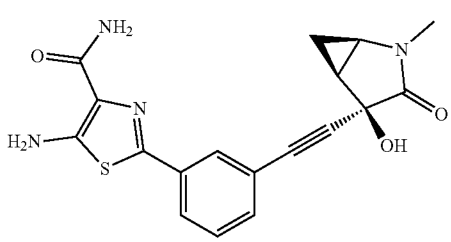 [SMILES: CN1C(=O)[C@](O)(C#Cc2cccc(-c3nc(C(N)=O)c(N)s3)c2)[C@H]2C[C@H]21] | 5-amino-2-(3-(((1R,4R,5S)-4-hydroxy-2-methyl-3-oxo-2-azabicyclo[3.1.0]hexan-4-yl)ethynyl)phenyl)thiazole-4-carboxamide |

TABLE 1-continued

| Compound No. | Structure | Name |
|---|---|---|
| 7 | 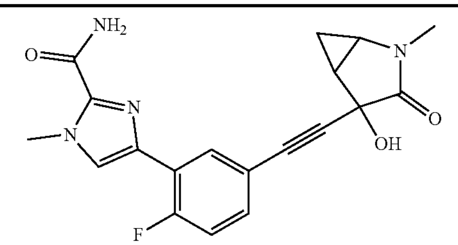 | 4-(2-fluoro-5-((4-hydroxy-2-methyl-3-oxo-2-azabicyclo[3.1.0]hexan-4-yl)ethynyl)phenyl)-1-methyl-1H-imidazole-2-carboxamide |
| 8 | 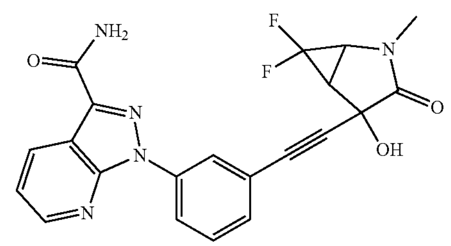 [SMILES: CN1C(=O)C(O)(C#Cc2cccc(-n3nc(C(N)=O)c4cccnc43)c2)C2C1C2(F)F] | 1-(3-((6,6-difluoro-4-hydroxy-2-methyl-3-oxo-2-azabicyclo[3.1.0]hexan-4-yl)ethynyl)phenyl)-1H-pyrazolo[3,4-b]pyridine-3-carboxamide |
| 9 | 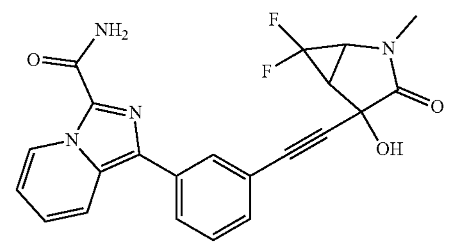 [SMILES: CN1C(=O)C(O)(C#Cc2cccc(-c3nc(C(N)=O)n4ccccc34)c2)C2C1C2(F)F] | 1-(3-((6,6-difluoro-4-hydroxy-2-methyl-3-oxo-2-azabicyclo[3.1.0]hexan-4-yl)ethynyl)phenyl)imidazo[1,5-a]pyridine-3-carboxamide |
| 10 | 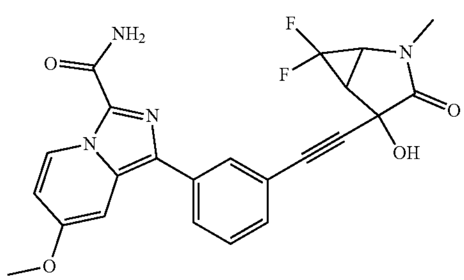 [SMILES: COc1ccn2c(C(N)=O)nc(-c3cccc(C#CC4(O)C(=O)N(C)C5C4C5(F)F)c3)c2c1] | 1-(3-((6,6-difluoro-4-hydroxy-2-methyl-3-oxo-2-azabicyclo[3.1.0]hexan-4-yl)ethynyl)phenyl)-7-methoxyimidazo[1,5-a]pyridine-3-carboxamide |
| 11 | 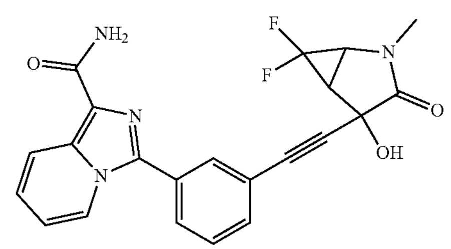 [SMILES: CN1C(=O)C(O)(C#Cc2cccc(-c3nc(C(N)=O)c4ccccn34)c2)C2C1C2(F)F] | 3-(3-((6,6-difluoro-4-hydroxy-2-methyl-3-oxo-2-azabicyclo[3.1.0]hexan-4-yl)ethynyl)phenyl)imidazo[1,5-a]pyridine-1-carboxamide |
| 12 | 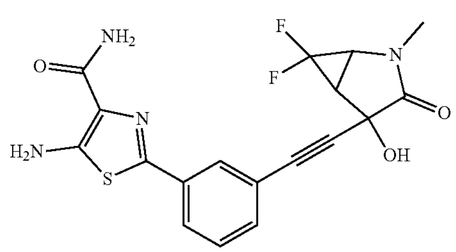 [SMILES: CN1C(=O)C(O)(C#Cc2cccc(-c3nc(C(N)=O)c(N)s3)c2)C2C1C2(F)F] | 5-amino-2-(3-((6,6-difluoro-4-hydroxy-2-methyl-3-oxo-2-azabicyclo[3.1.0]hexan-4-yl)ethynyl)phenyl)thiazole-4-carboxamide |

In some embodiments, the invention provides a compound in the Examples.

In some embodiments, the compound is selected from Compound Nos. 1-12, or a salt thereof. In some embodiments, the compound is selected from Compound Nos. 1-5, or a salt thereof. In some embodiments, the compound is selected from Compound No. 6, or a salt thereof.

The 4-alkynyl-4-hydroxy-2-azabicyclo[3.1.0]hexan-3-one compounds of the present invention demonstrate superior metabolic stability to the corresponding 3-alkynyl-3-hydroxy-pyrrolidin-2-one analogs. For example, Compound Nos. 1-6 were found to improve metabolic stability and have generally lower clearance in human liver microsomes and human hepatocytes than the corresponding comparator compounds shown in Table 2. Thus the 2-azabicyclo[3.1.0]hexan-3-one NIK inhibitor compounds of the present invention can be advantageous in use for treating a disease or condition in a human subject responsive to NIK inhibition (e.g., an inflammatory condition or a cancer). Metabolic stability of drug compounds can be evaluated using known methods, for example, in human liver microsomes and human hepatocytes, following protocols described in Halladay, et al. *Drug Metabol. Lett.* 2007, 1:67-72; Hallifax, et al. *Drug Metabol. Disposition*, 2005, 33:1852-1858; and Liu, et al. *Drug Metabol. Disposition*, 2011, 39:1840-1849.

TABLE 2

| Compound No. | Structure |
|---|---|
| 1 | 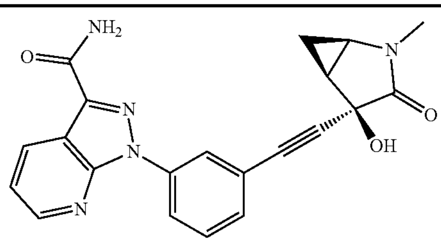 |
| 2 | 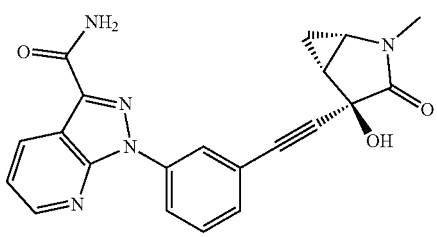 [SMILES: CN1C(=O)[C@](O)(C#Cc2cccc(-n3nc(C(N)=O)c4cccnc43)c2)[C@@H]2C[C@@H]21] |
| 3 | 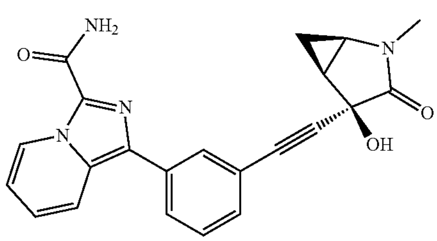 [SMILES: CN1C(=O)[C@](O)(C#Cc2cccc(-c3nc(C(N)=O)n4ccccc34)c2)[C@H]2C[C@H]21] |
| 4 | 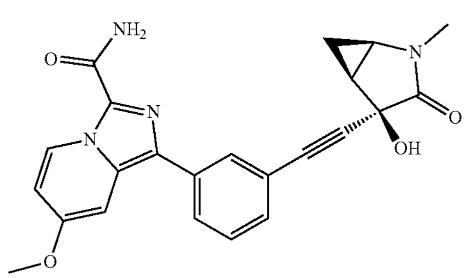 [SMILES: COc1ccn2c(C(N)=O)nc(-c3cccc(C#C[C@@]4(O)C(=O)N(C)[C@@H]5C[C@@H]54)c3)c2c1] |

TABLE 2-continued

| Compound No. | Structure |
|---|---|
| 5 | 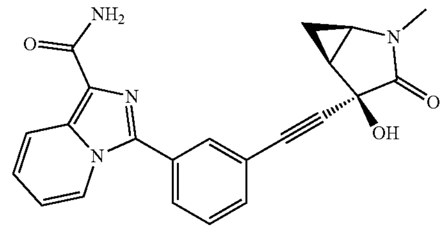 [SMILES: CN1C(=O)[C@](O)(C#Cc2cccc(-c3nc(C(N)=O)c4ccccn34)c2)[C@H]2C[C@H]21] |
| 6 | 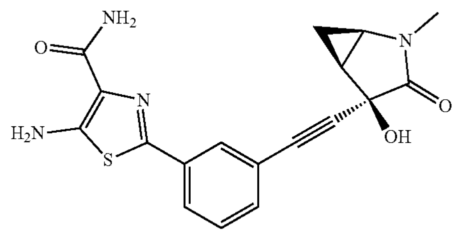 [SMILES: CN1C(=O)[C@](O)(C#Cc2cccc(-c3nc(C(N)=O)c(N)s3)c2)[C@H]2C[C@H]21] |
| C-1 | |
| C-1 | |
| C-3 | 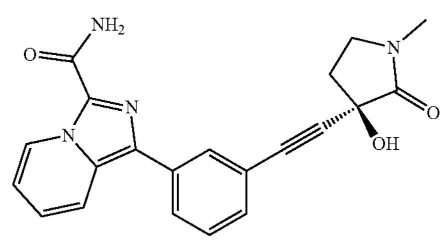 [SMILES: CN1CC[C@@](O)(C#Cc2cccc(-c3nc(C(N)=O)n4ccccc34)c2)C1=O] |
| C-4 | 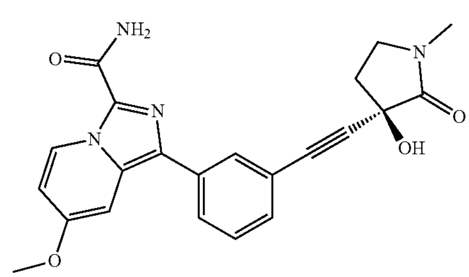 [SMILES: COc1ccn2c(C(N)=O)nc(-c3cccc(C#C[C@]4(O)CCN(C)C4=O)c3)c2c1] |

TABLE 2-continued

| Compound No. | Structure |
|---|---|
| C-5 | (structure shown) |
| C-6 | (structure shown) |

Synthesis of NIK Inhibitors

Methods for preparing intermediates and compounds of the present invention are presented in the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives or reaction conditions. In addition, many of the compounds prepared by the methods described below can be further modified in light of this disclosure using conventional chemistry well known to those skilled in the art.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or Beilstein's Handbuch der organishcen chemie, 4, Aufl. Ed. Springer-Verlag, Berlin including supplements also included via the Beilstein online database.

In preparing a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1) or (Da-2), protection of remote functionality (e.g., primary or secondary amine) of intermediates may be necessary. The need for such protection will vary depending on the nature of the remote functionality and the conditions of the preparation methods. The need for such protection is readily determined by one skilled in the art. Exemplary protecting groups are provided herein. For a general description of protecting groups and their use, see P. G. M. Wuts and T. W. Greene, Greene's Protective Groups in Organic Synthesis 4$^{th}$ edition, Wiley-Interscience, New York, 2006.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513:375-378 (1990)). Enriched or purified enantiomers can be distinguished by methods used to distinguish other chiral molecules with asymmetric carbon atoms, such as optical rotation and circular dichroism. The absolute stereochemistry of chiral centers and enantiomers can be determined by x-ray crystallography.

Positional isomers, for example E and Z forms, of compounds of formula (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2), and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are NIK kinase inhibitors, and are useful in the treatment of several diseases, for example, cancer or inflammatory conditions.

The invention also provides for compositions and medicaments comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein and at least one pharmaceutically acceptable carrier, diluent or excipient. The compositions of the invention can be used for inhibiting NF-kB signaling activity in mammals (e.g., human patients), by for example, inhibiting NIK activity.

By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein and a pharmaceutically acceptable carrier, diluent or excipient. In another embodiment, the invention provides for preparing compositions (or medicaments) comprising compounds of the invention. In another embodiment, the invention provides for administering a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein and compositions comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein to a mammal (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NIK activity as required to prevent or treat the undesired disease or disorder, such as for example, neurodegeneration, amyloidosis, formation of neurofibrillary tangles, or undesired cell growth (e.g., cancer cell growth). For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, such as 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compositions comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); or non-ionic surfactants such as TWEEN™, PLURONICS™ or polyethylene glycol (PEG). A active pharmaceutical ingredient of the invention (e.g., a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention can be prepared. Suitable examples of sustained-release preparations include semipermeable matrices of solid hydrophobic polymers containing a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) may be formulated by mixing at ambient temperature at the appropriate pH, and at the desired degree of purity, with physiologically acceptable carriers. The pH of the formulation depends mainly on the particular use and the concentration of compound, but typically ranges anywhere from about 3 to about 8. In one example, a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein is formulated in an acetate buffer, at pH 5. In another embodiment, the compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) are sterile. The compound may be stored, for example, as a solid or amorphous composition, as a lyophilized formulation or as an aqueous solution.

Formulations of a compound of the invention suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention, or any range derivable therein, compounded with about 5-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g., a phosphate buffer, adding a tonicifier, e.g., a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Indications and Methods of Treatment

The compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2), inhibit the activity of NIK. Accordingly, in another aspect of the invention the compounds of the invention can be used for the treatment of diseases and disorders in a mammal, for example a human patient, in which the inhibition of NIK in the patient would be therapeutically effective. For example, the compounds of the invention are useful for the treatment of diseases or disorders in a mammal (e.g., a human patient) associated with over-active or undesired NF-kB signaling through, for example, the over-activation of NIK. In one embodiment, the compounds of the invention are used to inhibit the activity of NIK, for example in an in vitro assay setting, by contacting said compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein with NIK. For example, compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) can be used as a control compound in an in vitro assay setting.

In another embodiment, the compounds of the invention are used to inhibit the undesired signaling of NF-kB, e.g., in an cell proliferation assay, by introducing into a cell a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein. In another embodiment, the present invention provides the treatment of diseases or disorders in a mammal (e.g., human patient) associated with over-active or undesired NF-kB signaling (e.g., cancer, inflammatory diseases, among others) said method comprising administering to a mammal (e.g., a human patient) in need thereof a therapeutically effective amount of a compound of the invention.

Diseases and disorders treatable according to the methods of this invention include, cancer, inflammatory conditions, fibrotic conditions, autoimmune disease and proliferation induced after medical procedures (e.g., arthritis, graft rejection, inflammatory bowel disease, cell proliferation induced after surgery angioplasty, among others). In one embodiment, a mammal (e.g., a human patient) is treated with a compound of the invention and a pharmaceutically acceptable carrier, adjuvant, or vehicle, wherein said compound of the invention is present in an amount to inhibit NF-kB signaling through, for example, but not limited to, inhibition of NIK.

In one embodiment, a compound of the invention can be used in the treatment of cell proliferative disorders.

In one embodiment of the invention, cancers that may be treated by the compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) are selected from the group consisting of Lung (bronchogenic carcinoma (non-small cell lung); Gastrointestinal—rectal, colorectal and colon; Genitourinary tract—kidney (papillary renal cell carcinoma); and skin—head and neck squamous cell carcinoma.

In one embodiment, compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) can be used for the treatment of a cancer selected from the group consisting of head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancers, colon cancer, leukemias, lymphomas, multiple myeloma, glioblastomas and breast carcinoma.

In one embodiment, compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) can be used for the treatment of a cancer selected from the group consisting of histiocytic lymphoma, lung adenocarcinoma, small cell lung cancer, pancreatic cancer, liver cancer, gastric cancer, colon cancer, leukemias, lymphomas, multiple myeloma, glioblastomas and breast carcinoma.

In one embodiment, compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) can be used for the treatment of cancer selected from the group consisting of lymphomas, leukemias and multiple myeloma.

In one embodiment, the invention provides for the preparation of a medicament comprising a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the treatment of lymphoma, leukemia or multiple myeloma.

In one embodiment, the invention provides for the treatment of lymphoma, leukemia or multiple myeloma, which method comprises administering an effective amount of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein.

In one embodiment, compounds of the invention are useful for the treatment of inflammatory diseases and conditions including, but not limited to, lupus (including systemic lupus erythematosus, extra-renal lupus and lupus nephritis), asthma, COPD, rhinitis, multiple sclerosis, IBD, arthritis, gastritis, rheumatoid arthritis, dermatitis, endometriosis, transplant rejection, cardiac infarction, Alzheimer's diseases, diabetes Type II, inflammatory bowel disease, sepsis, arthrosclerosis, and atherosclerosis.

In one embodiment, the invention provides for the use of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the treatment of an inflammatory condition.

In one embodiment, the invention provides for the use of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the preparation of a medicament for the treatment of an inflammatory condition.

In one embodiment, the invention provides for a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the treatment of an inflammatory condition.

In one embodiment, the invention provides for a method for the treatment of an inflammatory condition, which method comprises administering an effective amount of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein to a patient in need thereof.

In one embodiment, the invention provides for the treatment of an inflammatory condition selected from the group consisting of lupus (including systemic lupus erythematosus, extra-renal lupus and lupus nephritis), COPD, rhinitis, multiple sclerosis, IBD, arthritis, rheumatoid arthritis, dermatitis, endometriosis and transplant rejection, which method comprises administering an effective amount of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein.

In one embodiment, compounds of the invention are useful for the treatment of fibrotic diseases and conditions including, but not limited to, fibrosis, endomyocardial fibrosis, pulmonary fibrosis, pulmonary fibrosis secondary to sclerosis, cystic fibrosis, idiopathic pulmonary fibrosis and hepatic fibrosis.

In one embodiment, the invention provides for the use of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the treatment of a fibrotic condition.

In one embodiment, the invention provides for the use of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the preparation of a medicament for the treatment of a fibrotic condition.

In one embodiment, the invention provides for a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein for the treatment of an inflammatory condition.

In one embodiment, the invention provides for a method for the treatment of a fibrotic condition, which method comprises administering an effective amount of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein to a patient in need thereof.

In one embodiment, the invention provides for the treatment of a fibrotic selected from the group consisting of fibrosis, endomyocardial fibrosis, pulmonary fibrosis, pulmonary fibrosis secondary to sclerosis, cystic fibrosis, idiopathic pulmonary fibrosis and hepatic fibrosis, which method comprises administering an effective amount of a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein.

Combinations

The compounds of formulae (I), (II), (A), (Aa), (Aa-1), (Aa-2), (B), (Ba), (Ba-1), (Ba-2), (C), (Ca), (Ca-1), (Ca-2), (D), (Da), (Da-1) and (Da-2) may be employed alone or in combination with other therapeutic agents for treatment. In one embodiment, compounds of this invention may be employed alone or in combination with chemotherapeutic agents. In one embodiment, compounds of this invention may be employed alone or in combination with anti-inflammatory agents. In one embodiment, compounds of this invention may be employed alone or in combination with anti-fibrotic agents. The compounds of the present invention can be used in combination with one or more additional drugs, for example an anti-inflammatory compound, an anti-fibrotic compound or anti-cancer compounds, that work by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein is combined in a pharmaceutical combination formulation, or dosing regimen as combination therapy, with a second therapeutic compound that has anti-inflammatory, anti-fibrotic or anti-cancer properties or that is useful for treating an inflammation, fibrotic condition, immune-response disorder, or hyperproliferative disorder (e.g., cancer). The second therapeutic agent may be a NSAID (Non-Steroidal Anti-Inflammatory Drug) or other anti-inflammatory agent. The second therapeutic agent may be an anti-fibrotic agent. The second therapeutic agent may be a chemotherapeutic agent. In one embodiment, a pharmaceutical composition of this invention comprises a compound of formula (I), (II), (A), (Aa), (Aa-1), (Aa-2), (B), (Ba), (Ba-1), (Ba-2), (C), (Ca), (Ca-1), (Ca-2), (D), (Da), (Da-1), (Da-2), or any variation thereof detailed herein in combination with a therapeutic agent such as an NSAID.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

In some cases, stereoisomers are separated to give single enantiomers or diastereomers as single, unknown stereoisomers, and are arbitrarily drawn as single isomers. Where appropriate, information is given on separation method and elution time and order.

Example A

Synthesis of 4-ethynyl-4-hydroxy-2-methyl-2-azabicyclo[3.1.0]hexan-3-one

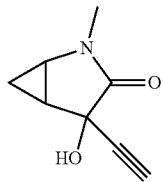

Step 1: Synthesis of tert-butyl 2-azabicyclo[3.1.0]hexane-2-carboxylate

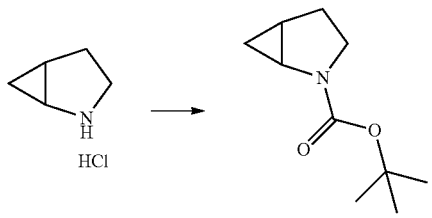

A solution of sodium carbonate in water (79 ml, 79 mmol, 1 mol/l) and solution of di-tert-butyl dicarbonate (9060 mg, 41.5 mmol) in 10 ml of tetrahydrofuran was added dropwise simultaneously to a solution of 2-aza-bicyclo[3.1.0]hexane hydrochloride (4410 mg, 36.9 mmol) in a mixture of water and tetrahydrofuran (1:1, 90 ml). The mixture was stirred for 2 hours, extracted with ethyl acetate, the organic extracts were washed with water, brine, dried over magnesium sulfate and concentrated. The residue was purified on a 40 g silica gel column eluting with 20% of ethyl acetate in heptane to give 6230 mg (92%) of the title compound. LC-MS (ES, m/z): 367 [2M+H]$^+$.

Step 2: Synthesis of tert-butyl 3-oxo-2-azabicyclo[3.1.0]hexane-2-carboxylate

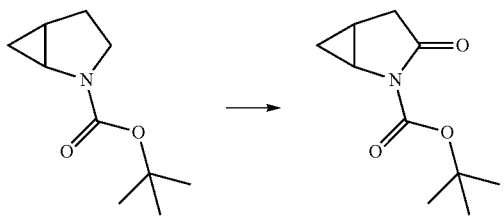

A solution of dioxoruthenium hydrate (2055 mg, 13.6 mmol) and sodium periodate (36.4 g, 170 mmol) in 500 ml of water was added portionwise to a mixture of tert-butyl 4-azabicyclo[3.1.0]hexane-4-carboxylate (6230 mg, 34.0 mmol) in 650 ml of ethyl acetate. The mixture was vigorously stirred for 20 h. The black precipitate was filtered out, the filtrate mixed with 250 ml of 5% aqueous $Na_2S_2O_3$ and organic layer separated. The organic extracts were washed with water, brine, dried over $MgSO_4$ and concentrated. The residue—heavy oil—solidified upon standing to give 5557 mg (83%) of the title compound. LC-MS (ES, m/z): 142 [M-i-Butylene+H]$^+$. $^1$H NMR (400 MHz, Chloroform-d) δ 3.61-3.53 (m, 1H), 2.94-2.84 (m, 1H), 2.52 (dt, J=18.8, 1.1 Hz, 1H), 1.55 (s, 9H), 1.52-1.46 (m, 1H), 1.06-0.96 (m, 1H), 0.49-0.40 (m, 1H).

Step 3: Synthesis of 2-azabicyclo[3.1.0]hexan-3-one

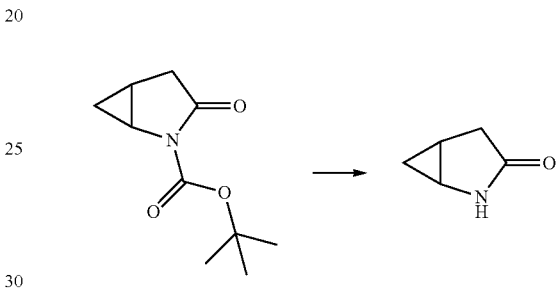

A solution of HCl in dioxane (20 mL, 80 mmol, 4.0 mol/L) was added dropwise to a stirred solution of tert-butyl 3-oxo-4-azabicyclo[3.1.0]hexane-4-carboxylate (1973 mg, 10.0 mmol) in 40 ml of dichloromethane. The stirring continued for 2 hours after $CO_2$ ceased to evolve. The reaction mixture was concentrated in vacuum, the residue redissolved in dichloromethane and concentrated again. The operation was repeated two more times to give 946 mg (97%) of the title compound. LC-MS (ES, m/z): 195 [2M+H]$^+$.

Step 4: Synthesis of 2-methyl-2-azabicyclo[3.1.0]hexan-3-one

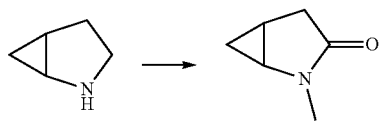

A mixture of 4-azabicyclo[3.1.0]hexan-3-one (900 mg, 9.3 mmol) and cesium carbonate (5120 mg, 15.7 mmol) in acetonitrile (40 ml) was stirred for 15 min and then iodomethane (0.87 ml, 14 mmol) was added to the suspension. The mixture was heated at 70-80° C. in a sealed vial for 12 hours. The resulting mixture was cooled to the ambient temperature and filtered. The filtrate was concentrated in vacuum to give 873 mg (85%) of the title compound. LC-MS (ES, m/z): 223 [2M+H]$^+$. $^1$H NMR (400 MHz, Chloroform-d) δ 3.04-2.95 (m, 1H), 2.90 (s, 3H), 2.83-2.72 (m, 1H), 2.36 (dt, J=17.8, 1.1 Hz, 1H), 1.55-1.45 (m, 1H), 0.90-0.83 (m, 1H), 0.34-0.31 (m, 1H).

Step 5: Synthesis of 4-hydroxy-2-methyl-2-azabicyclo[3.1.0]hexan-3-one

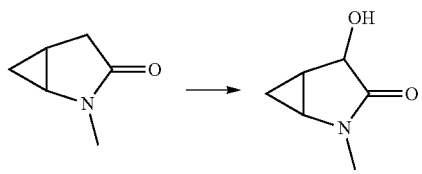

Lithium bis(trimethylsilyl)amide in tetrahydrofuran (7.5 ml, 7.5 mmol, 1 mol/l) was added dropwise to a mixture of 4-methyl-4-azabicyclo[3.1.0]hexan-3-one (556 mg, 5.0 mmol) and bis(trimethylsilyl)peroxide (3.3 ml, 15 mmol) in tetrahydrofuran (15 ml) at −76° C. The mixture was stirred at this temperature for 1 hour, allowed to warm up to −30° C. and left at this temperature for 1 hour. The mixture was quenched with 1 M aqueous HCl and stirred for 30 min. The resulting mixture was extracted with pentane 3 times. The aqueous layer was neutralized to pH 7 by addition of saturated aqueous NaHCO$_3$ and concentrated in vacuum to dryness. The dry residue was extracted with dichloromethane, filtered and the filtrate concentrated to give 498 mg (78%) of the title compound as a yellowish oil crystallizing upon standing. LC-MS (ES, m/z): 255 [2M+H]$^+$, 128 [M+H]$^+$. $^1$H NMR (400 MHz, Chloroform-d) δ 4.86 (d, J=4.3 Hz, 1H), 4.17 (dd, J=4.3, 1.6 Hz, 1H), 3.12-3.01 (m, 1H), 2.91 (s, 3H), 1.72-1.63 (m, 1H), 1.02-0.92 (m, 1H), 0.39-0.31 (m, 1H).

Step 6: Synthesis of 2-methyl-2-azabicyclo[3.1.0]hexane-3,4-dione

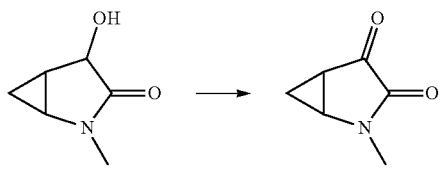

Dess-Martin periodinane (1994 mg, 4.7 mmol) was added portionwise to a solution of 2-hydroxy-4-methyl-4-azabicyclo[3.1.0]hexan-3-one (498 mg, 3.9169 mmol) in dichloromethane (25 ml). The mixture was stirred at ambient temperature for 1 hour. The resulting mixture was concentrated in vacuum, the residual acetic acid was coevaporated with heptane twice, and the semisolid residue was redissolved in dichloromethane, filtered and loaded on a 24 g column eluting with 0-100% gradient of ethyl acetate in heptane to give 320 mg (65%) of a title compound. LC-MS (ES, m/z): 251 [2M+H]$^+$, 126 [M+H]$^+$. $^1$H NMR (400 MHz, Chloroform-d) δ 3.72-3.66 (m, 1H), 3.11 (s, 3H), 2.36-2.27 (m, 1H), 1.64-1.55 (m, 1H), 1.55-1.48 (m, 1H).

Step 7: Synthesis of 4-ethynyl-4-hydroxy-2-methyl-2-azabicyclo[3.1.0]hexan-3-one

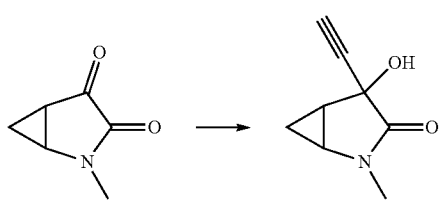

A solution of 4-methyl-4-azabicyclo[3.1.0]hexane-2,3-dione (318 mg, 2.5 mmol) in 8 ml of tetrahydrofuran was added dropwise to a bromo(ethynyl)magnesium (10.0 mL, 5 mmol, 0.5 mol/L) in tetrahydrofuran at −76° C. The mixture was stirred for 1 hour. The mixture was quenched with 5 ml of saturated aqueous NH$_4$Cl and after warming to ambient temperature extracted four times with 10 ml of ethyl acetate. The organic extracts were dried with MgSO$_4$ and concentrated to give 213 mg (55%) of the title compound as mixture of diastereomers (3:1 by NMR). LC-MS (ES, m/z): 303 [2M+H]$^+$, 152 [M+H]$^+$.

Example A-bis

Alternate Synthesis of 4-ethynyl-4-hydroxy-2-methyl-2-azabicyclo[3.1.0]hexan-3-one

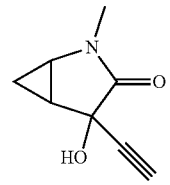

Step 1: Synthesis of 2-chloro-N-cyclopropyl-N-methylacetamide

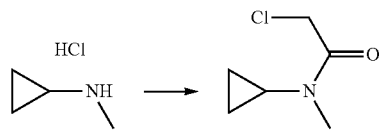

To a 5000-mL 4-necked round-bottom flask purged and maintained with an inert atmosphere of nitrogen was placed a solution of N-methylcyclopropanamine hydrochloride (90 g, 836.57 mmol, 1.00 equiv) in dichloromethane (3000 mL) followed by the addition of triethylamine (295.9 g, 2.92 mol, 3.50 equiv) dropwise with stirring in an ice/salt bath. To this was added 2-chloroacetyl chloride (103.2 g, 913.74 mmol, 1.10 equiv) dropwise with stirring at −20° C. The resulting solution was stirred overnight at 25° C. The reaction mixture was cooled with a water/ice bath and then quenched by the addition of 1000 mL of water. The resulting solution was extracted with 2×1000 mL of dichloromethane. The organic layers were combined, dried over anhydrous sodium sulfate and concentrated under vacuum. The residue was applied onto a silica gel column eluted with ethyl acetate/petroleum ether (1:5) to afford 110 g (89%) of 2-chloro-N-cyclopropyl-N-methylacetamide as light yellow oil. $^1$H NMR (300 MHz, Chloroform-d) δ 4.32 (s, 2H), 2.98 (s, 3H), 2.84-2.72 (m, 1H), 0.97-0.84 (m, 4H).

Step 2: Synthesis of 2-methyl-2-azabicyclo[3.1.0]hexan-3-one

To a 3000-mL 4-necked round-bottom flask purged and maintained with an inert atmosphere of argon was placed 2-chloro-N-cyclopropyl-N-methylacetamide (22.2 g, 150.40 mmol, 1.00 equiv), bis(dibenzylideneacetone)palladium(0) (2.6 g, 4.48 mmol, 0.03 equiv), (3aR,8aR)-4,4,8,8-tetrakis (3,5-di-tert-butylphenyl)-2,2-dimethyl-6-phenyltetrahydro-[1,3]dioxolo[4,5-e][1,3,2]dioxaphosphepine (9.2 g, 9.02 mmol, 0.06 equiv), adamantane-1-carboxylic acid (810 mg, 4.49 mmol, 0.03 equiv), Cs$_2$CO$_3$ (73.5 g, 225 mmol, 1.50 equiv), 4 Å molecular sieves (22.2 g) and toluene (1500 mL). The resulting mixture was stirred overnight at 70° C. in an oil bath. This reaction was repeated 3 times. The reaction mixture was cooled to room temperature. The solids were filtered out and washed with 1×2 L of ethyl acetate. The filtrate was concentrated under vacuum. The crude product was purified by distillation under reduced pressure (10 mm Hg) and the fraction was collected at 80° C. to afford 51 g (76%) of 2-methyl-2-azabicyclo[3.1.0]hexan-3-one as light yellow liquid. $^1$H NMR (300 MHz, Chloroform-d) δ 2.99-2.96 (m, 1H), 2.92 (s, 3H), 2.74-2.70 (m, 1H), 2.35 (d, J=18.0, 1H), 1.52-1.43 (m, 1H), 0.89-0.85 (m, 1H), 0.32-0.29 (m, 1H).

Step 3: Synthesis of 2-methyl-4,4-bis(methylthio)-2-azabicyclo[3.1.0]hexan-3-one

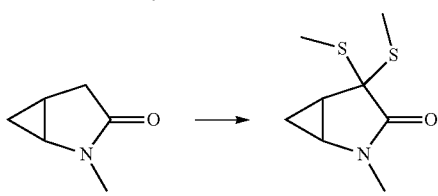

To a 1000-mL 3-necked round-bottom flask purged and maintained with an inert atmosphere of argon was placed 2-methyl-2-azabicyclo[3.1.0]hexan-3-one (11 g, 98.97 mmol, 1.00 equiv) and tetrahydrofuran (500 mL) followed by the addition of lithium diisopropylamide (75 mL, 1.50 equiv) dropwise with stirring at −30° C. in 1 hour. To this was added (methanesulfonylsulfanyl)methane (19 g, 150.56 mmol, 1.50 equiv) dropwise with stirring at −30° C. in 2 hours. The resulting solution was stirred overnight at 25° C. This reaction was repeated for 3 times. The reaction mixture was cooled with a water/ice bath and then quenched by the addition of 800 mL of saturated aqueous NH$_4$Cl. The resulting solution was extracted with 3×1000 mL of ethyl acetate and the organic layers were combined, dried over anhydrous sodium sulfate and concentrated under vacuum. The residue was applied onto a silica gel column eluted with ethyl acetate/petroleum ether (1:10) to afford 44 g (55%) of 2-methyl-4,4-bis(methylsulfanyl)-2-azabicyclo[3.1.0] hexan-3-one as yellow oil. $^1$H NMR (300 MHz, Chloroform-d) δ 3.21-3.14 (m, 1H), 2.91 (s, 3H), 2.32 (s, 3H), 2.24 (s, 3H), 2.70-2.62 (m, 1H), 1.04-0.97 (m, 1H), 0.79-0.82 (m, 1H).

Step 4: Synthesis of 2-methyl-2-azabicyclo[3.1.0] hexane-3,4-dione

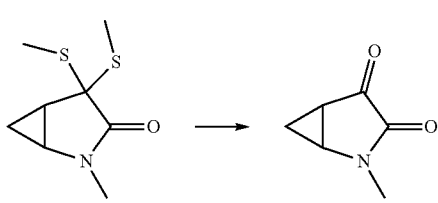

To a 3-L 4-necked round-bottom flask purged and maintained with an inert atmosphere of nitrogen was placed 2-methyl-4,4-bis(methylsulfanyl)-2-azabicyclo[3.1.0] hexan-3-one (22 g, 108.20 mmol, 1.00 equiv) and acetonitrile (2000 mL), water (200 mL) followed by the addition of (bis(trifluoroacetoxy)iodo)benzene (92.9 g, 216.03 mmol, 2.00 equiv) in portions. The resulting solution was stirred for 2 hours at 0° C. in an ice/salt bath. This reaction was repeated once. The reaction was then quenched by the addition of 1000 mL of saturated aqueous NaHCO$_3$. The resulting solution was extracted with 4×1 L of chloroform and the organic layers were combined and dried over anhydrous sodium sulfate and concentrated under vacuum. The residue was applied onto a silica gel column eluted with ethyl acetate/petroleum ether (4:1) to afford 19 g (70%) of 2-methyl-2-azabicyclo[3.1.0]hexane-3,4-dione as a light yellow solid. $^1$H NMR (300 MHz, Chloroform-d) δ 3.75-3.69 (m, 1H), 3.14 (s, 3H), 2.38-2.32 (m, 1H), 1.66-1.53 (m, 2H).

Step 5: Synthesis of 4-ethynyl-4-hydroxy-2-methyl-2-azabicyclo[3.1.0]hexan-3-one

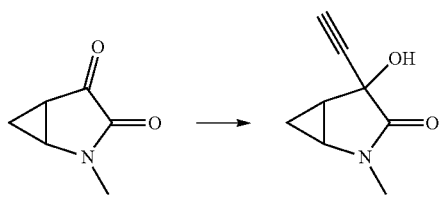

To a 1000-mL 3-necked round-bottom flask purged and maintained with an inert atmosphere of argon was placed bromo(ethynyl)magnesium (0.5 M) (256 mL) followed by the addition of a solution of 2-methyl-2-azabicyclo[3.1.0] hexane-3,4-dione (8 g, 63.94 mmol, 1.00 equiv) in tetrahydrofuran (200 mL) dropwise with stirring at −78° C. and then stirred for 1 hour at the same temperature. The resulting solution was stirred for 4 hours at −78 to 0° C. in a liquid nitrogen bath. This reaction was repeated once. The reaction mixture was cooled to −30° C. The reaction was then quenched by the addition of 400 mL of saturated aqueous NH$_4$Cl. The resulting solution was extracted with 3×500 mL of ethyl acetate and the organic layers were combined, dried over anhydrous sodium sulfate and concentrated under vacuum. The residue was applied onto a silica gel column eluted with ethyl acetate/petroleum ether (4:1). The crude product was purified by re-crystallization from ethyl acetate to afford 17 g (88%) of 4-ethynyl-4-hydroxy-2-methyl-2-azabicyclo[3.1.0]hexan-3-one as a light yellow solid. LC-MS (ES, m/z): 303 [2M+H]$^+$, 152 [M+H]$^+$.

Examples 1 and 2

Synthesis of 1-(3-(((1R,4R,5S)-4-hydroxy-2-methyl-3-oxo-2-azabicyclo[3.1.0]hexan-4-yl)ethynyl)phenyl)-1H-pyrazolo[3,4-b]pyridine-3-carboxamide

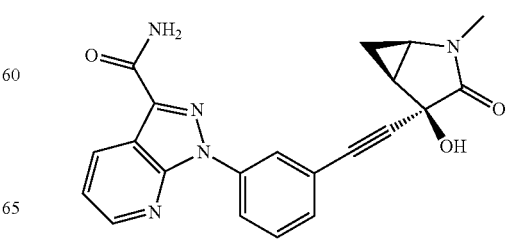

and

-continued

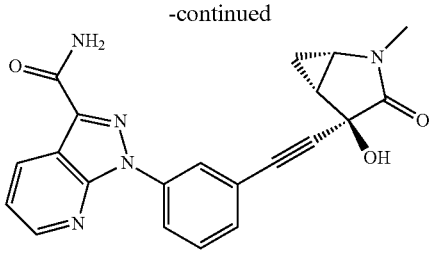

Step 1: Synthesis of methyl 1-(3-((4-hydroxy-2-methyl-3-oxo-2-azabicyclo[3.1.0]hexan-4-yl)ethynyl)phenyl)-1H-pyrazolo[3,4-b]pyridine-3-carboxylate

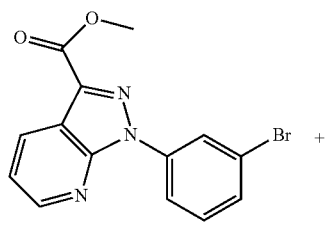

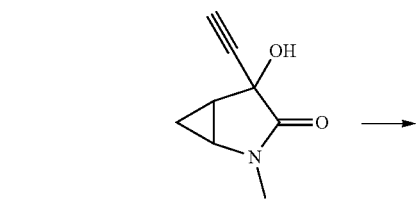

A mixture of methyl 1-(3-bromophenyl)pyrazolo[3,4-b]pyridine-3-carboxylate (see WO2015/025025) (150 mg, 0.45 mmol), 2-ethynyl-2-hydroxy-4-methyl-4-azabicyclo[3.1.0]hexan-3-one (106 mg, 0.70 mmol), bis(triphenylphosphine)palladium(II) chloride (51 mg, 0.07 mmol) and triethylamine (0.39 mL, 2.8 mmol) in dimethylsulfoxide (10 ml) was degassed and heated in a sealed vial at 95° C. for 1 hour. The mixture was mixed with water and extracted with ethyl acetate. The organic extracts were washed with 1% aqueous citric acid, water, brine, dried over MgSO$_4$ and concentrated. The residue was purified on a 12 g silica gel column eluting with 0-100% gradient of ethyl acetate in heptane to give 143 mg (79%) of the title compound as a mixture of diastereomers. LC-MS (ES, m/z): 403 [M+H]$^+$.

Step 2: Synthesis of 1-(3-((4-hydroxy-2-methyl-3-oxo-2-azabicyclo[3.1.0]hexan-4-yl)ethynyl)phenyl)-1H-pyrazolo[3,4-b]pyridine-3-carboxamide

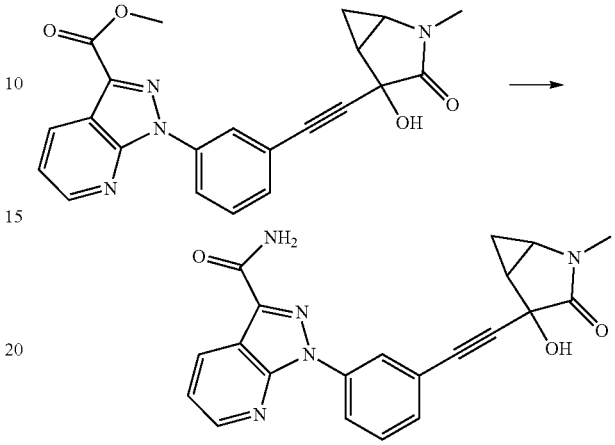

A mixture of methyl 1-[3-[2-(2-hydroxy-4-methyl-3-oxo-4-azabicyclo[3.1.0]hexan-2-yl)ethynyl]phenyl]pyrazolo[3,4-b]pyridine-3-carboxylate (143 mg, 0.36 mmol) and 6 ml of sat. ammonia in methanol was heated in a sealed vial at 60° C. for 12 hours. The resulting mixture was concentrated, the residue redissolved in methanol and concentrated again to give 134 mg (97%) of the title compound as a mixture of diastereomers. LC-MS (ES, m/z): 388 [M+H]$^+$.

Step 3: Isolation of 1-(3-(((1R,4R,5S)-4-hydroxy-2-methyl-3-oxo-2-azabicyclo[3.1.0]hexan-4-yl)ethynyl)phenyl)-1H-pyrazolo[3,4-b]pyridine-3-carboxamide

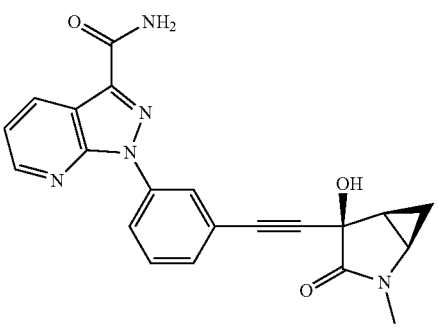

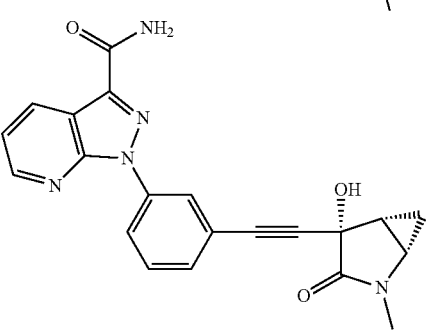

-continued

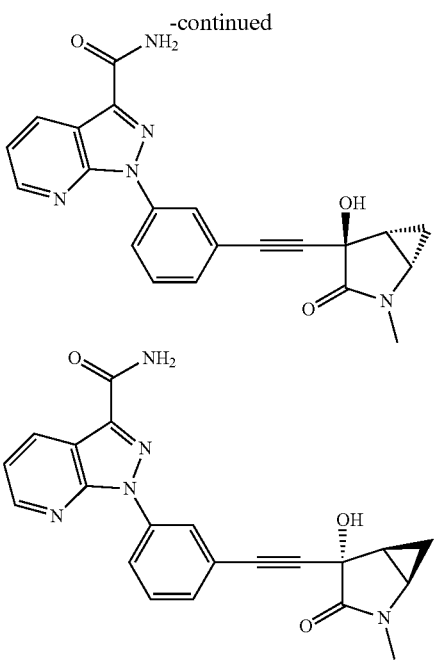

A mixture of diastereomers was subjected to a chiral separation by supercritical fluid chromatography (SFC) to afford the four individual isomers.

SFC preparative conditions: Instrument: SFC PICLab PREP 100 (PIC 100 SFC); Column: Chiralpak AD (150×21.1 mm, 5 m); Method: Isocratic (45% Mobile Phase B); Mobile Phase A: carbon dioxide; Mobile Phase B: Ethanol with 0.1% NH$_4$OH; Flow rate: 70 mL/min; Pressure: 100 bars; Temperature: 40° C.

Compound 1: 1-(3-(((1R,4R,5S)-4-hydroxy-2-methyl-3-oxo-2-azabicyclo[3.1.0]hexan-4-yl)ethynyl)phenyl)-1H-pyrazolo[3,4-b]pyridine-3-carboxamide (31.7 mg, 23.7%). LC-MS (ES, m/z): 388 [M+H]$^+$. $^1$H NMR (400 MHz, DMSO-d$_6$) δ 8.78 (dd, J=4.6, 1.7 Hz, 1H), 8.67 (dd, J=8.1, 1.7 Hz, 1H), 8.53-8.48 (m, 2H), 8.25 (s, 1H), 7.71 (s, 1H), 7.64 (td, J=7.9, 0.8 Hz, 1H), 7.52 (dd, J=8.1, 4.5 Hz, 1H), 7.49-7.45 (m, 1H), 6.47 (s, 1H), 3.38-3.33 (m, 1H), 2.82 (s, 3H), 2.10-2.02 (m, 1H), 0.86 (ddd, J=8.4, 5.8, 4.7 Hz, 1H), 0.64 (ddd, J=5.8, 4.7, 2.4 Hz, 1H). Supercritical Fluid Chromatography analytical conditions: Instrument: Waters ACQUITY UPC2 System (Waters UPC2); Column: Chiralpak AD (50×4.6 mm, 3 μm); Method: Isocratic (40% Mobile Phase B); Mobile Phase A: carbon dioxide; Mobile Phase B: Ethanol with 0.1% NH$_4$OH; Flow rate: 4 mL/min; Pressure: 120 bars; Temperature: 40° C.; Retention time: 1.20 min. This is the most potent NIK enzyme inhibitor among the 4 stereoisomers. The absolute stereo configuration was confirmed by X-ray crystallography of a co-crystal with a protein.

Compound 2: 1-(3-(((1S,4R,5R)-4-hydroxy-2-methyl-3-oxo-2-azabicyclo[3.1.0]hexan-4-yl)ethynyl)phenyl)-1H-pyrazolo[3,4-b]pyridine-3-carboxamide (12.4 mg, 9.3%). LC-MS (ES, m/z): 388 [M+H]$^+$. $^1$H NMR (400 MHz, DMSO-d6) δ 8.78 (dd, J=4.5, 1.7 Hz, 1H), 8.67 (dd, J=8.1, 1.7 Hz, 1H), 8.52-8.45 (m, 2H), 8.25 (s, 1H), 7.71 (s, 1H), 7.67-7.60 (m, 1H), 7.51 (dd, J=8.1, 4.5 Hz, 1H), 7.45 (dt, J=7.7, 1.3 Hz, 1H), 6.86 (s, 1H), 3.29 (dd, J=4.6, 2.2 Hz, 1H), 2.85 (s, 3H), 1.89 (ddd, J=8.8, 6.7, 4.8 Hz, 1H), 1.06 (ddd, J=8.8, 6.0, 4.8 Hz, 1H), 0.52 (ddd, J=6.0, 4.8, 2.3 Hz, 1H). SFC analytical conditions: Instrument: Waters ACQUITY UPC2 System (Waters UPC2); Column: Chiralpak AD (50×4.6 mm, 3 μm); Method: Isocratic (40% Mobile Phase B); Mobile Phase A: carbon dioxide; Mobile Phase B: Ethanol with 0.1% NH$_4$OH; Flow rate: 4 mL/min; Pressure: 120 bars; Temperature: 40° C.; Retention time: 0.83 min. This is the second most potent NIK enzyme inhibitor among the 4 stereoisomers. The absolute stereo configuration was confirmed by X-ray crystallography of a co-crystal with a protein.

1-(3-(((1 S,4S,5R)-4-hydroxy-2-methyl-3-oxo-2-azabicyclo[3.1.0]hexan-4-yl)ethynyl)phenyl)-1H-pyrazolo[3,4-b]pyridine-3-carboxamide (32.3 mg, 24.1%). LC-MS (ES, m/z): 388 [M+H]$^+$. $^1$H NMR (400 MHz, DMSO-d6) δ 8.78 (dd, J=4.6, 1.7 Hz, 1H), 8.67 (dd, J=8.1, 1.7 Hz, 1H), 8.54-8.47 (m, 2H), 8.26 (s, 1H), 7.71 (s, 1H), 7.64 (td, J=7.9, 0.8 Hz, 1H), 7.52 (dd, J=8.1, 4.5 Hz, 1H), 7.49-7.44 (m, 1H), 6.47 (s, 1H), 3.38-3.33 (m, 1H), 2.82 (s, 3H), 2.11-2.01 (m, 1H), 0.86 (ddd, J=8.4, 5.9, 4.8 Hz, 1H), 0.64 (ddd, J=5.8, 4.7, 2.4 Hz, 1H). SFC analytical conditions: Instrument: SFC PICLab PREP 100 (PIC 100 SFC); Column: Chiralpak AD (150×21.1 mm, 5 μm); Method: Isocratic (45% Mobile Phase B); Mobile Phase A: carbon dioxide; Mobile Phase B: Ethanol with 0.1% NH$_4$OH; Flow rate: 70 mL/min; Pressure: 100 bars; Temperature: 40° C.; Retention time: 1.51 min. This stereoisomer showed no measurable inhibition for the NIK enzyme. The absolute stereo configuration was confirmed by X-ray crystallography of a single crystal.

1-(3-(((1R,4S,5S)-4-hydroxy-2-methyl-3-oxo-2-azabicyclo[3.1.0]hexan-4-yl)ethynyl)phenyl)-1H-pyrazolo[3,4-b]pyridine-3-carboxamide (11.3 mg, 8.43%). LC-MS (ES, m/z): 388 [M+H]$^+$. $^1$H NMR (400 MHz, DMSO-d6) δ 8.78 (dd, J=4.5, 1.7 Hz, 1H), 8.67 (dd, J=8.1, 1.7 Hz, 1H), 8.52-8.45 (m, 2H), 8.25 (s, 1H), 7.71 (s, 1H), 7.67-7.60 (m, 1H), 7.51 (dd, J=8.1, 4.5 Hz, 1H), 7.45 (dt, J=7.7, 1.3 Hz, 1H), 6.86 (s, 1H), 3.29 (dd, J=4.6, 2.2 Hz, 1H), 2.85 (s, 3H), 1.89 (ddd, J=8.8, 6.7, 4.8 Hz, 1H), 1.06 (ddd, J=8.8, 6.0, 4.8 Hz, 1H), 0.52 (ddd, J=6.0, 4.8, 2.3 Hz, 1H). SFC analytical conditions: Instrument: SFC PICLab PREP 100 (PIC 100 SFC); Column: Chiralpak AD (150×21.1 mm, 5 μm); Method: Isocratic (45% Mobile Phase B); Mobile Phase A: carbon dioxide; Mobile Phase B: Ethanol with 0.1% NH$_4$OH; Flow rate: 70 mL/min; Pressure: 100 bars; Temperature: 40° C.; Retention time: 1.08 min. This stereoisomer showed no measurable inhibition for the NIK enzyme.

Example 3

Synthesis of 3-(3-(((1R,4R,5S)-4-hydroxy-2-methyl-3-oxo-2-azabicyclo[3.1.0]hexan-4-yl)ethynyl)phenyl)imidazo[1,5-a]pyridine-1-carboxamide

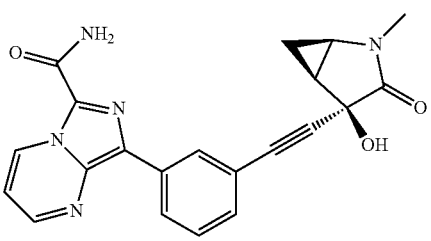 [SMILES: CN1C(=O)[C@](O)(C#Cc2cccc(-c3nc(C(N)=O)n4cccnc34)c2)[C@H]2C[C@H]21]

Step 1: Synthesis of ethyl 1-(3-(trimethylsilyl)phenyl)imidazo[1,5-a]pyridine-3-carboxylate

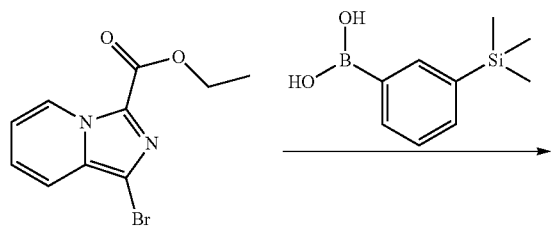

A degassed mixture of 1-bromo-imidazo[1,5-a]pyridine-3-carboxylic acid ethyl ester (200 mg, 0.743 mmol), (3-trimethylsilylphenyl)boronic acid (174 mg, 0.896 mmol), 1.0 M aqueous Cs$_2$CO$_3$ (0.75 mL, 0.75 mmol) and 1.0 M aqueous Cs$_2$CO$_3$ (0.75 mL, 0.75 mmol) in acetonitrile (6 mL) was heated at 80° C. for 3 h in a sealed vial. The mixture was diluted with water and extracted with ethyl acetate. The organic extracts were washed with water, brine, dried over MgSO$_4$ and concentrated. The residue was purified on a 24 g silica gel column eluting with 0-80% gradient of ethyl acetate in heptane to afford 163 mg (65%) of ethyl 1-(3-(trimethylsilyl)phenyl)imidazo[1,5-a]pyridine-3-carboxylate.

Step 2: Synthesis of ethyl 1-(3-iodophenyl)imidazo[1,5-a]pyridine-3-carboxylate

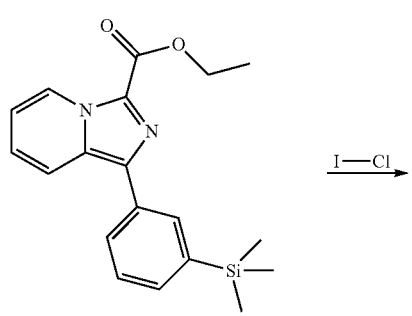

Iodochloride, 1 M in dichloromethane (D, 2.4 mL, 2.4 mmol) was added to a solution of ethyl 1-(3-trimethylsilylphenyl)imidazo[1,5-a]pyridine-3-carboxylate (163 mg, 0.482 mmol) in dichloromethane. The mixture was left for 18 hours, quenched with 5% aqueous Na$_2$S$_2$O$_5$ and extracted with ethyl acetate. The organic extracts were washed with water, brine, dried over MgSO$_4$ and concentrated. The residue was purified on a 12 g silica gel column eluting with 0-80% gradient of ethyl acetate in heptane to afford 185 mg (97%) of ethyl 1-(3-iodophenyl)imidazo[1,5-a]pyridine-3-carboxylate. LC-MS (ES, m/z): 393 [M+H]$^+$.

Step 3: Synthesis of ethyl 1-(3-((4-hydroxy-2-methyl-3-oxo-2-azabicyclo[3.1.0]hexan-4-yl)ethynyl)phenyl)imidazo[1,5-a]pyridine-3-carboxylate

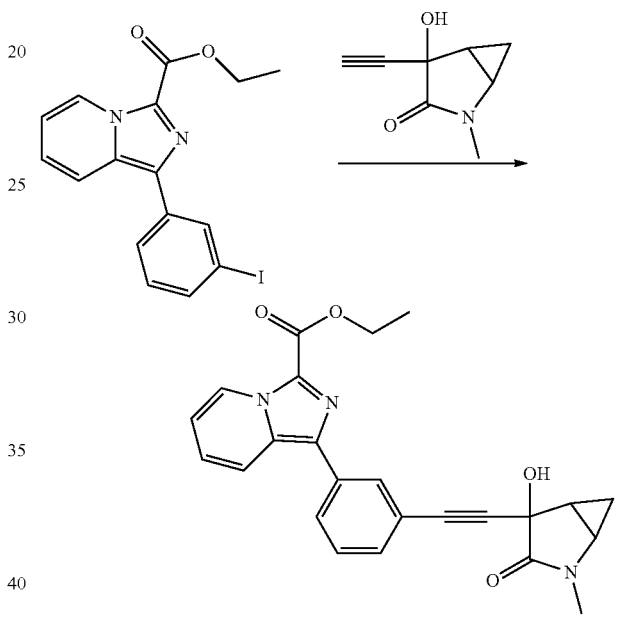

The compound was obtained by procedures similar to those described for Examples 1 and 2, Step 1 to afford 147 mg (75%) of ethyl 1-(3-((4-hydroxy-2-methyl-3-oxo-2-azabicyclo[3.1.0]hexan-4-yl)ethynyl)phenyl)imidazo[1,5-a]pyridine-3-carboxylate. LC-MS (ES, m/z): 416 [M+H]$^+$.

Step 4: Synthesis of 1-(3-((4-hydroxy-2-methyl-3-oxo-2-azabicyclo[3.1.0]hexan-4-yl) ethynyl)phenyl)imidazo[1,5-a]pyridine-3-carboxamide

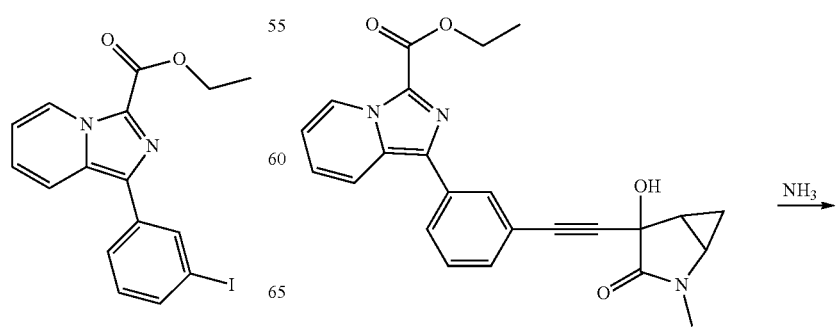

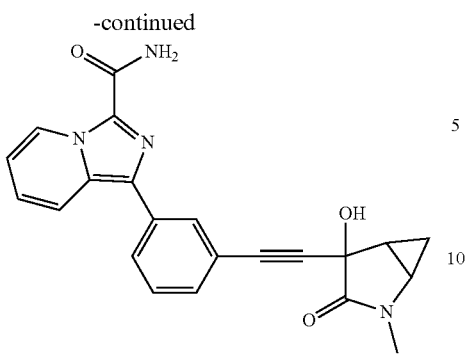

The compound was obtained by procedures similar to those described for Examples 1 and 2, step 2 to afford 133 mg (97.2%) of the title compound as a mixture of stereoisomers. The mixture was subjected to a chiral SFC separation to afford four stereoisomers:

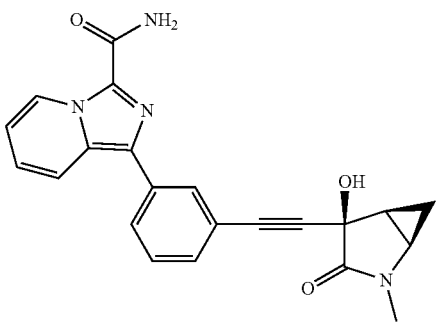

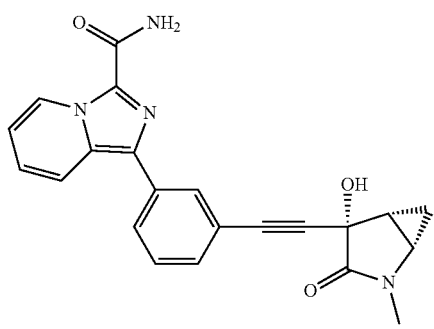

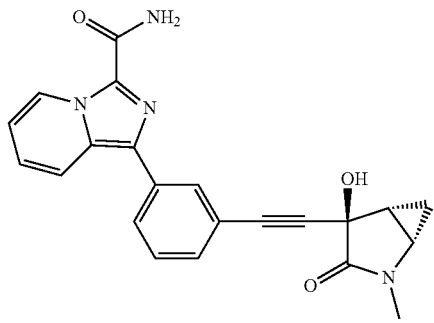

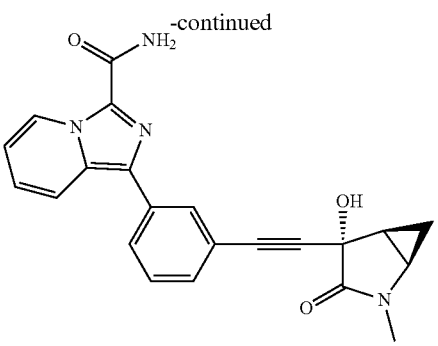

SFC preparative conditions: Instrument: SFC PICLab PREP 100 (PIC 100 SFC); Column: Chiralpak OJ (250×21.1 mm, 5 μm); Method: Isocratic (30% Mobile Phase B); Mobile Phase A: carbon dioxide; Mobile Phase B: Methanol with 0.1% NH$_4$OH; Flow rate: 70 mL/min; Pressure: 100 bars; Temperature: 40° C. The individual stereoisomers are identified by their respective physical properties (e.g. NMR data and analytical SFC retention time) and their respective absolute configurations were assigned based on NIK inhibition potency and relative yield (not confirmed by X-ray crystallography).

Compound 3: 3-(3-(((1R,4R,5S)-4-hydroxy-2-methyl-3-oxo-2-azabicyclo[3.1.0]hexan-4-yl)ethynyl)phenyl)imidazo[1,5-a]pyridine-1-carboxamide (25 mg, 18.4%). LC-MS (ES, m/z): 387 [M+H]$^+$. $^1$H NMR (400 MHz, DMSO-d6) δ 9.49 (dt, J=7.2, 1.1 Hz, 1H), 8.13 (dt, J=9.3, 1.2 Hz, 1H), 8.06 (td, J=1.7, 0.6 Hz, 2H), 8.03-7.98 (m, 1H), 7.60 (s, 1H), 7.52 (td, J=7.8, 0.6 Hz, 1H), 7.43-7.35 (m, 1H), 7.27-7.19 (m, 1H), 7.10-6.99 (m, 1H), 6.40 (s, 1H), 3.31 (s, 1H), 2.81 (s, 3H), 2.09-2.01 (m, 1H), 0.89-0.80 (m, 1H), 0.67-0.59 (m, 1H). SFC analytical conditions: Instrument: Waters ACQUITY UPC2 System (Waters UPC2); Column: Chiralpak OJ (50×4.6 mm, 3 μm); Method: Isocratic (25% Mobile Phase B); Mobile Phase A: carbon dioxide; Mobile Phase B: Methanol with 0.1% NH$_4$OH; Flow rate: 4 mL/min; Pressure: 120 bars; Temperature: 40° C.; Retention time: 0.95 min (peak 4). This is the most potent NIK enzyme inhibitor among the 4 stereoisomers.

1-(3-(((1 S,4R,5R)-4-hydroxy-2-methyl-3-oxo-2-azabicyclo[3.1.0]hexan-4-yl)ethynyl)phenyl)imidazo[1,5-a]pyridine-3-carboxamide (9.2 mg, 7.2%). Retention time 0.77 min (peak 2). LC-MS (ES, m/z): 387 [M+H]$^+$. $^1$H NMR (400 MHz, DMSO-d6) δ 9.49 (dt, J=7.3, 1.1 Hz, 1H), 8.11 (dt, J=9.3, 1.2 Hz, 1H), 8.07 (s, 1H), 8.04 (td, J=1.7, 0.5 Hz, 1H), 8.00-7.97 (m, 1H), 7.60 (s, 1H), 7.51 (td, J=7.8, 0.6 Hz, 1H), 7.38 (dt, J=7.7, 1.3 Hz, 1H), 7.25-7.20 (m, 1H), 7.08-7.02 (m, 1H), 6.79 (s, 1H), 3.30-3.25 (m, 1H), 2.84 (s, 3H), 1.94-1.84 (m, 1H), 1.11-1.01 (m, 1H), 0.55-0.48 (m, 1H). This is the second most potent NIK enzyme inhibitor among the 4 stereoisomers.

1-(3-(((1 S,4S,5R)-4-hydroxy-2-methyl-3-oxo-2-azabicyclo[3.1.0]hexan-4-yl)ethynyl)phenyl)imidazo[1,5-a]pyridine-3-carboxamide (27.2 mg, 20.0%). Retention time 0.82 min (peak 3). LC-MS (ES, m/z): 387 [M+H]$^+$. $^1$H NMR (400 MHz, DMSO-d6) δ 9.49 (dt, J=7.2, 1.1 Hz, 1H), 8.13 (dt, J=9.2, 1.2 Hz, 1H), 8.07 (td, J=1.7, 0.6 Hz, 2H), 8.03-7.98 (m, 1H), 7.60 (s, 1H), 7.52 (dt, J=7.8, 0.6 Hz, 1H), 7.39 (dt, J=7.7, 1.3 Hz, 1H), 7.27-7.19 (m, 1H), 7.09-7.01 (m, 1H), 6.40 (s, 1H), 3.38-3.31 (m, 1H), 2.81 (s, 3H), 2.09-2.02 (m, 1H), 0.89-0.81 (m, 1H), 0.67-0.59 (m, 1H). This stereoisomer showed no measurable inhibition for the NIK enzyme.

1-(3-(((1R,4S,5S)-4-hydroxy-2-methyl-3-oxo-2-azabicyclo[3.1.0]hexan-4-yl)ethynyl)phenyl)imidazo[1,5-a]pyridine-3-carboxamide (8.6 mg, 6.4%). Retention time 0.62 min (peak 1). LC-MS (ES, m/z): 387 [M+H]⁺. ¹H NMR (400 MHz, DMSO-d6) δ 9.49 (dt, J=7.2, 1.1 Hz, 1H), 8.11 (dt, J=9.3, 1.2 Hz, 1H), 8.07 (s, 1H), 8.04 (td, J=1.7, 0.6 Hz, 1H), 8.00-7.97 (m, 1H), 7.60 (s, 1H), 7.51 (td, J=7.8, 0.6 Hz, 1H), 7.38 (dt, J=7.7, 1.3 Hz, 1H), 7.26-7.19 (m, 1H), 7.08-7.02 (m, 1H), 6.79 (s, 1H), 3.30-3.25 (m, 1H), 2.84 (s, 3H), 1.93-1.84 (m, 1H), 1.10-1.01 (m, 1H), 0.55-0.47 (m, 1H). This is the third most potent NIK enzyme inhibitor among the 4 stereoisomers.

Example 4

Synthesis of 1-(3-(((1R,4R,5S)-4-hydroxy-2-methyl-3-oxo-2-azabicyclo[3.1.0]hexan-4-yl)ethynyl)phenyl)-7-methoxyimidazo[1,5-a]pyridine-3-carboxamide

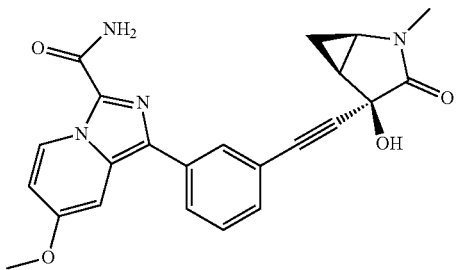 [SMILES: COc1ccn2c(C(N)=O)nc(-c3cccc(C#C[C@@]4(O)C(=O)N(C)[C@@H]5C[C@@H]54)c3)c2c1]

A mixture of stereoisomers was prepared in two steps following the same reaction sequence as Example 3, Step 1 and 2 and using ethyl 1-bromo-7-methoxyimidazo[1,5-a]pyridine-3-carboxylate as a starting material in the Step 1. The above mixture was subjected to a chiral SFC separation to afford four stereoisomers:

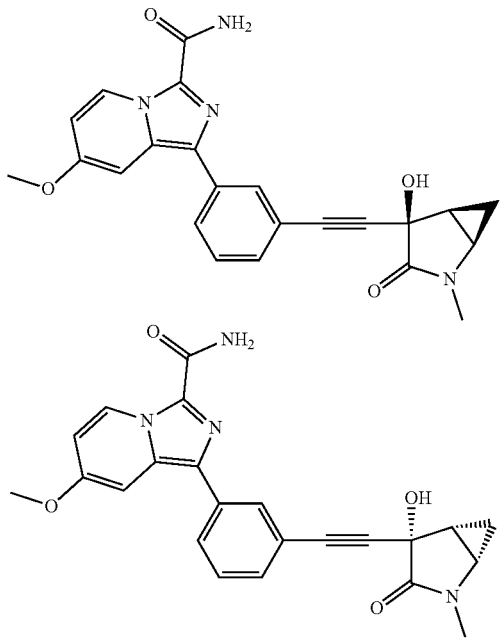

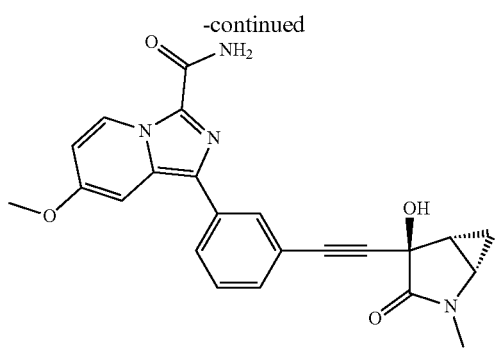

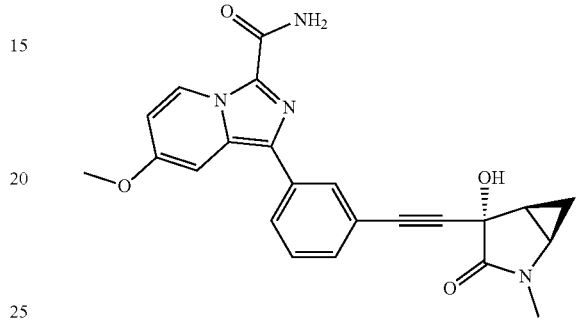

SFC preparative conditions: Instrument: SFC PICLab PREP 100 (PIC 100 SFC); Column: Chiralpak ID (150×21.1 mm, 5 μm); Method: Isocratic (45% Mobile Phase B); Mobile Phase A: carbon dioxide; Mobile Phase B: Methanol with 0.1% NH₄OH; Flow rate: 70 mL/min; Pressure: 100 bars; Temperature: 40° C. The individual stereoisomers are identified by their respective physical properties (e.g. NMR data and analytical SFC retention time) and their respective absolute configurations were assigned based on NIK inhibition potency and relative yield (not confirmed by X-ray crystallography).

Compound 4: 1-(3-(((1R,4R,5S)-4-hydroxy-2-methyl-3-oxo-2-azabicyclo[3.1.0]hexan-4-yl)ethynyl)phenyl)-7-methoxyimidazo[1,5-a]pyridine-3-carboxamide (20.5 mg, 20%). LC-MS (ES, m/z): 417 [M+H]⁺. ¹H NMR (400 MHz, DMSO-d₆) δ 9.38 (dd, J=7.8, 0.7 Hz, 1H), 8.06 (td, J=1.8, 0.6 Hz, 1H), 8.01-7.94 (m, 2H), 7.54-7.47 (m, 1H), 7.38-7.31 (m, 1H), 7.25 (dd, J=2.5, 0.8 Hz, 1H), 6.80 (dd, J=7.8, 2.5 Hz, 1H), 6.39 (s, 1H), 3.94 (s, 3H), 3.39-3.32 (m, 1H), 2.81 (s, 3H), 2.10-1.99 (m, 1H), 0.89-0.80 (m, 1H), 0.66-0.60 (m, 1H). SFC analytical conditions: Instrument: Waters ACQUITY UPC2 System (Waters UPC2); Column: Chiralpak ID (50×4.6 mm, 3 μm); Method: Isocratic (40% Mobile Phase B); Mobile Phase A: carbon dioxide; Mobile Phase B: Methanol with 0.1% NH₄OH; Flow rate: 4 mL/min; Pressure: 120 bars; Temperature: 40° C.; Retention time: 1.22 min (peak 3). This is the most potent NIK enzyme inhibitor among the 4 stereoisomers.

1-(3-(((1S,4S,5R)-4-hydroxy-2-methyl-3-oxo-2-azabicyclo[3.1.0]hexan-4-yl)ethynyl)phenyl)-7-methoxyimidazo[1,5-a]pyridine-3-carboxamide (16 mg, 16%). LC-MS (ES, m/z): 417 [M+H]⁺. 1H NMR (400 MHz, DMSO-d6) δ 9.38 (dd, J=7.8, 0.7 Hz, 1H), 8.06 (td, J=1.8, 0.6 Hz, 1H), 8.02-7.94 (m, 2H), 7.50 (td, J=7.7, 0.6 Hz, 1H), 7.25 (dd, J=2.5, 0.8 Hz, 1H), 7.28-7.22 (m, 1H), 6.80 (dd, J=7.8, 2.5 Hz, 1H), 6.39 (s, 1H), 3.94 (s, 3H), 3.39-3.32 (m, 1H), 2.81 (s, 3H), 2.10-1.98 (m, 1H), 0.89-0.80 (m, 1H), 0.68-0.59 (m, 1H). Retention time 1.33 min (peak 4). This stereoisomer showed no measurable inhibition for the NIK enzyme.

1-(3-(((1S,4R,5R)-4-hydroxy-2-methyl-3-oxo-2-azabicyclo[3.1.0]hexan-4-yl)ethynyl)phenyl)-7-methoxyimidazo[1,5-a]pyridine-3-carboxamide (15.4 mg, 15%). LC-MS (ES, m/z): 417 [M+H]⁺. ¹H NMR (400 MHz, DMSO-d6) δ 9.38 (dd, J=7.8, 0.7 Hz, 1H), 8.03 (td, J=1.8, 0.6 Hz, 1H), 7.99-7.94 (m, 2H), 7.52-7.46 (m, 2H), 7.35-7.30 (m, 1H), 7.24 (dd, J=2.6, 0.8 Hz, 1H), 6.82-6.76 (m, 2H), 3.94 (s, 3H), 3.30-3.27 (m, 1H), 2.84 (s, 3H), 1.93-1.83 (m, 1H), 1.09-1.01 (m, 1H), 0.55-0.48 (m, 1H). Retention time 0.96 min (peak 1). This is the second most potent NIK enzyme inhibitor among the 4 stereoisomers.

1-(3-(((1R,4S,5S)-4-hydroxy-2-methyl-3-oxo-2-azabicyclo[3.1.0]hexan-4-yl)ethynyl)phenyl)-7-methoxyimidazo[1,5-a]pyridine-3-carboxamide (10.3 mg, 10%). LC-MS (ES, m/z): 417 [M+H]⁺. ¹H NMR (400 MHz, DMSO-d₆) δ 9.38 (dd, J=7.8, 0.7 Hz, 1H), 8.03 (td, J=1.8, 0.6 Hz, 1H), 8.01-7.93 (m, 2H), 7.54-7.45 (m, 1H), 7.36-7.30 (m, 1H), 7.24 (dd, J=2.6, 0.8 Hz, 1H), 6.83-6.76 (m, 2H), 3.94 (s, 3H), 3.29-3.26 (m, 1H), 2.84 (s, 3H), 1.93-1.84 (m, 1H), 1.10-1.02 (m, 1H), 0.54-0.47 (m, 1H). Retention time 1.05 min (peak 2). This is the third most potent NIK enzyme inhibitor among the 4 stereoisomers.

Example 5

Synthesis of 3-(3-(((1R,4R,5S)-4-hydroxy-2-methyl-3-oxo-2-azabicyclo[3.1.0]hexan-4-yl)ethynyl)phenyl)imidazo[1,5-a]pyridine-1-carboxamide

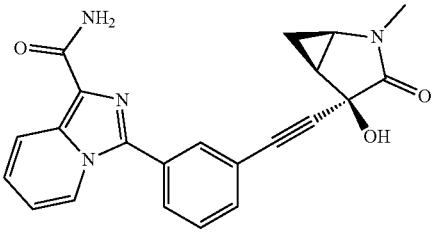 [SMILES: CN1C(=O)[C@](O)(C#Cc2cccc(-c3nc(C(N)=O)c4ccccn34)c2)[C@H]2C[C@H]21]

Ethyl 3-(3-((4-hydroxy-2-methyl-3-oxo-2-azabicyclo[3.1.0]hexan-4-yl)ethynyl)phenyl)imidazo[1,5-a]pyridine-1-carboxylate was prepared in two steps following the same reaction sequence as Example 3, Step 1 and 2 using ethyl 3-bromoimidazo[1,5-a]pyridine-1-carboxylate as a starting material in Step 1.

Step 3: Synthesis of 1-(3-((4-hydroxy-2-methyl-3-oxo-2-azabicyclo[3.1.0]hexan-4-yl)ethynyl)phenyl)imidazo[1,5-a]pyridine-3-carboxylic acid

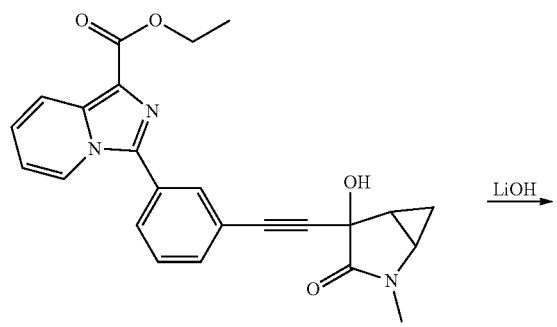

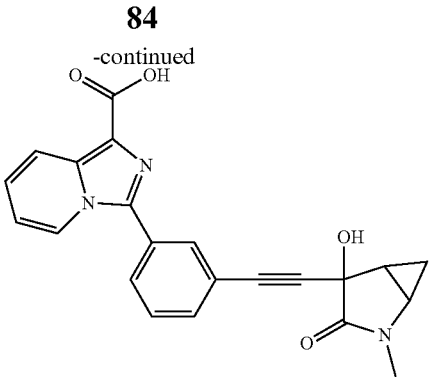

A mixture of ethyl 1-[3-[2-(2-hydroxy-4-methyl-3-oxo-4-azabicyclo[3.1.0]hexan-2-yl)ethynyl]phenyl]imidazo[1,5-a]pyridine-3-carboxylate (147 mg, 0.354 mmol) and 1 M aqueous LiOH (0.88 mL, 0.88 mmol) in methanol (4 ml) was stirred for 18 hours. The resulting mixture was acidified to pH 4 and partitioned between ethyl acetate and brine. The organic extracts were dried over MgSO₄ and concentrated giving a crude residue of the title compound (170 mg, 100%) which was used without further purification. LC-MS (ES, m/z): 386 [M−H]⁻, 388 [M+H]⁺.

Step 4: Synthesis of 1-(3-((4-hydroxy-2-methyl-3-oxo-2-azabicyclo[3.1.0]hexan-4-yl)ethynyl)phenyl)imidazo[1,5-a]pyridine-3-carboxamide

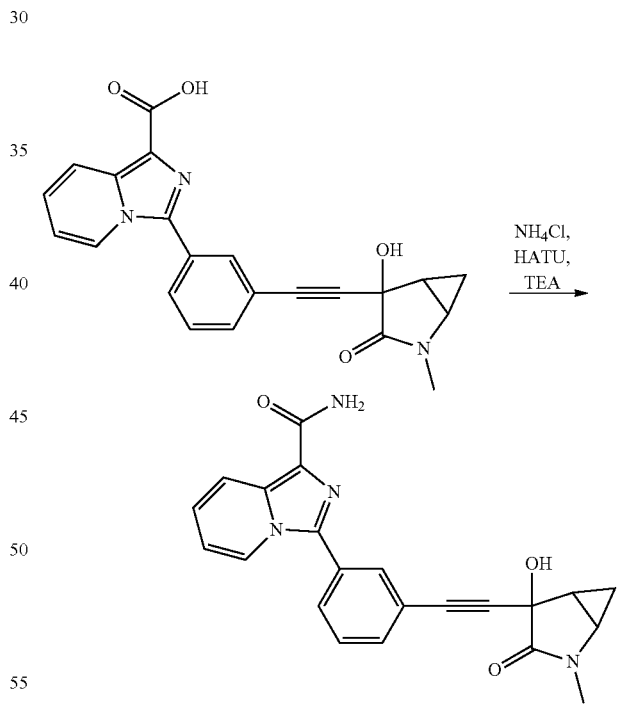

HATU (200 mg, 0.526 mmol) was added to a stirred mixture of 3-[3-[2-(2-hydroxy-4-methyl-3-oxo-4-azabicyclo[3.1.0]hexan-2-yl)ethynyl]phenyl]imidazo[1,5-a]pyridine-1-carboxylic acid (170 mg, 0.44 mmol), triethylamine (0.327 mL, 2.35 mmol) and finely powdered ammonium chloride (101 mg, 1.9 mmol) in N,N-dimethylformamide (4 mL). The mixture was stirred for 4 hours. The mixture was diluted with water and extracted with ethyl acetate. The organic extracts were washed with 5% aqueous citric acid, sat. NaHCO₃, water, brine, dried over MgSO₄ and concentrated. The residue was purified on a 4 g silica gel column eluting with methanol gradient in dichloromethane. Collected fractions give 95 mg (57%) of the title compound as a mixture of stereoisomers.

The above mixture was subjected to a chiral SFC separation to afford three of the four stereoisomers:

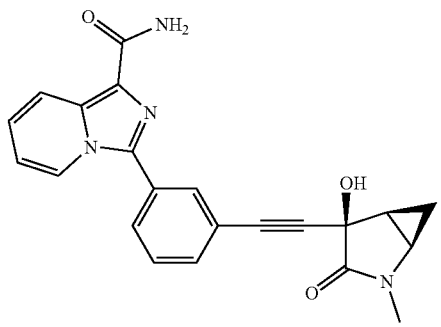

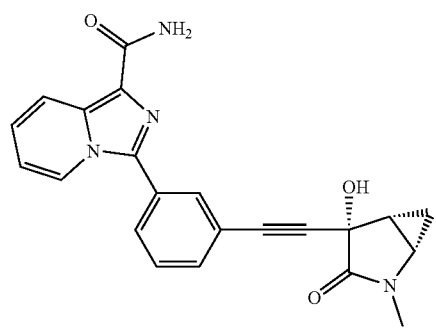

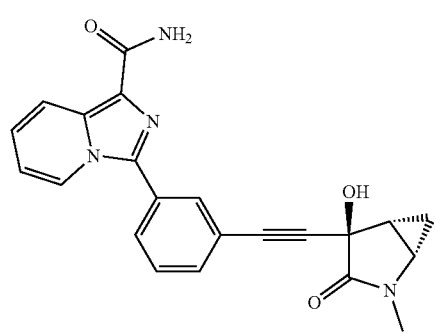

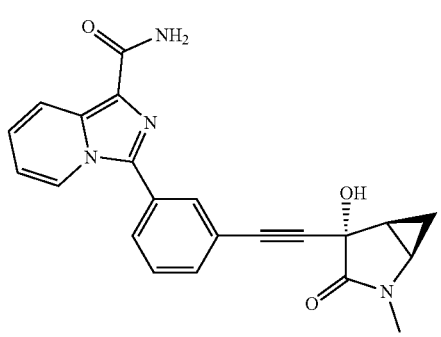

SFC preparative conditions: Instrument: SFC PICLab PREP 100 (PIC 100 SFC); Column: Chiralpak IA (250×21.1 mm, 5 μm); Method: Isocratic (40% Mobile Phase B); Mobile Phase A: carbon dioxide; Mobile Phase B: Methanol with 0.1% NH$_4$OH; Flow rate: 70 mL/min; Pressure: 100 bars; Temperature: 40° C. The individual stereoisomers are identified by their respective physical properties (e.g. NMR data and analytical SFC retention time) and their respective absolute configurations were assigned based on NIK inhibition potency and relative yield (not confirmed by X-ray crystallography).

Compound 5: 1-(3-(((1R,4R,5S)-4-hydroxy-2-methyl-3-oxo-2-azabicyclo[3.1.0]hexan-4-yl)ethynyl)phenyl)imidazo[1,5-a]pyridine-3-carboxamide) (12 mg, 12.4%). LC-MS (ES, m/z): 387 [M+H]$^+$. $^1$H NMR (400 MHz, DMSO-d$_6$) δ 8.55 (dt, J=7.2, 1.1 Hz, 1H), 8.21 (dt, J=9.1, 1.3 Hz, 1H), 7.96-7.90 (m, 2H), 7.66-7.55 (m, 2H), 7.22-7.13 (m, 2H), 6.97-6.89 (m, 1H), 6.43 (s, 1H), 3.34-3.32 (m, 1H), 2.81 (s, 3H), 2.08-2.00 (m, 1H), 0.89-0.80 (m, 1H), 0.67-0.59 (m, 1H). Supercritical Fluid Chromatography analytical conditions: Instrument: Waters ACQUITY UPC2 System (Waters UPC2); Column: Chiralpak IA (50×4.6 mm, 3 μm); Method: Isocratic (35% Mobile Phase B); Mobile Phase A: carbon dioxide; Mobile Phase B: Methanol with 0.1% NH$_4$OH; Flow rate: 4 mL/min; Pressure: 120 bars; Temperature: 40° C.; Retention time: 1.17 min (peak 2). This is the most potent NIK enzyme inhibitor among the 4 stereoisomers.

3-(3-(((1 S,4R,5R)-4-hydroxy-2-methyl-3-oxo-2-azabicyclo[3.1.0]hexan-4-yl)ethynyl)phenyl)imidazo[1,5-a]pyridine-1-carboxamide (11.6 mg, 12%). LC-MS (ES, m/z): 387 [M+H]$^+$. $^1$H NMR (400 MHz, DMSO-d$_6$) δ 8.54 (dd, J=7.3, 1.1 Hz, 1H), 8.21 (dt, J=9.2, 1.2 Hz, 1H), 7.96-7.89 (m, 2H), 7.65-7.54 (m, 2H), 7.22-7.12 (m, 2H), 6.97-6.90 (m, 1H), 6.43 (s, 1H), 3.31-3.30 (m, 1H), 2.81 (s, 3H), 2.09-2.00 (m, 1H), 0.89-0.80 (m, 1H), 0.66-0.61 (m, 1H). Retention time 1.38 min (peak 3). This is the second most potent NIK enzyme inhibitor among the 4 stereoisomers.

3-(3-(((1S,4S,5R)-4-hydroxy-2-methyl-3-oxo-2-azabicyclo[3.1.0]hexan-4-yl)ethynyl)phenyl)imidazo[1,5-a]pyridine-1-carboxamide (4 mg, 4%). LC-MS (ES, m/z): 387 [M+H]$^+$. $^1$H NMR (400 MHz, DMSO-d$_6$) δ 8.55 (dt, J=7.2, 1.1 Hz, 1H), 8.21 (dt, J=9.1, 1.3 Hz, 1H), 7.96-7.90 (m, 2H), 7.65-7.54 (m, 3H), 7.22-7.12 (m, 2H), 6.97-6.90 (m, 1H), 6.43 (s, 1H), 3.31-3.29 (m, 1H), 2.81 (s, 3H), 2.08-2.00 (m, 1H), 0.89-0.81 (m, 1H), 0.67-0.59 (m, 1H). Retention time 0.98 min (peak 1). This is the third most potent NIK enzyme inhibitor among the 4 stereoisomers.

Example 6

Synthesis of 5-amino-2-(3-(((1R,4R,5S)-4-hydroxy-2-methyl-3-oxo-2-azabicyclo[3.1.0]hexan-4-yl)ethynyl)phenyl)thiazole-4-carboxamide

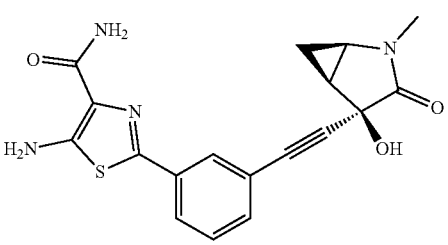 [SMILES: CN1C(=O)[C@](O)(C#Cc2cccc(-c3nc(C(N)=O)c(N)s3)c2)[C@H]2C[C@H]21]

Step 1: Synthesis of methyl-2-bromo-5-((tert-butoxycarbonyl)amino)thiazole-4-carboxylate

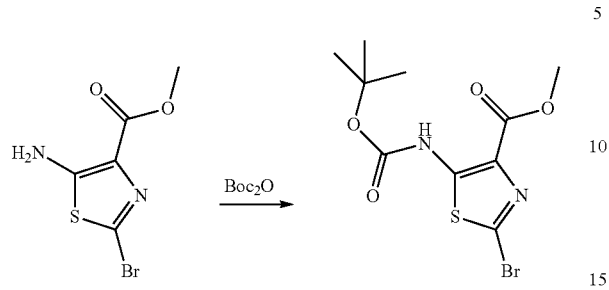

A solution of tert-butoxycarbonyl tert-butyl carbonate (476 mg, 2.18 mmol) was added dropwise to a suspension of methyl 2-bromo-5-(tert-butoxycarbonylamino)thiazole-4-carboxylate (633 mg, 1.88 mmol), N,N-diisopropylethylamine (0.38 mL, 2.2 mmol) and 4-dimethylaminopyridine (25 mg, 0.20463 mmol) in dichloromethane (20 ml). The mixture was stirred for 3 hours, concentrated and the residue was partitioned between ethyl acetate and water. The organic extracts were washed with 5% aqueous citric acid, water, brine, dried over MgSO$_4$ and concentrated. The residue was purified on 12 g silica gel column eluting with iPrOAc gradient in heptane to afford the title compound (633 mg, 94.7%). LC-MS (ES, m/z): 337 [M+H]$^+$.

Step 2: Synthesis of methyl 5-((tert-butoxycarbonyl)amino)-2-(3-(trimethylsilyl)phenyl)thiazole-4-carboxylate

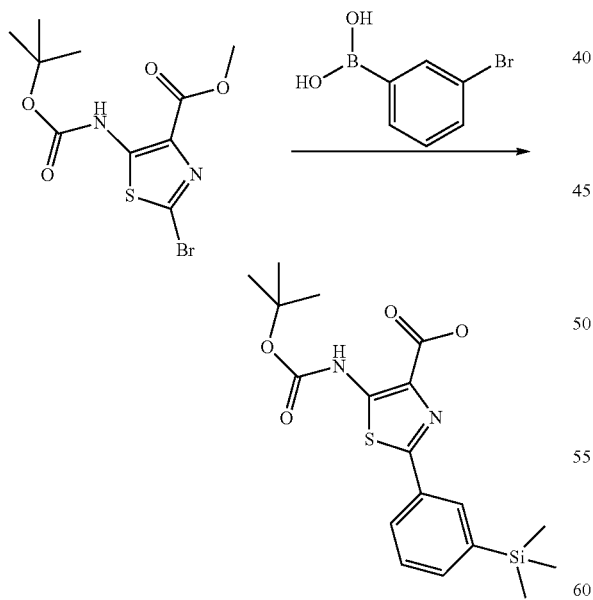

The title compound was prepared following procedure as Example 3, Step 1 and using methyl 2-bromo-5-((tert-butoxycarbonyl)amino)thiazole-4-carboxylate as a starting material to afford 185 mg (73.7%). LC-MS (ES, m/z): 407 [M+H]$^+$.

Step 3: Synthesis of methyl 5-((tert-butoxycarbonyl)amino)-2-(3-iodophenyl)thiazole-4-carboxylate

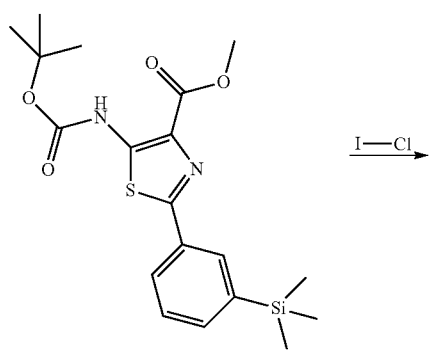

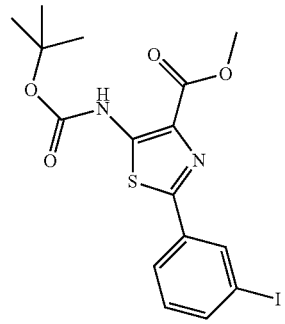

The title compound was prepared following procedure as Example 3, Step 2, and using methyl 5-((tert-butoxycarbonyl)amino)-2-(3-(trimethylsilyl)phenyl)thiazole-4-carboxylate as a starting material to afford 140 mg (66.8%). LC-MS (ES, m/z): 461 [M+H]$^+$.

Step 4: Synthesis of methyl 5-((tert-butoxycarbonyl)amino)-2-(3-((4-hydroxy-2-methyl-3-oxo-2-azabicyclo[3.1.0]hexan-4-yl)ethynyl)phenyl)thiazole-4-carboxylate

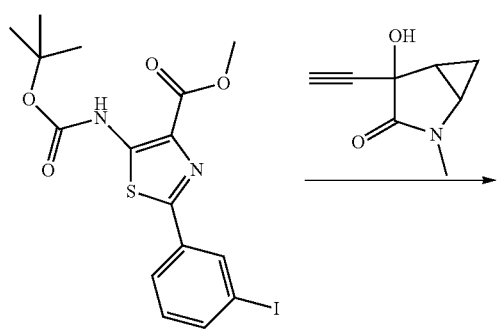

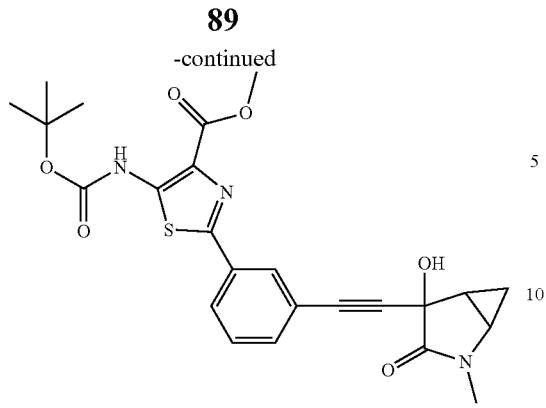

The title compound was obtained by procedures similar to those described for Examples 1 and 2, Step 1 to afford 112 mg (76.2%) as a mixture of stereoisomers. LC-MS (ES, m/z): 484 [M+H]+.

Step 5: Synthesis of tert-butyl (4-carbamoyl-2-(3-((4-hydroxy-2-methyl-3-oxo-2-azabicyclo[3.1.0]hexan-4-yl)ethynyl)phenyl)thiazol-5-yl)carbamate

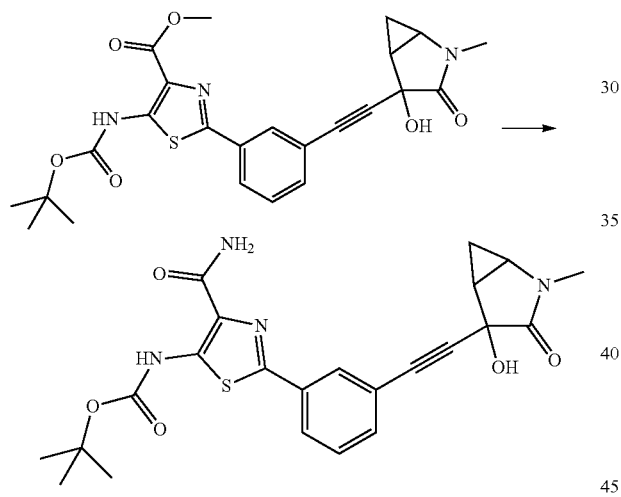

The title compound was obtained by a procedure similar to that described for Examples 1 and 2, Step 2 to afford 102 mg (94%) as a mixture of stereoisomers. LC-MS (ES, m/z): 469 [M+H]+.

Step 6: 5-amino-2-(3-((4-hydroxy-2-methyl-3-oxo-2-azabicyclo[3.1.0]hexan-4-yl) ethynyl)phenyl) thiazole-4-carboxamide

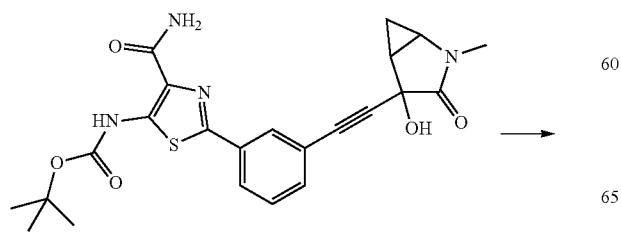

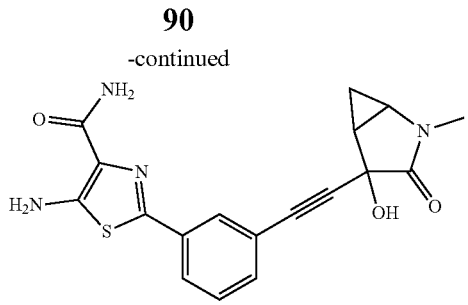

The title compound was obtained by a deprotection procedure as follows: A solution of hydrogen chloride in dioxane (4 mL, 16 mmol, 4.0 mol/L) was added to a solution of tert-butyl-N-[4-carbamoyl-2-[3-[2-(2-hydroxy-4-methyl-3-oxo-4-azabicyclo[3.1.0]hexan-2-yl)ethynyl]phenyl]thiazol-5-yl]carbamate (102 mg, 0.22 mmol) in 6 ml of dichloromethane. The mixture was stirred for 1 hour, concentrated and partitioned between saturated aqueous NaHCO₃ and ethyl acetate. The organic extracts were washed with brine, dried over MgSO₄ and concentrated to give 51 mg (63%) of the title compound as a mixture of diastereomers. LC-MS (ES, m/z): 369 [M+H]+.

The above mixture was subjected to a chiral SFC separation to afford four stereoisomers:

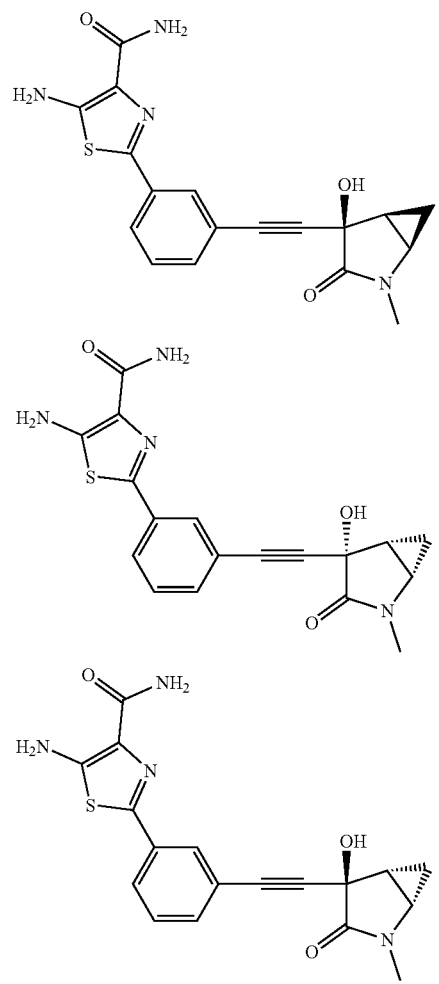

-continued

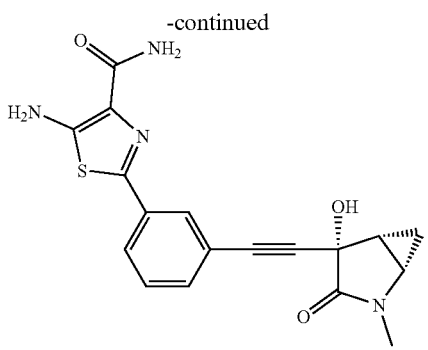

SFC preparative conditions: Instrument: SFC PICLab PREP 100 (PIC 100 SFC); Column: Chiralpak IA (250×21.1 mm, 5 μm); Method: Isocratic (40% Mobile Phase B); Mobile Phase A: carbon dioxide; Mobile Phase B: Methanol with 0.1% $NH_4OH$; Flow rate: 70 mL/min; Pressure: 100 bars; Temperature: 40° C. The individual stereoisomers are identified by their respective physical properties (e.g. NMR data and analytical SFC retention time) and their respective absolute configurations were assigned based on NIK inhibition potency and relative yield (not confirmed by X-ray crystallography).

Compound 6: 1-(3-(((1R,4R,5S)-4-hydroxy-2-methyl-3-oxo-2-azabicyclo[3.1.0]hexan-4-yl)ethynyl)phenyl)imidazo[1,5-a]pyridine-3-carboxamide) (8.2 mg, 16%). LC-MS (ES, m/z): 369 $[M+H]^+$. $^1H$ NMR (400 MHz, DMSO-d6) δ 7.87 (td, J=1.7, 0.6 Hz, 1H), 7.78-7.73 (m, 1H), 7.48-7.37 (m, 5H), 7.07 (s, 1H), 6.40 (s, 1H), 3.31-3.29 (m, 1H), 2.81 (s, 3H), 2.06-1.99 (m, 1H), 0.89-0.81 (m, 1H), 0.66-0.59 (m, 1H). Supercritical Fluid Chromatography analytical conditions: Instrument: Waters ACQUITY UPC2 System (Waters UPC2); Column: Chiralpak IA (50×4.6 mm, 3 μm); Method: Isocratic (35% Mobile Phase B); Mobile Phase A: carbon dioxide; Mobile Phase B: Methanol with 0.1% $NH_4OH$; Flow rate: 4 mL/min; Pressure: 120 bars; Temperature: 40° C.; Retention time 1.01 min (peak 2). This is the most potent NIK enzyme inhibitor among the 4 stereoisomers.

5-amino-2-(3-((4-hydroxy-2-methyl-3-oxo-2-azabicyclo[3.1.0]hexan-4-yl)ethynyl)phenyl)thiazole-4-carboxamide, Peak 4 (3.3 mg, 6.4%). LC-MS (ES, m/z): 369 $[M+H]^+$. $^1H$ NMR (400 MHz, DMSO-d$_6$) δ 7.87 (td, J=1.7, 0.6 Hz, 1H), 7.78-7.73 (m, 1H), 7.49-7.37 (m, 5H), 7.07 (s, 1H), 6.40 (s, 1H), 3.31-3.29 (m, 1H), 2.81 (s, 3H), 2.07-2.00 (m, 1H), 0.89-0.80 (m, 1H), 0.66-0.59 (m, 1H). Retention time 1.40 min (peak 4). This isomer is a less potent NIK enzyme inhibitor than Compound 6.

5-amino-2-(3-((4-hydroxy-2-methyl-3-oxo-2-azabicyclo[3.1.0]hexan-4-yl)ethynyl)phenyl)thiazole-4-carboxamide, Peak 1 (3.2 mg, 6.3%). LC-MS (ES, m/z): 369 $[M+H]^+$. $^1H$ NMR (400 MHz, DMSO-d$_6$) δ 7.85 (td, J=1.8, 0.6 Hz, 1H), 7.77-7.72 (m, 1H), 7.48-7.37 (m, 5H), 7.07 (s, 1H), 6.79 (s, 1H), 3.30-3.26 (m, 2H), 2.83 (s, 3H), 1.90-1.82 (m, 1H), 1.09-1.00 (m, 1H), 0.55-0.48 (m, 1H). Retention time 0.85 min (peak 1). This isomer is a less potent NIK enzyme inhibitor than Compound 6.

5-amino-2-(3-((4-hydroxy-2-methyl-3-oxo-2-azabicyclo[3.1.0]hexan-4-yl)ethynyl)phenyl)thiazole-4-carboxamide, Peak 3 (3.9 mg, 7.7%). LC-MS (ES, m/z): 369 $[M+H]^+$. $^1H$ NMR (400 MHz, DMSO-d$_6$) δ 7.85 (td, J=1.8, 0.6 Hz, 1H), 7.77-7.72 (m, 1H), 7.47-7.37 (m, 5H), 7.07 (s, 1H), 6.79 (s, 1H), 3.30-3.26 (m, 1H), 2.83 (s, 3H), 1.91-1.82 (m, 1H), 1.08-1.00 (m, 1H), 0.54-0.48 (m, 1H). Retention time 1.08 min (peak 3). This isomer is a less potent NIK enzyme inhibitor than Compound 6.

BIOLOGICAL EXAMPLES

Example B1—NIK Enzyme Inhibition Assay

The ability of the nuclear factor-kappa B (NF-kB)-inducing kinase (NIK) to catalyze the hydrolysis of adenosine-5'-triphosphate (ATP) was monitored using the Transcreener ADP (adenosine-5'-diphosphate) assay (BellBrook Labs). Purified NIK (0.5 nM) derived from a baculovirus-infected insect cell expression system was incubated with test compounds for 1-3.5 hours in 50 mM 2-[4-(2-hydroxyethyl)piperazin-1-yl]ethanesulfonic acid buffer (pH 7.2) containing 10 mM $MgCl_2$, 2 mM dithiothreitol, 10 μM ATP, 0.01% Triton X-100, 0.1% gamma-globulins from bovine blood, 1% dimethylsulfoxide (DMSO), 7 μg/mL ADP antibody and 5 nM ADP-MR121 633 tracer. Reactions were quenched by the addition of 20 mM 2,2',2'',2'''-(ethane-1,2-diyldinitrilo)tetraacetic acid and 0.01% Brij 35. The tracer bound to the antibody was displaced by the ADP generated during the NIK reaction, which causes a decrease in fluorescence polarization that was measured by laser excitation at 633 nm with a Fluorescence Correlation Spectroscopy Plus reader (Evotec AG). Equilibrium dissociation constant ($K_i$) values for NIK inhibitors are calculated from plots of activity vs. inhibitor concentration using Morrison's quadratic equation that accounts for the potential of tight binding, and by also applying the conversion factor that accounted for competitive inhibition and the concentration of substrate used in the assay relative to its Michaelis constant ($K_m$). The inhibitory values (NIK ADP-FP, $K_i$) obtained are listed in Table B1.

TABLE B1

| Compound No. | NIK ADP-FP $K_i$ (nM) |
|---|---|
| 1 | 0.88 |
| 2 | 4.3 |
| 3 | 0.050 |
| 4 | 0.050 |
| 5 | 4.7 |
| 6 | 0.050 |
| C-1 | 0.17 |
| C-3 | 0.095 |
| C-4 | 0.050 |
| C-5 | 4.7 |
| C-6 | 0.13 |

Example B2—Cellular Assay

Several assays were developed to profile the cellular activities of NIK inhibitors.

(1) The first assay that can be used to profile whether a test compound can inhibit the NF-kB signal through NIK inhibition without affecting cell viability. In this assay, human embryonic kidney 293 cells are stably transfected with a tetracycline-inducible NIK DNA construct containing a cytomegalovirus promoter plus two reporter DNA constructs. One reporter encodes firefly luciferase under the control of three repeats of an NF-kB response element from the ELAM-1 gene and reflects the level of NIK activity in the cells, whereas the other reporter constitutively expresses Renilla luciferase under the control of the herpes simplex virus thymidine kinase promoter and serves as a general measure of cell viability. Cells are incubated with different concentrations of compounds (0.2% DMSO final) in medium containing 1 µg/mL doxycycline and 10% tet-system approved fetal bovine serum (Clontech) for 24 hours, after which the reporters' signals are detected using the Dual Glo luciferase detection system (Promega) according to the vendor's protocol.

(2) A second set of cell assays used primary human umbilical vein cells (HUVEC) sourced from Lonza to define the selectivity of NIK inhibitors toward inhibition of classical vs. non-classical NF-kB signaling using high content cellular imaging. For the p52 (non-classical NF-kB signaling) nuclear translocation assay, HUVEC were treated with different concentrations of compounds (0.2% DMSO final) in EBM-2 medium (LONZA) containing 2% fetal bovine serum and then stimulated with 300 ng/mL of an anti-lymphotoxin beta receptor antibody (R&D Systems) for 4.5 hours. In the REL-A nuclear translocation assay, HUVEC were incubated with compounds (0.2% DMSO final) for 4 hours 50 minutes in EBM-2 medium containing 2% fetal bovine serum before stimulating them with 2 ng/mL tumor necrosis factor (TNF)-α (R&D Systems) for 10 minutes. Cells were fixed with 4% paraformaldehyde, permeabilized by adding 0.1% Triton X-100 in phosphate buffered saline, and then were incubated with either 2 µg/mL anti-p52 antibody (Millipore) or 400 ng/mL anti-REL-A (p65) antibody (Santa Cruz Biotechnology). Finally, the cells were incubated with an Alexa488-labeled secondary antibody (Invitrogen) and DRAQ5 DNA stain (Biostatus). Imaging was carried out using an Opera reader (Perkin Elmer) and data were analyzed with the aid of Acapella software (Perkin Elmer). The p52 or REL-A translocation into the nucleus was quantified by the ratio of the nuclear to cytoplasmic signal intensity. The concentration of inhibitor required for 50% inhibition (IC50 values) in these cell assays were derived from the plots of signal vs. inhibitor concentration.

(3) A third set of cell assays are used to define the selectivity of NIK inhibitors toward inhibition of classical vs. non-classical NF-kB signaling and rely on quantification of the nuclear translocation of p52 (NF-kB2) and REL-A (p65) using high content cellular imaging. For the p52 (non-classical NF-kB signaling) nuclear translocation assay, HeLa cells are treated with different concentrations of compounds (0.2% DMSO final) in medium containing 10% fetal bovine serum and then stimulated with 100 ng/mL of an anti-lymphotoxin beta receptor antibody (R&D Systems) for 5 hours. In the REL-A nuclear translocation assay, HeLa cells are incubated with compounds (0.2% DMSO final) for 4.5 hours in medium containing 10% fetal bovine serum before stimulating them with 10 ng/mL tumor necrosis factor (TNF)-α (R&D Systems) for 30 minutes. Cells are fixed with 4% paraformaldehyde, permeabilized by adding 0.1% Triton X-100 in phosphate buffered saline, and then are incubated with either 2 µg/mL anti-p52 antibody (Millipore) or 400 ng/mL anti-REL-A (p65) antibody (Santa Cruz Biotechnology). Finally, the cells are incubated with an Alexa488-labeled secondary antibody (Invitrogen) and DRAQ5 DNA stain (Biostatus). Imaging is carried out using an Opera reader (Perkin Elmer) and data are analyzed with the aid of Acapella software (Perkin Elmer). The p52 or REL-A translocation into the nucleus is quantified by the ratio of the nuclear to cytoplasmic signal intensity. The concentration of inhibitor required for 50% inhibition (IC$_{50}$ values) in these cell assays are derived from the plots of signal vs. inhibitor concentration. The test compounds have the corresponding inhibitory values (IC$_{50}$) for NIK REL-A (p65) and p52 Translocation Assays as set forth in Table B2.

TABLE B2

| Compound No. | REL-A HUVEC Translocation Assay (IC$_{50}$) [µM] | REL-A HeLa Translocation Assay (IC$_{50}$) [µM] | p52 HUVEC Translocation Assay (IC$_{50}$) [µM] | p52 HeLa Translocation Assay (IC$_{50}$) [µM] |
|---|---|---|---|---|
| 1 | >5 | | 0.055 | |
| 2 | >5 | | 0.28 | |
| 3 | >5 | | 0.025 | |
| 5 | >5 | | 3 | |
| C-1 | | >20 | | 0.0795 |
| C-3 | >5 | >20 | | 0.0298 |
| C-4 | >5 | >1.0 | | 0.0066 |
| C-5 | | >20 | | 0.2399 |
| C-6 | | >5.0 | | 0.0791 |

Example B3—Liver Microsome Stability

General.

Metabolic stability assays in liver microsomes are conducted with pooled female CD-1 mouse, male Sprague-Dawley rat, male beagle dog, male cynomolgus monkey, and mixed male and female human liver microsomal incubations. The general assay conditions are as follows. Incubation mixtures consisted of liver microsomes (0.5 mg of microsomal protein/ml) and the test compound (1.0 µM) with or without NADPH (1.0 mM) in the potassium phosphate buffer (100 mM; pH 7.4) with a final incubation volume of 0.25 ml. Reactions are initiated by the addition of NADPH or buffer and shaken in a water bath open to the air at 37° C. At times 0, 20, 40, and 60 min, aliquots (50 µl) are removed and added to termination mixtures (100 µl) containing acetonitrile and an internal standard. The samples are then centrifuged for 10 min at 2000 g. The supernatant (90 µl) is removed, combined with 180 µl of water, and analyzed by LC-MS/MS.

Metabolic stability of the test compounds were evaluated in human liver microsomes following known protocols described in Halladay, et al. *Drug Metabol. Lett.* 2007, 1:67-72.

The human liver microsome clearance (HLM CL, in mL/min/kg) obtained for the test compounds are shown in Table B3. A lower clearance value indicates better metabolic stability. Compound Nos. 1, 3, 4, 5 and 6 in each case showed better stability in human liver microsomes than the respective comparator compounds C-1, C-3, C-4, C-5 and C-6. Also see FIG. 1.

TABLE B3

| Compound No. | HLM CL (mL/min/kg) |
|---|---|
| 1 | 5.8 |
| 2 | 7.7 |
| 3 | 11 |
| 4 | 12 |
| 5 | 3.5 |
| 6 | 1.6 |
| C-1 | 7.4 |
| C-3 | 13 |
| C-4 | 15 |
| C-5 | 4.0 |
| C-6 | 5.1 |

Example B4—Hepatocyte Stability

General. Metabolic stability assays in hepatocytes are conducted using cryopreserved pooled female CD-1 mouse, male Sprague-Dawley rat, male beagle dog, male cynomolgus monkey, and mixed male and female human hepatocytes (CellzDirect). Vials of hepatocytes are thawed rapidly in a water bath set at 37° C. and then are diluted with Dulbecco's modified Eagle's medium (DMEM), pH 7.4. Cells are isolated by centrifugation, pooled, and resuspended in DMEM at 1.0 million viable cells/ml. Membrane integrity of the cells is assessed by trypan blue exclusion. The test compound is dissolved in dimethyl sulfoxide at a final concentration of 10 mM. This test compound stock is diluted further to 2 µM in DMEM (125 µl) before the addition of an equal volume of the $10^6$ cells/ml cell suspension. The test compound (final incubation concentration of 1.0 µM with 0.1% dimethyl sulfoxide) and cells (final concentration of $0.5 \times 10^6$ cells/ml) are incubated at 37° C. in a 95% air/5% $CO_2$ atmosphere for 3 h. Aliquots (50 µl) are removed at 0, 1, 2, and 3 hours and added to termination mixtures (100 µl) containing acetonitrile and an internal standard. The samples are then centrifuged for 10 min at 2000 g. The supernatant (90 µl) is removed, combined with 180 µl of water, and analyzed by LC-MS/MS.

Metabolic stability of the test compounds were evaluated also in human hepatocytes, following protocols described in Hallifax, et al. *Drug Metabol. Disposition*, 2005, 33:1852-1858.

Figure 2:
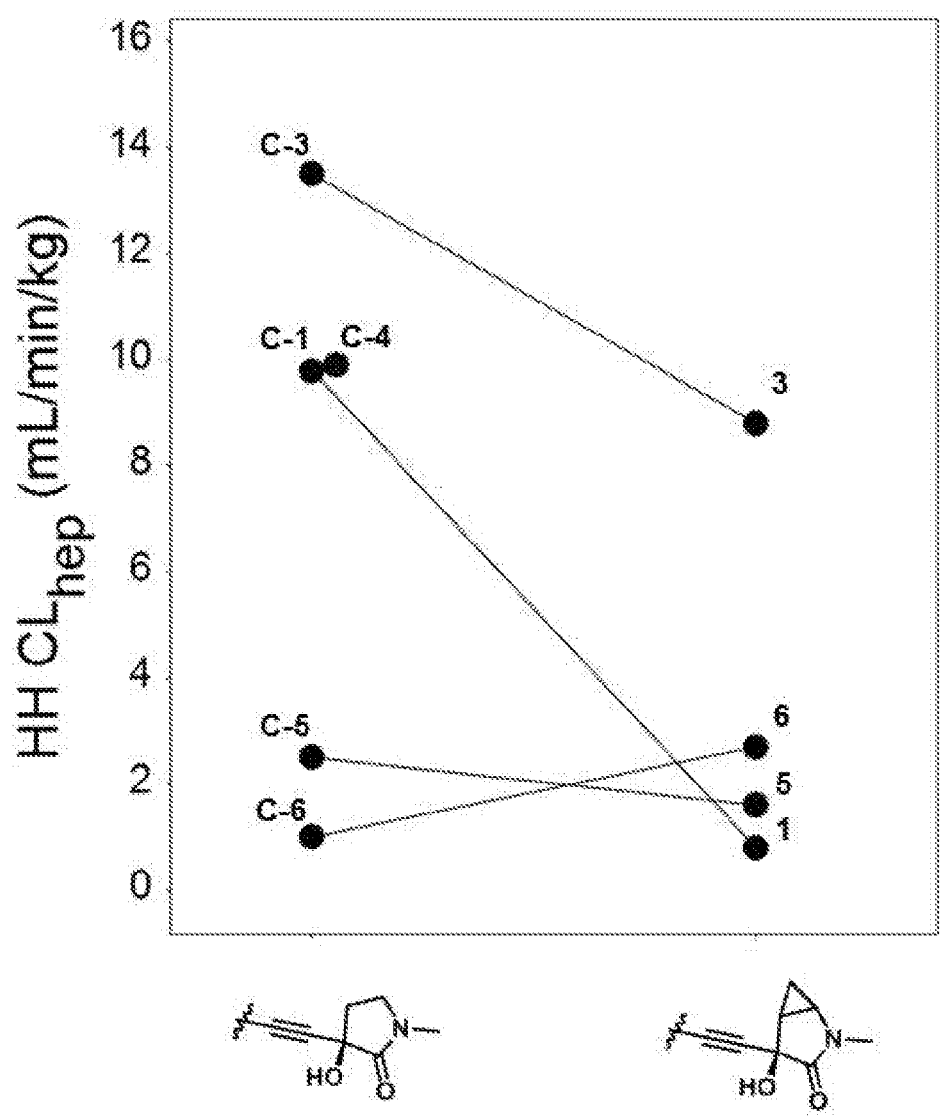
FIG. 2 shows human hepatocyte clearance (in mL/min/kg) measured for the exemplary 2-azabicyclo[3.1.0]hexan-3-one compounds in comparison with that of the corresponding pyrrolidinone compounds.

The human hepatocyte clearance (Hep CL, in mL/min/kg) obtained for the test compounds are shown in Table B4. A lower clearance value indicates better metabolic stability. Compound Nos. 1, 3 and 5 show better stability than the corresponding comparator compounds C-1, C-3 and C-5 respectively in the human hepatocyte assay. A greater improvement is shown for 2-azabicyclo[3.1.0]hexan-3-one compounds in cases where the corresponding pyrrolidinone compounds have a relatively high clearance. Also see FIG. 2.

TABLE B4

| Compound No. | Hep CL (mL/min/kg) |
|---|---|
| 1 | 0.8 |
| 2 | 13 |
| 3 | 9.0 |
| 4 | N.D. |
| 5 | 1.6 |
| 6 | 2.7 |
| C-1 | 9.5 |
| C-3 | 14 |
| C-4 | 9.9 |
| C-5 | 2.5 |
| C-6 | 1.1 |

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A compound of formula (A):

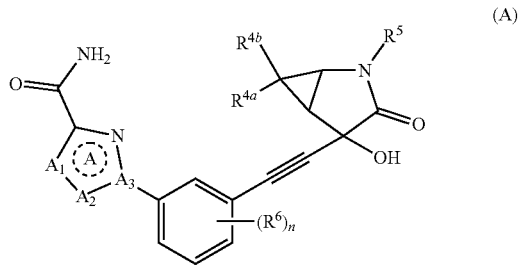

or a stereoisomer, tautomer, solvate, or pharmaceutically acceptable salt thereof, wherein:
ring A is a monocycle or a fused bicycle;
$A_1$ is $NR^1$, N, S, $CR^1$ or $CHR^1$;
$A_2$ is $NR^2$, N, O, S, $CR^2$ or $CHR^2$;
$A_3$ is N or C;
provided that no more than two of (i)-(iii) apply: (i) $A_1$ is $NR^1$ or N, (ii) $A_2$ is $NR^2$ or N, and (iii) $A_3$ is N;
each $R^1$ is independently selected from the group consisting of H, halogen, —$NR^aR^b$, —$NHC(O)NR^aR^b$, —$NHS(O)_2$—$C_1$-$C_3$ alkyl, $C_1$-$C_3$ alkyl, $C_3$-$C_7$ cycloalkyl, $C_1$-$C_3$ alkoxy and 3-11 membered heterocyclyl, wherein the $C_1$-$C_3$ alkyl of $R^1$ is optionally substituted by F, OH, CN, SH, $C_1$-$C_3$ alkoxy or 3-11 membered heterocyclyl; the $C_3$-$C_7$ cycloalkyl of $R^1$ is optionally substituted by F, OH, CN, SH, $CH_3$ or $CF_3$; the $C_1$-$C_3$ alkoxy of $R^1$ is optionally substituted by F, OH, CN or SH; and the 3-11 membered heterocyclyl of $R^1$ is optionally substituted by F, OH, CN, SH, $CF_3$ or $C_1$-$C_3$ alkyl;
each $R^2$ is independently selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl, wherein the $C_1$-$C_6$ alkyl, $C_3$-$C_7$ cycloalkyl, $C_1$-$C_6$ alkoxy, phenyl and 3-11 membered heterocyclyl of $R^2$ is optionally substituted by $R^c$; or
$R^1$ and $R^2$ are taken together with the atoms to which they are attached to form a cyclic group selected from the group consisting of $C_3$-$C_7$ cycloalkyl, phenyl and 3-11 membered heterocyclyl, wherein the cyclic group is optionally substituted by $R^d$;
each $R^{4a}$ and $R^{4b}$ is independently H or F;
$R^5$ is $C_1$-$C_6$ alkyl or $C_3$-$C_4$ cycloalkyl, wherein the $C_1$-$C_6$ alkyl and $C_3$-$C_4$ cycloalkyl of $R^5$ are independently optionally substituted by halogen, OH, or $C_1$-$C_6$ alkoxy;
each $R^6$ is independently selected from the group consisting of F, Cl, $OCH_3$, $CH_3$ and $CF_3$;
n is 0, 1 or 2,
$R^a$ is selected from the group consisting of H and $C_1$-$C_6$ alkyl optionally substituted by $C_1$-$C_3$ alkoxy, F, OH, CN, SH, $CH_3$ or $CF_3$;
$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl wherein $R^b$ may be optionally substituted by $C_1$-$C_3$ alkoxy, F, OH, CN, SH, $CH_3$ or $CF_3$;
$R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—$NH_2$, —$(X^1)_{0-1}$—N(H)($R^{1a}$), —$(X^1)_{0-1}$—N($R^{1b}$)($R^{1a}$), $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, —$(X^1)_{0-1}$—$C_1$-$C_6$ alkyl, —$(X^1)_{0-1}$—$C_3$-$C_{10}$ cycloalkyl, cycloalkyl, —$(X^1)_{0-1}$-3-11 membered heterocyclyl, —$(X^1)_{0-1}$-$C_6$-$C_{10}$ aryl, —C(=O)$(X^1)_{0-1}$-$C_3$-$C_{10}$ cycloalkyl, —C(=O)$(X^1)_{0-1}$-3-11 membered heterocyclyl, —$(X^1)_{0-1}$—C(=$Y^1$)N(H)($R^{1a}$), —$(X^1)_{0-1}$—C(=$Y^1$)NH$_2$, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}$NH$_2$, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$-C(=NOH)$R^{1a}$, —$(X^1)_{0-1}$—C(=NO$R^{1b}$)$R^{1a}$, —$(X^1)_{0-1}$—NHC(=$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1b}$), —$(X^1)_{0-1}$—N($R^{1a}$)C(=$Y^1$)NH$_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$); wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl, (3-11 membered heterocyclylene)$C_1$-$C_6$ alkyl, phenyl, and ($C_6$-$C_{10}$ arylene)$C_1$-$C_6$ alkyl, or $R^{1a}$ and $R^{1b}$, when attached to the same nitrogen atom, are taken together with the nitrogen to which they are attached to form a 3-11 membered heterocyclyl comprising 0-3 additional heteroatoms selected from N, O and S; $Y^1$ is O, N$R^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is independently further substituted by from 0 to 4 $R^f$ substituents selected from the group consisting of halogen, CN, NO$_2$, SF$_5$, OH, NH$_2$, —N($C_1$-$C_6$ alkyl)$_2$, —NH($C_1$-$C_6$ alkyl), oxo, $C_1$-$C_6$ alkyl, —($C_2$-$C_6$ alkynylene)-(3-11 membered heterocyclyl, wherein the heterocyclyl is optionally substituted by $R^e$), $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl, —C(=O)N(H)($C_1$-$C_6$ alkyl), —C(=O)N($C_1$-$C_6$ alkyl)$_2$, —C(=O)NH$_2$, —C(=O)O$C_1$-$C_6$ alkyl, —C(=O)OH, —N(H)C(=O)($C_1$-$C_6$ alkyl), —N($C_1$-$C_6$ alkyl)C(=O)($C_1$-$C_6$ alkyl), —N(H)C(=O)O$C_1$-$C_6$ alkyl, —N($C_1$-$C_6$ alkyl)C(=O)O$C_1$-$C_6$ (halo)alkyl, —S(O)$_{1-2}C_1$-$C_6$ alkyl, —N(H)S(O)$_{1-2}C_1$-$C_6$ alkyl, —N($C_1$-$C_6$ alkyl)S(O)$_{1-2}C_1$-$C_6$ alkyl, —S(O)$_{0-1}$N(H)($C_1$-$C_6$ alkyl), —S(O)$_{0-1}$N($C_1$-$C_6$ alkyl)$_2$, —S(O)$_{0-1}$NH$_2$, —C(=O)$C_1$-$C_6$ alkyl, —C(=O)$C_3$-$C_7$ cycloalkyl, —C(=NOH)$C_1$-$C_6$ alkyl, —C(=NO$C_1$-$C_6$ alkyl)$C_1$-$C_6$ alkyl, —NHC(=O)N(H)($C_1$-$C_6$ alkyl), —NHC(=O)N($C_1$-$C_6$ alkyl)$_2$, —NHC(=O)NH$_2$, —N($C_1$-$C_6$ alkyl)C(=O)N(H)($C_1$-$C_6$ alkyl), —N($C_1$-$C_6$ alkyl)C(=O)NH$_2$, —OC(=O)$C_1$-$C_6$ alkyl, —OC(=O)O$C_1$-$C_6$ alkyl, —OP(=O)(O$C_1$-$C_6$ alkyl)$_2$, —SC(=O)O$C_1$-$C_6$ alkyl and —SC(=O)N($C_1$-$C_6$ alkyl)$_2$, wherein any alkyl portion of $R^f$ is optionally substituted with halogen;

$R^e$ is selected from the group consisting of halogen, OH, $C_1$-$C_6$ alkyl and oxo; and $R^g$ is selected from the group consisting of $C_1$-$C_6$ alkyl and $C_3$-$C_6$ cycloalkyl wherein the $C_1$-$C_6$ alkyl and $C_3$-$C_6$ cycloalkyl of $R^g$ may be optionally substituted by $C_1$-$C_3$ alkoxy, F, OH, CN, SH, CH$_3$ or CF$_3$.

2. The compound of claim 1, or a stereoisomer, tautomer, solvate, prodrug or pharmaceutically acceptable salt thereof, wherein $A_1$ is NR' or CR$^1$.

3. The compound of claim 1, or a stereoisomer, tautomer, solvate, prodrug or pharmaceutically acceptable salt thereof, wherein $A_2$ is NR$^2$, S or CR$^2$.

4. The compound of claim 1, or a stereoisomer, tautomer, solvate, prodrug or pharmaceutically acceptable salt thereof, wherein ring A is a monocycle.

5. The compound of claim 4, or a stereoisomer, tautomer, solvate, prodrug or pharmaceutically acceptable salt thereof, wherein $A_1$ is CR$^1$, $A_2$ is S, and $A_3$ is C.

6. The compound of claim 5, or a stereoisomer, tautomer, solvate, or pharmaceutically acceptable salt thereof, wherein R$^1$ is NH$_2$.

7. The compound of claim 4, or a stereoisomer, tautomer, solvate, or pharmaceutically acceptable salt thereof, wherein $A_1$ is CR$^1$, $A_2$ is NR$^2$, and $A_3$ is C.

8. The compound of claim 1, or a stereoisomer, tautomer, solvate, or pharmaceutically acceptable salt thereof, wherein ring A is a fused bicycle.

9. The compound of claim 8, or a stereoisomer, tautomer, solvate, or pharmaceutically acceptable salt thereof, wherein $A_1$ is NR$^1$ or CR$^1$, $A_2$ is NR$^2$ or CR$^2$, and R$^1$ and R$^2$ are taken together with the atoms to which they are attached to form a 3-11 membered heterocyclyl optionally substituted by R$^d$.

10. The compound of claim 9, or a stereoisomer, tautomer, solvate, or pharmaceutically acceptable salt thereof, wherein $A_1$ is CR$^1$, $A_2$ is CR$^2$ and $A_3$ is N.

11. The compound of claim 9, or a stereoisomer, tautomer, solvate, prodrug or pharmaceutically acceptable salt thereof, wherein $A_1$ is NR$^1$, $A_2$ is CR$^2$ and $A_3$ is C.

12. The compound of claim 9, or a stereoisomer, tautomer, solvate, prodrug or pharmaceutically acceptable salt thereof, wherein $A_1$ is CR$^1$, $A_2$ is NR$^2$ and $A_3$ is C.

13. The compound of claim 9, or a stereoisomer, tautomer, solvate, or pharmaceutically acceptable salt thereof, wherein ring A is selected from the group consisting of:

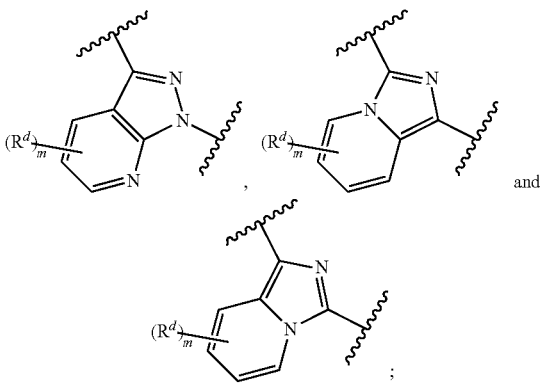

wherein each m is independently 0, 1, 2 or 3.

14. The compound of claim 9, or a stereoisomer, tautomer, solvate, or pharmaceutically acceptable salt thereof, wherein ring A is selected from the group consisting of:

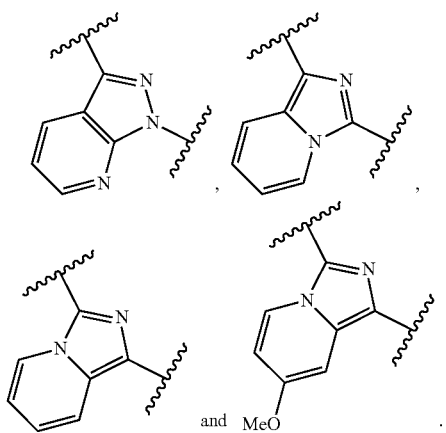

and

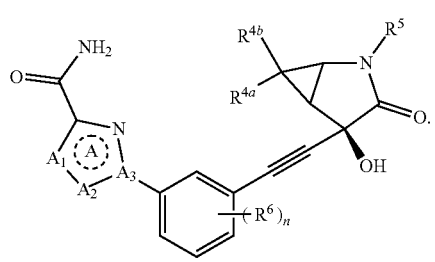

15. The compound of claim 1, or a stereoisomer, tautomer, solvate, or pharmaceutically acceptable salt thereof, wherein $A_7$ is $CR^6$ where $R^6$ is H.

16. The compound of claim 15, or a stereoisomer, tautomer, solvate, or pharmaceutically acceptable salt thereof, wherein Ag is $CR^6$ where $R^6$ is H or F.

17. The compound of claim 16, or a stereoisomer, tautomer, solvate, prodrug or pharmaceutically acceptable salt thereof, wherein $A_5$ is $CR^6$ where $R^6$ is H.

18. The compound of claim 17, or a stereoisomer, tautomer, solvate, or pharmaceutically acceptable salt thereof, wherein $A_6$ is $CR^6$ where $R^6$ is selected from the group consisting of H, F, $OCH_3$ and $CH_3$.

19. The compound of claim 1, or a stereoisomer, tautomer, solvate, or pharmaceutically acceptable salt thereof, wherein the compound is of the formula (Aa):

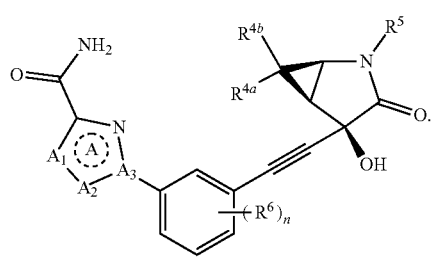

(Aa)

20. The compound of claim 1, or a tautomer, solvate, or pharmaceutically acceptable salt thereof, wherein the compound is of the formula (Aa-1):

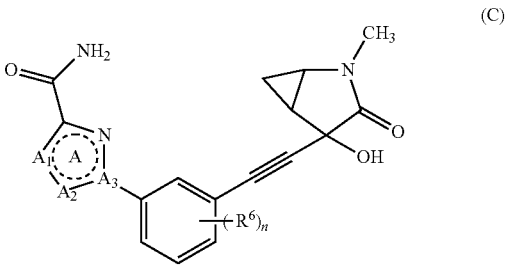

(Aa-1)

21. The compound of claim 1, or a tautomer, solvate, or pharmaceutically acceptable salt thereof, wherein the compound is of the formula (Aa-2):

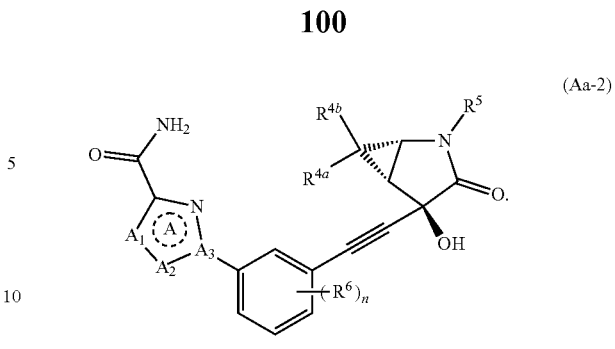

(Aa-2)

22. The compound of claim 1, or a stereoisomer, tautomer, solvate, prodrug or pharmaceutically acceptable salt thereof, wherein each $R^{4a}$ and $R^{4b}$ is H.

23. The compound of claim 1, or a stereoisomer, tautomer, solvate, or pharmaceutically acceptable salt thereof, wherein $R^5$ is methyl.

24. A compound of formula (C):

(C)

or a stereoisomer, tautomer, solvate, or pharmaceutically acceptable salt thereof, wherein:

ring A is a monocycle or a fused bicycle;

$A_1$ is $NR^1$ or $CR^1$;

$A_2$ is $NR^2$, S or $CR^2$;

$A_3$ is N or C;

provided that no more than one of (i)-(iii) applies: (i) Ai is $NW^1$, (ii) $A_2$ is $NR^2$, and (iii) $A_3$ is N;

each $R^1$ is independently —$NR^aR^b$; $C_1$-$C_3$ alkyl optionally substituted by F, OH, CN, SH or $C_1$-$C_3$ alkoxy; or taken together with $R^2$, where present, and the atoms to which they are attached to form a 6-membered heterocyclyl optionally substituted by $R^d$;

each $R^2$ is independently absent or taken together with $R^1$ and the atoms to which they are attached to form a 6-membered heterocyclyl optionally substituted by $R^d$;

n is 0 or 1;

$R^6$, where present, is halo;

each $R^a$ and $R^b$ is independently selected from the group consisting of H and $C_1$-$C_6$ alkyl; and each $R^d$ is independently selected from the group consisting of $C_1$-$C_6$ alkyl optionally substituted by halogen and $C_1$-$C_6$ alkoxy optionally substituted by halogen.

25. The compound of claim 24, or a stereoisomer, tautomer, solvate, or pharmaceutically acceptable salt thereof, wherein the compound is of the formula (D):

101
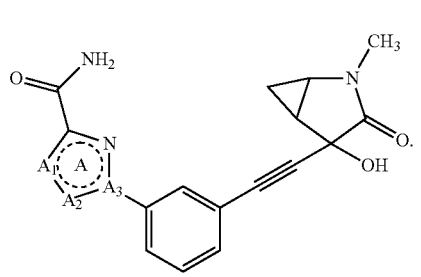
(D)
26. The compound of claim 1, or a pharmaceutically acceptable salt thereof, wherein the compound is selected from the group consisting of:
102
-continued
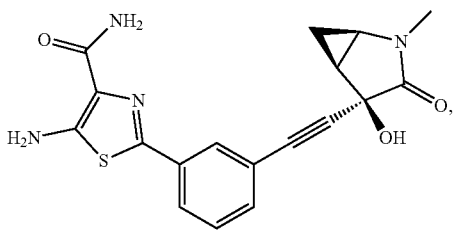
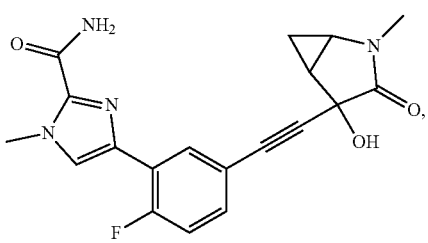
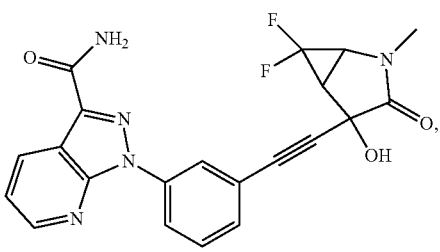
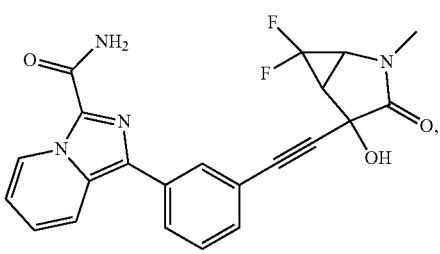
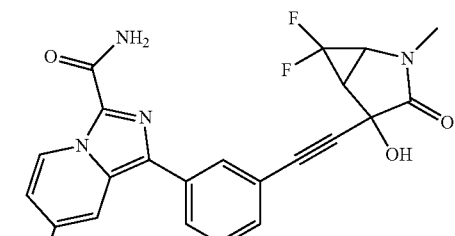
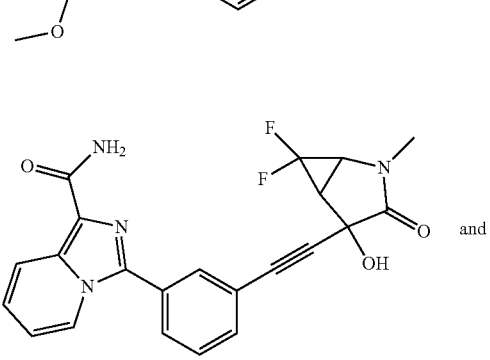
and

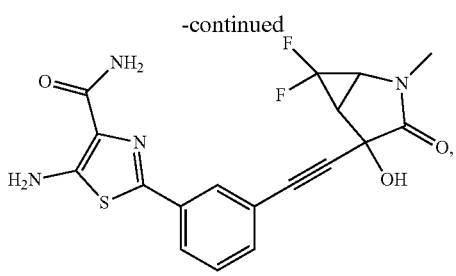

or a pharmaceutically acceptable salt thereof.

27. The compound of claim 1, or a pharmaceutically acceptable salt thereof, wherein the compound is selected from the group consisting of:

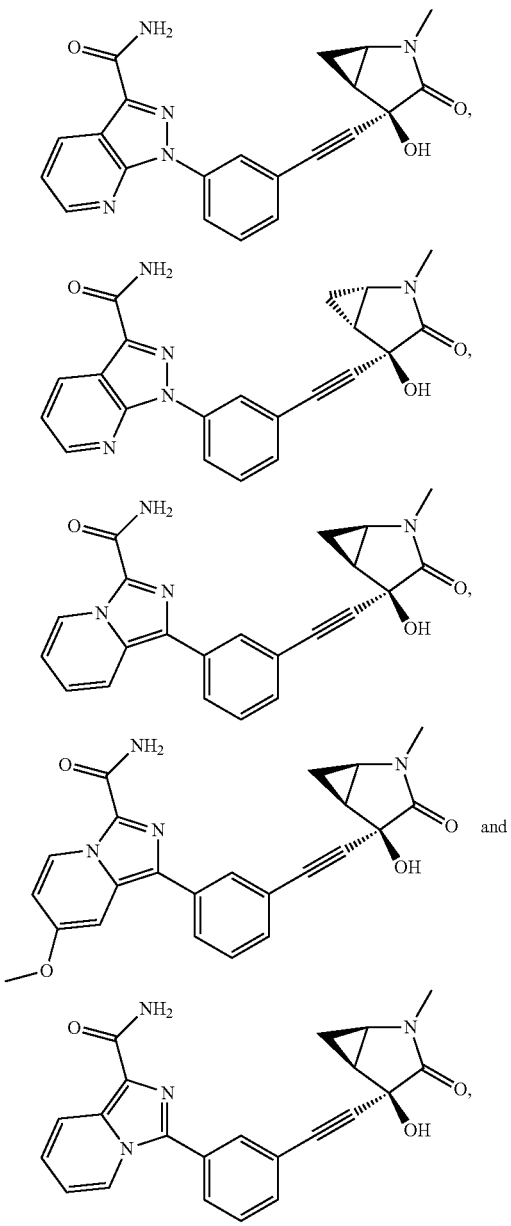

or a pharmaceutically acceptable salt thereof.

28. A pharmaceutical composition comprising a compound of claim 1, or a stereoisomer, tautomer, solvate or, or a pharmaceutically acceptable salt thereof, and a pharmaceutically acceptable carrier, diluent or excipient.

29. A method for the treatment of an inflammatory condition or a fibrotic condition in a patient, comprising administering an effective amount of a compound of claim 1, or a stereoisomer, tautomer, solvate, prodrug or salt thereof, to the patient.

30. The method of claim 29, wherein the inflammatory condition is selected from the group consisting of lupus, systemic lupus erythematosus, chronic obstructive pulmonary disease (COPD), rhinitis, multiple sclerosis, inflammatory bowel disease (IBD), arthritis, rheumatoid arthritis, dermatitis, endometriosis and transplant rejection.

31. A method of making a compound of formula (A):

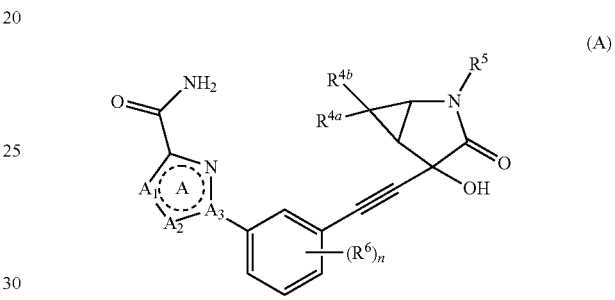

wherein $A_1$-$A_3$, $R^{4a}$, $R^{4b}$, $R^5$, $R^6$, and n are as defined in claim 1, comprising (i) reacting a compound of formula (A-1):

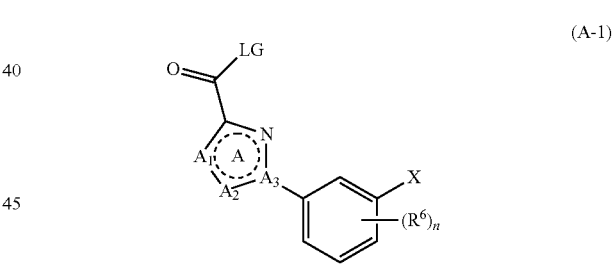

wherein X is —Cl, —Br, —I, —OS(O)$_2$CF$_3$, —OC(O)CH$_3$, —OS(O)$_2$CH$_3$, —OS(O)$_2$(4-CH$_3$C$_6$H$_4$), or —N$_2^+$; and LG is a leaving group;

with a compound of formula (A-2):

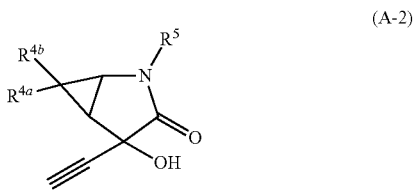

to form a compound of formula (A-3):

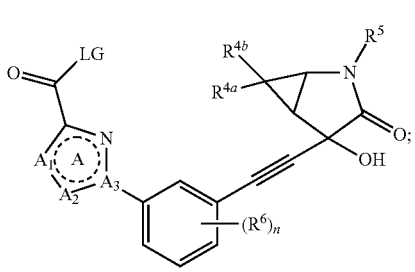

(A-3)

(ii) converting the compound of formula (A-3) to the compound of formula (A).

32. The method of claim 31, further comprising:
(i) reacting a compound of formula (A-4):

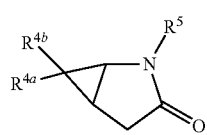

(A-4)

with bis(trimethylsilyl)peroxide to form a compound of formula (A-5):

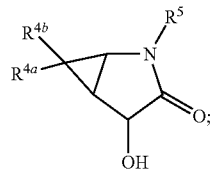

(A-5)

and (ii) converting the compound of formula (A-5) to the compound of formula (A-2).

33. A method of making a compound of formula (C):

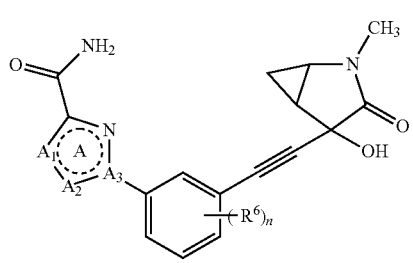

(C)

wherein $A_1$, $A_2$, $A_3$, $R^6$ and n are as defined in claim 24, comprising:

(i) reacting a compound of formula (C-1):

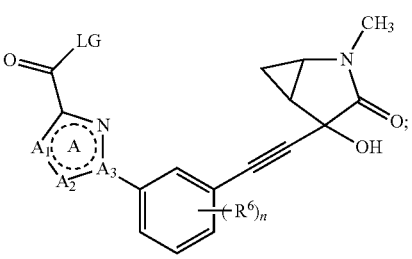

(C-1)

wherein X is $-C_1$, $-Br$, $-I$, $-OS(O)_2CF_3$, $-OC(O)CH_3$, $-OS(O)_2CH_3$, $-OS(O)_2(4\text{-}CH_3C_6H_4)$, or $-N_2^+$; and LG is a leaving group;

with a compound of formula (C-2):

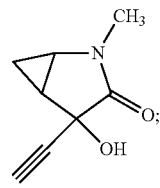

(C-2)

to form a compound of formula (C-3):

(C-3)

and (ii) converting the compound of formula (C-3) to the compound of formula (C).

34. The method of claim 33, further comprising:
(i) reacting a compound of formula (1):

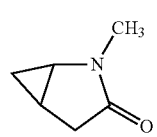

(1)

with bis(trimethylsilyl)peroxide to form a compound of formula (2):

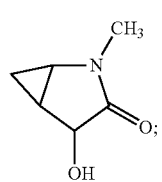 (2)
and
(ii) converting the compound of formula (2) to the compound of formula (C-2).
* * * * *